United States Patent
Liu et al.

(10) Patent No.: US 12,128,099 B2
(45) Date of Patent: Oct. 29, 2024

(54) MYXOMA VIRUS COMPOSITIONS AND METHODS OF USE

(71) Applicant: BIOVENTURES, LLC, Little Rock, AR (US)

(72) Inventors: Jia Liu, Little Rock, AR (US); Martin Cannon, Little Rock, AR (US)

(73) Assignee: BIOVENTURES, LLC, Little Rock, AR (US)

( * ) Notice: Subject to any disclaimer, the term of this patent is extended or adjusted under 35 U.S.C. 154(b) by 867 days.

(21) Appl. No.: 17/058,765

(22) PCT Filed: May 24, 2019

(86) PCT No.: PCT/US2019/033973
§ 371 (c)(1),
(2) Date: Nov. 25, 2020

(87) PCT Pub. No.: WO2019/227022
PCT Pub. Date: Nov. 28, 2019

(65) Prior Publication Data
US 2021/0205442 A1  Jul. 8, 2021

Related U.S. Application Data

(60) Provisional application No. 62/723,887, filed on Aug. 28, 2018, provisional application No. 62/676,663, filed on May 25, 2018.

(51) Int. Cl.
| | | |
|---|---|---|
| A61K 35/00 | (2006.01) | |
| A61K 39/00 | (2006.01) | |
| A61K 39/275 | (2006.01) | |
| A61K 45/06 | (2006.01) | |
| A61P 35/00 | (2006.01) | |

(52) U.S. Cl.
CPC ........ *A61K 39/275* (2013.01); *A61K 39/0011* (2013.01); *A61K 45/06* (2013.01); *A61P 35/00* (2018.01); *A61K 2039/5254* (2013.01); *A61K 2039/545* (2013.01); *A61K 2039/585* (2013.01); *A61K 2039/892* (2018.08)

(58) Field of Classification Search
CPC .......... A61K 39/275; A61K 2039/5254; A61K 2039/585; A61K 2039/892; A61K 39/39558; A61P 35/00
See application file for complete search history.

(56) References Cited

U.S. PATENT DOCUMENTS

| | | |
|---|---|---|
| 7,521,056 B2 | 4/2009 | Chang et al. |
| 7,527,787 B2 | 5/2009 | Chang et al. |
| 7,534,866 B2 | 5/2009 | Chang et al. |
| 7,550,143 B2 | 6/2009 | Chang et al. |
| 7,666,400 B2 | 2/2010 | Chang et al. |
| 8,227,440 B2 | 7/2012 | McFadden et al. |
| 8,512,713 B2 | 8/2013 | Barrett et al. |

FOREIGN PATENT DOCUMENTS

| | | | |
|---|---|---|---|
| EP | 0453082 | 10/1991 | |
| WO | 90/14837 | 12/1990 | |
| WO | WO-2020056424 A1 * | 3/2020 | ........... A61K 31/137 |

OTHER PUBLICATIONS

Nounamo et al, Molecular Therapy: Oncolytics vol. 6 p. 90 (2017). (Year: 2017).*
Cho et al Anticancer Research vol. 33 p. 1317, (2013). (Year: 2013).*
Nounamo et al Molecular Therapy: Oncolytics vol. 6 p. 90 (Sep. 2017) (Year: 2017).*
WO 2020/056424 pp. 1-425 (Year: 2020).*
WO 2020/056424 pp. 426-836 (Year: 2020).*
Alleviating MDR-TB Treatment Side Effects in Botswana. <http://.kncvtbc.org/en/project/alleviating-mdr-tb-treatment-side-effects-in-botswana/> (accessed Jan. 14)).
Ibrahim, N. et al. Barrier to autointegration factor (BAF) inhibits vaccinia virus intermediate transcription in the absence of the viral B1 kinase. Virology 2013, 444(1-2): 363-373.
Ibrahim, N. et al. Molecular characterization of the host defense activity of the barrierto autointegration factor against vaccinia virus. Journal of virology 2011, 85(22): 11588-11600.
International Search Report and Written Opinion for International Patent Application No. PCT/US2019/033973, dated Aug. 16, 2019.
International Search Report and Written Opinion for International Patent Application No. PCT/US2019/062470, dated Feb. 18, 2020.
Kane, M. et al. Identification of Interferon-Stimulated Genes with Antiretroviral Activity. Cell host & microbe 2016, 20(3): 392-405.
Karyampudi, L. et al. PD-1 Blunts the Function of Ovarian Tumor-Infiltrating Dendritic Cells by Inactivating NF-κB. Cancer Res. Jan. 15, 2016;76(2):239-50. doi: 10.1158/0008-5472.CAN-15-0748. Epub Nov. 13, 2015. PMID: 26567141; PMCID: PMC4715980.
Kaufman, H.L. et al. Oncolytic viruses: a new class of immunotherapy drugs. Nat. Rev. Drug Discov. 2015;14:642-662.
Keller, B.A. & Bell, J.C. Oncolytic viruses-immunotherapeutics on the rise. J. Mol. Med. (Berl.) 2016;94:979-991.
Kelley, L.A. et al. The Phyre2 web portal for protein modeling, prediction and analysis. Nature protocols 2015, 10(6): 845-858.
Kerr, P.J. et al. Evolutionary history and attenuation of myxoma virus on two continents. PLoS pathogens 2012, 8(10): e1002950.
Kerr, P.J. et al. Genome scale evolution of myxoma virus reveals host-pathogen adaptation and rapid geographic spread. J Virol. Dec. 2013; 87(23): 12900-12915.
Kerr, P.J. et al. Genomic and phenotypic characterization of myxoma virus from Great Britain reveals multiple evolutionary pathways distinct from those in Australia. PLoS pathogens 2017, 13(3): e1006252.

(Continued)

*Primary Examiner* — Sheela J. Huff
(74) *Attorney, Agent, or Firm* — Quarles & Brady, LLP

(57) ABSTRACT

Mutant Myxoma viruses are provided herein and methods of using these viruses to treat cancer or elicit an interferon response in a subject are also provided. The mutant Myxoma virus is modified to reduce or eliminate the activity or expression of Myxoma virus protein M62 as compared to a control virus. The mutant virus is capable of stimulating an interferon response in subjects after administration and can also lead to inhibition, reduction or elimination of the CD14+ tumor associated macrophage inhibition of CD4+ T cells in a subject having cancer and lead to a change in the tumor microenvironment to treat the cancer or work in combination with other cancer therapeutics to treat the cancer as described herein.

21 Claims, 32 Drawing Sheets

(56) References Cited

OTHER PUBLICATIONS

Kerr, P.J. Myxoma virus and the Leporipoxviruses: an evolutionary paradigm. Viruses 2015, 7(3): 1020-1061.

Klicher, S. et al. siRNA screen of early poxvirus genes identifies the AAA+ ATPase D5 as the virus genome-uncoating factor. Cell host & microbe 2014, 15(1): 103-112.

Knight, M.J. et al. A human sterile alpha motif domain polymerizome. Protein science : a publication of the Protein Society 2011, 20(10): 1697-1706.

Knutson, K.L. et al. Immunoediting of cancers may lead to epithelial to mesenchymal transition. J Immunol. Aug. 1, 2006;177(3):1526-33. doi: 10.4049/jimmunol.177.3.1526. PMID: 16849459.

Kolb, H.C. et al. Click Chemistry: Diverse Chemical Function from a Few Good Reactions. Angewandte Chemie International Edition 2001, 40, 2004-2021.

Kovesdi, I. & Hedley, S.J. Adenoviral producer cells. Viruses. Aug. 2010;2(8):1681-1703. doi: 10.3390/v2081681. Epub Aug. 16, 2010. PMID: 21994701; PMCID: PMC3185730.

Kranzusch, P.J. et al. Ancient Origin of cGAS-STING Reveals Mechanism of Universal 2',3' cGAMP Signaling. Molecular cell 2015, 59(6): 891-903.

Kranzusch, P.J. et al. Structure of human cGAS reveals a conserved family of second-messenger enzymes in innate immunity. Cell reports 2013, 3(5): 1362-1368.

Kryczek, I. et al. B7-H4 expression identifies a novel suppressive macrophage population in human ovarian carcinoma. J Exp Med. Apr. 17, 2006;203(4):871-81. doi: 10.1084/jem.20050930. Epub Apr. 10, 2006. PMID: 16606666; PMCID: PMC2118300.

Lamichhane, P et al. IL10 Release upon PD-1 Blockade Sustains Immunosuppression in Ovarian Cancer. Cancer Res. Dec. 1, 2017;77(23):6667-6678. doi: 10.1158/0008-5472.CAN-17-0740. Epub Oct. 9, 2017. PMID: 28993412; PMCID: PMC5712245.

Lemos De Matos, A. et al. Evolution and divergence of the mammalian SAMD9/SAMD9L gene family. BMC evolutionary biology 2013, 13: 121.

Li, C.F. et al. Human sterile alpha motif domain 9, a novel gene identified as down-regulated in aggressive fibromatosis, is absent in the mouse. BMC Genomics. Apr. 3, 2007:8:92. doi: 10.1186/1471-2164-8-92.

Li, X-D, et al. Pivotal roles of cGAS-cGAMP signaling in antiviral defense and immune adjuvant effects. Science (New York, NY) 2013, 341(6152): 1390-1394.

Liu, J. & McFadden, G. SAMD9 is an innate antiviral host factor with stress response properties that can be antagonized by poxviruses. J Virol. Feb. 2015;89(3):1925-31. doi: 10.1128/JVI.02262-14. Epub Nov. 26, 2014.

Liu, J. et al. M062 is a Host Range Factor Essential for Myxoma Virus Pathogenesis and Functions as an Antagonist of Host SAMD9 in Human Cells. J Virol. 85(7):3270-3282 (2011).

Liu, J. et al. Myxoma virus expressing interleukin-15 fails to cause lethal myxomatosis in European rabbits. Journal of virology 2009, 83(11): 5933-5938.

Liu, J. et al. Myxoma virus M064 is a novel member of the poxvirus C7L superfamily of host range factors that controls the kinetics of myxomatosis in European rabbits. J. Virol. 2012;86:5371-5375.
Liu, J. et al. Reduction in severity of a herpes simplex virus type 1 murine infection by treatment with a ribozyme targeting the UL20 gene RNA. Journal of virology 2008, 82(15): 7467-7474.
Liu, J. et al. The poxvirus C7L host range factor superfamily. Current opinion in virology 2012, 2(6): 764-772.
Loschke, F. et al. Keratin Isotypes Control Desmosome Stability and Dynamics through PKCalpha. The Journal of investigative dermatology 2016, 136(1): 202-213.
Luecke, S. et al. cGAS is activated by DNA in a length-dependent manner. EMBO reports 2017, 18(10): 1707-1715.
MacNeill, A.L. et al. Mutation of the Myxoma virus SERP2 P1-site to prevent proteinase inhibition causes apoptosis in cultured RK-13 cells and attenuates disease in rabbits, but mutation to alter specificity causes apoptosis without reducing virulence. Virology 2006, 356(1-2): 12-22.
Maher, S.G. et al. IFNalpha and IFNlambda differ in their antiproliferative effects and duration of JAK/STAT signaling activity. Cancerbiology & therapy 2008, 7(7): 1109-1115.
Mankan, A.K. et al. Cytosolic RNA:DNA hybrids activate the cGAS-STING axis. The EMBO journal 2014, 33(24): 2937-2946.
McHarg, S. et al. Down-regulation of desmosomes in cultured cells: the roles of PKC, microtubules and lysosomal/proteasomal degradation. PloS one 2014, 9(10): e108570.
Mekhedov, S.L. et al. The complex domain architecture of SAMD9 family proteins, predicted STAND-like NTPases, suggests new links to inflammation and apoptosis. Biology direct 2017, 12(1): 13.
Meng, X. et al. Structural basis for antagonizing a host restriction factor by C7 family of poxvirus host-range proteins. Proceedings of the National Academy of Sciences of the United States of America 2015, 112(48): 14858-14863.
Mercer, J. et al. RNAi screening reveals proteasome- and Cullin3-dependent stages in vaccinia virus infection. Cell reports 2012, 2(4): 1036-1047.
Meruelo, A.D. & Bowie, J.U. Identifying polymer-forming SAM domains. Proteins 2009, 74(1): 1-5.
Messud-Petit, F. et al. Serp2, an inhibitor of the interleukin-1beta-converting enzyme, is critical in the pathobiology of myxoma virus.J Virol. Oct. 1998; 72(10): 7830-7839.
Mezulis, S. et al. PhyreStorm: A Web Server for Fast Structural Searches Against the PDB. Journal of molecular biology 2016, 428(4): 702-708.
Moehler, M. et al. Activation of the human immune system by chemotherapeutic or targeted agents combined with the oncolytic parvovirus H-1. BMC Cancer. 2011;11:464.
Molodtsov, V. et al. Structural basis for rifamycin resistance of bacterial RNA polymerase by the three most clinically important RpoB mutations found in Mycobacteriwn tuberculosis. Molecular Microbiology 2017, 103, 1034-1045.
Molodtsov, V. et al. X-ray Crystal Structures of the *Escherichia coli* RNA Polymerase in Complex with Benzoxazinorifamycins. Journal of Medicinal Chemistry 2013, 56, 4758-4763.
Moo-Young, T.A. et al. Tumor-derived TGF-beta mediates conversion of CD4+Foxp3+ regulatory T cells in a murine model of pancreas cancer. J. Immunother. 2009;32:12-21.
Moss, B. & Filler, R. Irreversible effects of cycloheximide during the early period of vaccinia virus replicaon. J Virol. Feb. 1970; 5(2): 99-108.
"3rd Global GLC Meeting Report 2012. Session I—Report from the gGLC Secretariat," World Health Organization: Geneva, Switzerland, 2012.
Albrecht, L.V. et al. GSK3- and PRMT-1-dependent modifications of desmoplakin control desmoplakin-cytoskeleton dynamics. The Journal of cell biology 2015, 208(5): 597-612.
Almine, J.F. et al. IFI16 and cGAS cooperate in theactivation of STING during DNA sensing in human keratinocytes. Nature communications 2017, 8:14392.
Ansari, M.A. et al. Herpesvirus Genome Recognition Induced Acetylation of Nuclear IFI16 is Essential for Its Cytoplasmic Translocation, Inflammasome and IFN-beta Responses. PLoS pathogens 2015, 11(7): e1005019.
Arulanandam, R. et al. Microtubule disruption synergizes with oncolytic virotherapy by inhibiting interferon translation and potentiating bystander killing. Nat. Commun. 2015;6:6410.
Bartee, E. & and McFadden, G. Human cancer cells have specifically lost the ability to induce the synergistic state caused by tumor necrosis factor plus interferon-beta. Cytokine. 2009;47:199-205.
Bartee, E. et al. Myxoma virus induces ligand independent extrinsic apoptosis in human myeloma cells. Clin. Lymphoma Myeloma Leuk. 2016;16:203-212.
Bartee, E. et al. The addition of tumor necrosis factor plus beta interferon induces a novel synergistic antiviral state against poxviruses in primary human fibroblasts. J. Virol. 2009;83:498-511.
Bauer, D.E. et al. Generation of genomic deletions in mammalian cell lines via CRISPR/Cas9. Journal of visualized experiments : JoVE 2015(95): e52118.

(56) References Cited

OTHER PUBLICATIONS

Becker, K.P. & Hannun, Y.A. cPKC-dependent sequestration of membrane-recycling components in a subset of recycling endosomes. The Journal of biological chemistry 2003, 278(52): 52747-52754.
Best, S.M. & Kerr, P.J. Coevolution of host and virus: the pathogenesis of virulent and attenuated strains of myxoma virus in resistant and susceptible European rabbits. Virology 2000, 267(1): 36-48.
Best, S.M. et al. Coevolution of host and virus: cellular localization of virus in myxoma virus infection of resistant and susceptible European rabbits. Virology 2000, 277(1): 76-91.
Bilsland, A.E. et al. Virotherapy: cancer gene therapy at last? Version 1. F1000Res. 2016; 5: F1000 Faculty Rev-2105.
Braun, C. et al. Genetic Variability of Myxoma Virus Genomes. J Virol. Feb. 15, 2017; 91(4): e01570-16.
Buonocore, F. et al. Somatic mutations and progressive monosomy modify SAMD9-related phenotypes in humans. The Journal of clinical investigation 2017, 127(5): 1700-1713.
Cameron, C. et al. The complete DNA sequence of myxoma virus. Virology. Nov. 25, 1999;264(2):298-318. doi: 10.1006/viro.1999.0001.
Campbell, E.A. et al. Structural Mechanism for Rifampicin Inhibition of Bacterial RNA Polymerase. Cell 2001, 104, 901-912.
Cancer Facts & Figures. 2018. The American Cancer Society. https://.cancer.org/research/cancer-facts-statistics/all-cancer-facts-figures/cancer-facts-figures-2018.html.
Cannon, M.J. et al. Signaling circuits and regulation of immune suppression by ovarian tumor-associated macrophages. Vaccines (Basel) 2015;3:448-466.
Casey, A.E. Studies in the Blood Cytology of the Rabbit : VI Blood Cell Relationships in Groups of Normal Rabbits With Respect to Time. J Exp Med. Apr. 30, 1931;53(5):695-714. doi: 10.1084/jem.53.5.695.
Chan, W.M. & McFadden, G. Oncolytic Poxviruses. Annual review of virology 2014, 1(1): 119-141.
Chan, W.M. et al. Myxoma and vaccinia viruses bind differentially to human leukocytes. J. Virol. 2013;87:4445-4460.
Chan, W.M. et al. Oncolytic myxoma virus: the path to clinic. Vaccine 2013,31(39): 4252-4258.
Chang, C-L, et al. Dose-dense chemotherapy improves mechanisms of antitumor immune response. Cancer Res. 2013;73:119-127.
Chefetz, I. et al. Normophosphatemic familial tumoral calcinosis is caused by deleterious mutations in SAMD9, encoding a TNF-alpha responsive protein. The Journal of investigative dermatology 2008, 128(6): 1423-1429.
Chen, Q. et al. Regulation and function of the cGAS-STING pathway of cytosolic DNA sensing. Nature immunology 2016, 17(10): 1142-1149.
Clift, D. et al. A Method for the Acute and Rapid Degradation of Endogenous Proteins. Cell 2017, 171(7): 1692-1706 e1618.
Cong, L. et al. Multiplex genome engineering using CRISPR/Cas systems. Science (New York, NY) 2013, 339(6121): 819-823.
Correa, R.J. et al. Myxoma virus-mediated oncolysis of ascites-derived human ovarian cancer cells and spheroids is impacted by differential AKT activity. Gynecol. Oncol. 2012;125:441-450.
Dasari S. & Tchounwou, P.B. Cisplatin in cancer therapy: molecular mechanisms of action. Eur. J. Pharmacol. 2014;740:364-378.
Dell'oste, V. et al. Innate nuclear sensor IFI16 translocates into the cytoplasm during the early stage of in vitro human cytomegalovirus infection and is entrapped in the egressing virions during the late stage. Journal of virology 2014, 88(12): 6970-6982.
Dijkgraaf, E.M. et al. Chemotherapy alters monocyte differentiation to favor generation of cancer-supporting M2 macrophages in the tumor microenvironment. Cancer Res. 2013;73:2480-2492.
Ding, S. et al. STAG2 deficiency induces interferon responses via cGAS-STING pathway and restricts virus infection. Nature communications 2018, 9(1): 1485.
Dunlap, K.M. et al. Myxoma virus attenuates expression of activating transcription factor 4 (ATF4) which has implications for the treatment of proteasome inhibitor-resistant multiple myeloma. Oncolytic Virother. 2015;4:1-11.
Dunn, G.P. et al. The immunobiology of cancer immunosurveillance and immunoediting. Immunity. Aug. 2004;21(2):137-48. doi: 10.1016/j.immuni.2004.07.017.
Esteves, P.J. et al. The wide utility of rabbits as models of human diseases. Experimental & molecular medicine 2018, 50(5): 66.
Ferguson, B.J. et al. DNA-PK is a DNA sensor for IRF-3-dependent innate immunity. eLife 2012, 1: e00047.
Fukuhara, H. et al. Oncolytic virus therapy: a new era of cancer treatment at dawn. Cancer Sci. 2016; 107:1373-1379.
Garrod, D & Chidgey, M. Desmosome structure, composition and function. Biochimica et biophysica acta 2008, 1778(3): 572-587.
Georgana, I. et al. Virulent poxviruses inhibit DNA sensing by preventing STING activation. J Virol. Apr. 27, 2018;92(10):e02145-17. doi: 10.1128/JVI.02145-17. Print May 15, 2018.
Global Tuberculosis Report 2017, World Health Organization: Geneva, Switzerland, 2017.
Godsel, L.M. et al. Desmoplakin assembly dynamics in four dimensions: multiple phases differentially regulated by intermediate filaments and actin. The Journal of cell biology 2005, 171(6): 1045-1059.
Goyne, H.E. & Cannon, M.J. Dendritic cell vaccination, immune regulation, and clinical outcomes in ovarian cancer. Front. Immunol. 2013;4:382.
Goyne, H.E. et al. Ovarian tumor ascites CD14+ cells suppress dendritic cell-activated CD4+ T-cell responses through IL-10 secretion and indoleamine 2,3-dioxygenase. J. Immunother. 2014;37:163-169.
Grupp, S.A. et al. Chimeric Antigen Receptor-Modified T Cells for Acute Lymphoid Leukemia. New England J. Med. 368:1509-18, (2013).
Gujar, S.A. Gemcitabine enhances the efficacy of reovirus-based oncotherapy through anti-tumour immunological mechanisms. Br. J. Cancer. 2014;110:83-93.
Hershkovitz, D. et al. Functional characterization of SAMD9, a protein deficient in normophosphatemic familial tumoral calcinosis. The Journal of investigative dermatology 2011, 131(3): 662-669.
Hobbs, R.P. & Green, K.J. Desmoplakin regulates desmosome hyperadhesion. The Journal of investigative dermatology 2012, 132(2): 482-485.
Horan, K.A. et al. Proteasomal degradation of herpes simplex virus capsids in macrophages releases DNA to the cytosol for recognition by DNA sensors. Journal of immunology 2013, 190(5): 2311-2319.
Centers for Disease Control and Prevention. Tuberculosis (TB) <http://cdc.gov/tb/> (accessed Jan. 14, 2022).
Wang, F. et al. RIG-I mediates the co-induction of tumor necrosis factor and type I interferon elicited by myxoma virus in primary human macrophages. PLoS Pathog. 2008;4:e1000099.
Wang, G. et al. Infection of human cancer cells with myxoma virus requires Akt activation via interaction with a viral ankyrin-repeat host range factor. Proc. Natl. Acad. Sci. USA. 2006;103:4640-4645.
Wang, J. et al. Sterile alpha Motif Domain Containing 9 is a Novel Cellular Interacting Partner to Low-Risk Type Human Papillomavirus E6 Proteins. PloS one 2016, 11(2): e0149859.
Wang, M. et al. PaxDb, a database of protein abundance averages across all three domains of life. Mol Cell Proteomics. Aug. 2012; 11(8): 492-500.
Wennier, S.T. et al. Bugs and drugs: oncolytic virotherapy in combination with chemotherapy. Curr. Pharm. Biotechnol. 2012;13:1817-1833.
Wennier, S.T. et al. Myxoma virus sensitizes cancer cells to gemcitabine and is an effective oncolytic virotherapeutic in models of disseminated pancreatic cancer. Mol Ther. Apr. 2012;20(4):759-68. doi: 10.1038/mt.2011.293. Epub Jan. 10, 2012. PMID: 22233582; PMCID: PMC3321583.
Werden, S.J. & McFadden, G. Pharmacological manipulation of the akt signaling pathway regulates myxoma virus replication and tropism in human cancer cells. J Virol.Apr. 2010; 84(7): 3287-3302.
Werden, S.J. et al. The myxoma virus m-t5 ankyrin repeat host range protein is a novel adaptor that coordinately links the cellular

(56) References Cited

OTHER PUBLICATIONS signaling pathways mediated by Akt and Skp1 in virus-infected cells. J Virol. Dec. 2009; 83(23): 12068-12083.
Wiebe, M.S. & Traktman, P. Poxviral B1 kinase overcomes barrier to autointegration factor, a host defense against virus replication. Cell Host Microbe. May 17, 2007;1(3):187-97. doi: 10.1016/j.chom.2007.03.007.
Wilke, C.M. et al. Antigen-presenting cell (APC) subsets in ovarian cancer. Int. Rev. Immunol. 2011;30:120-126.
Woller, N. et al. Oncolytic viruses as anticancer vaccines. Front. Oncol. 2014;4:188.
Wu, J.J., et al. Inhibition of cGAS DNA Sensing by a Herpesvirus Virion Protein. Cell host & microbe 2015, 18(3):333-344.
Yu. H. et al. STATs in cancer inflammation and immunity: a leading role for STAT3. Nat Rev Cancer. Nov. 2009;9 (11):798-809. doi: 10.1038/nrc2734.
Zhang, L. et al. Intratumoral T cells, recurrence, and survival in epithelial ovarian cancer. N. Engl. J. Med. 2003;348:203-213.
Zhang, N. The C. elegans Excretory Canal as a Model for Intracellular Lumen Morphogenesis and In Vivo Polarized Membrane Biogenesis in a Single Cell: labeling by GFP-fusions, RNAi Interaction Screen and Imaging. J Vis Exp. 2017; (128): 56101.
Zhang, Z. et al. The helicase DDX41 senses intracellular DNA mediated by the adaptor STING in dendritic cells. Nature immunology 2011, 12(10): 959-965.
Nair, R.R et al. Role of STAT3 in transformation and drug resistance in CML. Front. Oncol. 2012;2:30.
Nejad, E.B. et al. Tumor eradication by cisplatin is sustained by CD80/86-mediated costimulation of CD8+ T cells. Cancer Res. 2016;76:6017-6029.
Nounamo, B. et al. Myxoma Virus Optimizes Cisplatin for the Treatment of Ovarian Cancer In Vitro and in a Syngeneic Murine Dissemination Model. Mol Ther Oncolytics. Aug. 9, 2017;6:90-99. doi: 10.1016/j.omto.2017.08.002. PMID: 28875159; PMCID: PMC5573804.
Oguiura, N. et al. Detection of a protein encoded by the vaccinia virus C7L open reading frame and study of its effect on virus multiplication in different cell lines. The Journal of general virology 1993, 74 ( Pt 7): 1409-1413.
Ohmichi, T. et al. Efficient bacterial transcription of DNA nanocircle vectors with optimized single-stranded promoters. Proceedings of the National Academy of Sciences 2002, 99. 54-59.
Ossovskaya, V. et al. Upregulation of Poly (ADP-Ribose) Polymerase-1 (PARP1) in Triple-Negative Breast Cancer and Other Primary Human Tumor Types. Genes Cancer. Aug. 2010;1(8):812-21.
Ozols, R.F. Challenges for chemotherapy in ovarian cancer. Ann. Oncol. 2006; 17(Suppl 5):v181-v187.
Pagano, J.M. et al. Quantitative approaches to monitor protein-nucleic acid interactions using fluorescent probes. RNA. Jan. 2011;17(1):14-20. doi: 10.1261/rna.2428111. Epub Nov. 22, 2010.
Paijo, J. et al. cGAS Senses Human Cytomegalovirus and Induces Type I Interferon Responses in Human Monocyte-Derived Cells. PLoS pathogens 2016, 12(4): e1005546.
Pandha, H.S. et al. Synergistic effects of oncolytic reovirus and cisplatin chemotherapy in murine malignant melanoma. Clin. Cancer Res. 2009;15:6158-6166.
Pennington, T.H. Vaccinia virus polypeptide synthesis: sequential appearance and stability of pre- and post-replicative polypeptides. J Gen Virol. Dec. 1974;25(3):433-44. doi: 10.1099/0022-1317-25-3-433.
Peters, N.E. et al. A mechanism for the inhibition of DNA-PK-mediated DNA sensing by a virus. PLoS pathogens 2013, 9(10): e1003649.
Preston, C.C. et al. The ratios of CD8+ T cells to CD4+CD25+ FOXP3+ and FOXP3− T cells correlate with poor clinical outcome in human serous ovarian cancer. PLoS One. Nov. 14, 2013;8(11):e80063. doi: 10.1371/journal.pone.0080063. PMID: 24244610; PMCID: PMC3828213.
Rahman, M.M. et al. Myxoma virus protein M029 is a dual function immunomodulator that inhibits PKR and also conscripts RHA/DHX9 to promote expanded host tropism and viral replication. PLoS pathogens 2013, 9(7): e1003465.
Ran, F.A. et al. Genome engineering using the CRISPR-Cas9 system. Nature protocols 2013, 8(11): 2281-2308.
Ribas, A. & Wolchok, J.D. Cancer immunotherapy using checkpoint blockade. Science. Science. Mar. 23, 2018;359(6382):1350-1355. doi: 10.1126/science.aar4060. Epub Mar. 22, 2018.
Roby, K.F. et al. Development of a syngeneic mouse model for events related to ovarian cancer. Carcinogenesis. 2000;21:585-591.
Rochester, S.C. & Traktman, P. Characterization of the single-stranded DNA binding protein encoded by the vaccinia virus I3 gene. J Virol. Apr. 1998; 72(4): 2917-2926.
Rosenberg, S.A. et al. Adoptive cell transfer: a clinical path to effective cancer immunotherapy. Nat. Rev. Cancer 8(4): 299-308 (2008).
Satheshkumar, P.S. et al. Inhibition of the ubiquitin-proteasome system prevents vaccinia virus DNA replication and expression of intermediate and late genes. J Virol. Mar. 2009;83(6):2469-79.
Sayers, S. et al. Vaxjo: a web-based vaccine adjuvant database and its application for analysis of vaccine adjuvants and their uses in vaccine development. J Biomed Biotechnol. 2012;2012:831486. doi: 10.1155/2012/831486. Epub Mar. 13, 2012. PMID: 22505817; PMCID: PMC3312338.
Schmidt, F.I. et al. Vaccinia virus entry is followed by core activation and proteasome-mediated release of the immunomodulatory effector VH1 from lateral bodies. Cell reports 2013, 4(3): 464-476.
Schust, J. et al. Stattic: a small-molecule inhibitor of STAT3 activation and dimerization. Chem. Biol. 2006; 13:1235-1242.
Schwartz, J.R. et al. Germline SAMD9 mutation in siblings with monosomy 7 and myelodysplastic syndrome. Leukemia. Aug. 2017;31(8):1827-1830. doi: 10.1038/leu.2017.142. Epub May 10, 2017.
Senkevich, T.G. et al. Identification of Vaccinia Virus Replisome and Transcriptome Proteins by Isolation of Proteins on Nascent DNA Coupled with Mass Spectrometry. J Virol. Sep. 12, 2017;91(19):e01015-17. doi: 10.1128/JVI.01015-17. Print Oct. 1, 2017.
Seo, G.J. et al. Akt Kinase-Mediated Checkpoint of cGAS DNA Sensing Pathway. Cell reports 2015, 13(2): 440-449.
Shchelkunov, S.N. An increasing danger of zoonotic orthopoxvirus infections. PLoS pathogens 2013,9(12):e1003756.
Shen, Y.J. et al. Genome-derived cytosolic DNA mediates type I interferon-dependent rejection of B cell lymphoma cells. Cell reports 2015, 11(3): 460-473.
Simpson, G.R. et al. Cancer immunotherapy via combining oncolytic virotherapy with chemotherapy: recent advances. Oncolytic Virother. 2016;5:1-13.
Sivan, G. Identification of Restriction Factors by Human Genome-Wide RNA Interference Screening of Viral Host Range Mutants Exemplified by Discovery of SAMD9 and WDR6 as Inhibitors of the Vaccinia Virus K1L-C7L- Mutant. mBio 2015, 6(4): e01122.
Spiesschaert, B. et al. The current status and future directions of myxoma virus, a master in immune evasion. Veterinary research 2011, 42: 76.
Clinical Trials Arena. Spotlight on IDO Inhibitors with crucial clinical trial readout on the horizon. Mar. 2, 2018. <https://www.clinicaltrialsarena.com/comment/spotlight-ido-inhibitors-crucial-clinical-trial-readout-horizon/?cf-view&cf-closed>.
Springer, Y.P. et al. Novel Orthopoxvirus Infection in an Alaska Resident. Clin Infect Dis. Jun. 15, 2017; 64(12):1737-1741.
Suen, W.W. et al. Tissue-specific transcription profile of cytokine and chemokine genes associated with flavivirus control and non-lethal neuropathogenesis in rabbits. Virology 2016, 494: 1-14.
Sun, L. Cyclic GMP-AMP synthase is a cytosolic DNA sensor that activates the type I interferon pathway. Science (New York, NY) 2013, 339(6121): 786-791.
Tan, M.C. Disruption of CCR5-dependent homing of regulatory T cells inhibits tumor growth in a murine model of pancreatic cancer. J. Immunol. 2009; 182:1746-1755.
Taylor, R.T. et al. TRIM79alpha, an interferon-stimulated gene product, restricts tick-borne encephalitis virus replication by degrad-

(56) References Cited

OTHER PUBLICATIONS ing the viral RNA polymerase. Cell Host Microbe. Sep. 15, 2011; 10(3): 185-196. doi:10.1016/j.chom.2011.08.004.

Thorne, S.H. et al. Targeting localized immune suppression within the tumor through repeat cycles of immune cell-oncolytic virus combination therapy. Mol. Ther. 2010;18:1698-1705.

Tolonen, N. et al. Vaccinia virus DNA replication occurs in endoplasmic reticulum-enclosed cytoplasmic mini-nuclei. Mol Biol Cell. Jul. 2001; 12(7): 2031-2046.

Tong, J.G. et al. Evidence for differential viral oncolytic efficacy in an in vitro model of epithelial ovarian cancer metastasis. Mol. Ther. Oncolytics. 2015;2:15013.

Topaz, O. et al. A deleterious mutation in SAMD9 causes normophosphatemic familial tumoral calcinosis. Am J Hum Genet. Oct. 2006;79(4):759-64. doi: 10.1086/508069. Epub Aug. 24, 2006.

Tseng, C.W. et al. Pretreatment with cisplatin enhances E7-specific CD8+ T-cell-mediated antitumor immunity induced by DNA vaccination. Clin. Cancer Res. 2008;14:3185-3192.

UniProt Q5K651. SAMD9_Human, Nov. 7, 2018 [online]. Retrieved Jan. 29, 2020]. <URL:https://www/uniprot.org/uniprot/Q5K651.txt?version=125>.

Unterholzner, L. et al. IFI16 is an innate immune sensor for intracellular DNA. Nature immunology 2010, 11(11):997-1004.

Van Den Boogaard, J. et al. New Drugs against Tuberculosis: Problems, Progress, and Evaluation of Agents in Clinical Development. Antimicrobial Agents and Chemotherapy 2009, 53, 849-862.

Villa, N.Y. et al. Myxoma and vaccinia viruses exploit different mechanisms to enter and infect human cancer cells. Virology 2010, 401(2): 266-279.

Walton, J. et al. CRISPR/Cas9-Mediated Trp53 and Brca2 Knockout to Generate Improved Murine Models of Ovarian High-Grade Serous Carcinoma. Cancer Res. Oct. 15, 2016;76(20):6118-6129. doi: 10.1158/0008-5472.CAN-16-1272. Epub Aug. 16, 2016. PMID: 27530326; PMCID: PMC5802386.

Wang, F. et al. Disruption of Erk-dependent type I interferon induction breaks the myxoma virus species barrier. Nature immunology 2004, 5(12): 1266-1274.

Wang, F. et al. Induction of alpha/beta interferon by myxoma virus is selectively abrogated when primary mouse embryo fibroblasts become immortalized. J. Virol. 2009;83:5928-5932.

\* cited by examiner

FIG. 6C

Splenocyte response to the tumor antigen

Legend: Cis alone-1, Cis alone-2, wt alone-1, wt alone-2, Cis+wt, wt+cis-1, wt+cis-2

Y-axis: IFNγ (pg/mL)
X-axis: Days post stimulation — 1st stimulation (1, 3), 2nd stimulation (7, 10)

FIG. 6D

M062R-null MYXV and cisplatin treatment in the syngeneic ID8 OC model

Y-axis: Percent survival
X-axis: Days post-inoculation

Legend:
- PBS
- Cisplatin (early) alone
- vMyxM062RKO first and cisplatin later
- cisplatin first and vMyxM062RKO later

FIG. 9A

MYXV infection affects gene expression in patient ovarian cancer cells: KAJ434

FIG. 9B

MYXV infection affects gene expression in patient ovarian cancer cells: OvCa-37

FIG. 9D

MYXV infection affects gene expression in ID8 TP53⁻/⁻

FIG. 13A

MYXV infection affects gene expression in primary human KAJ434

FIG. 13B

MYXV infection affects gene expression in primary human OvCa-43

☐ wt MYXV   ■ *M062R-null MYXV*

FIG. 14A
M062R-null MYXV stimulates ISG expression in human macrophage-like THP-1 cells

FIG. 14B
IFNβ mRNA upon infection

- ISD
- vMyxGFP (wt)
- vMyxM062RKO

Luciferase expression in THP-1 infected with vMyx*M062R*KO

2'3'-cGAMP stimulates a type I IFN response regardless of cGAS status in THP-1

Viral infection and type I IFN response with subsequent HT DNA transfection

Poxvirus post-replicative proteins have little effect on viral inhibition of DNA-mediated IFN-I

US 12,128,099 B2

MYXOMA VIRUS COMPOSITIONS AND METHODS OF USE

CROSS-REFERENCE TO RELATED APPLICATIONS

This application is a national stage filing under 35 U.S.C. § 371 of International Patent Application No. PCT/US2019/033973, filed May 24, 2019, which claims priority to U.S. Provisional Application No. 62/676,663 filed on May 25, 2018 and U.S. Provisional Application No. 62/723,887 filed on Aug. 28, 2018, the contents of which are incorporated by reference in their entireties.

STATEMENT REGARDING FEDERALLY SPONSORED RESEARCH

This invention was made with United States government support awarded by the National Institute of Health (NIH) grant numbers P20GM103625 and K22-AI099184. The United States has certain rights in this invention.

INTRODUCTION

Immune response and especially immune status within the tumor environment play critical roles in cancer progression, overall prognosis, and survival. The presence of tumor infiltrating lymphocytes is associated with prolonged survival. Tumor cells, however, cultivate the tumor environment to impair antitumor immunity, an activity that has been associated with poor survival and prognosis; this immunosuppressive tumor environment is also a major obstacle for effective treatments of cancer, including chemotherapeutic regimens and dendritic cell vaccination. Thus, there is a need in the art for an integrated treatment strategy that not only complements current therapies but also alleviates immune suppression in the tumor environment could benefit the treatment of cancer patients.

SUMMARY

In one aspect of the present invention, myxoma viruses are provided. The myxoma virus may be a mutant myxoma virus modified to eliminate or reduce as compared to a control myxoma virus the activity or expression of a Myxoma virus protein M062R.

In another aspect, the present invention relates to compositions including a mutant myxoma virus and an anti-cancer therapeutic agent.

In a further aspect, the present invention relates to pharmaceutical compositions including any one of the compositions described herein and a pharmaceutically acceptable carrier and/or an adjuvant.

In another aspect, the present invention relates to kits. The kits may include a myxoma virus, such as any of the myxoma viruses described herein, and an anti-cancer therapeutic agent. Optionally, the kits may further include the components required to perform any of the methods disclosed herein.

In a still further aspect of the present invention, methods of treating cancer in a subject are provided. The methods may include administering a therapeutically effective amount of any of the compositions described herein to the subject. Alternatively, the methods may include administering to the subject a therapeutically effective amount of any one of the myxoma viruses described herein, and administering to the subject a therapeutically effective amount of one or more anti-cancer therapeutic agent.

BRIEF DESCRIPTION OF DRAWINGS

FIGS. 1A-1D show MYXV Infection in OC Cells and Oncolysis. (FIG. 1A) MYXV multistep growth comparison in primary OC cells. Replication-competent (vMyxGFP [WT]) or -defective (vMyxM062RKO) MYXV was used at an MOI of 0.1 to infect primary OvCa-26 OC cells. Cell lysates were harvested at given time points and viral yields estimated by titering on BSC-40 cells. The mean titer from the titration in triplicate is shown at each time point, and the error bar represents the SD. Shown is a representative of two independent experiments. (FIGS. 1B and 1C) Infection by MYXV led to reduced cell viability. In both primary OC cells, such as OvCa-26 (FIG. 1B) and the OC cell line SKOV3 (FIG. 1C), infection by WT or M062R-null MYXV at an MOI of either 5 or 10 led to reduced cell viability as measured by MTT assay. However, the differences in cell viability between the two virus treatments did not reach statistical significance. The error bar represents SD from the quantification in triplicate, and shown is a representative of two independent experiments. (FIG. 1D) MYXV infection eliminated colony formation by OC tumor cells. SKOV3 cells (5×103) were either mock infected or infected with MYXV (MOI=10) for 1 hr and then seeded in plates. After approximately 3 weeks of culture, cells were fixed and stained with crystal violet to detect colony formation.

FIGS. 2A-2B show apoptosis was not the main cause for MYXV infection-associated cell death in OC tumor cells. SKOV3, OvCa-26, and OvCa-2a cells were mock treated, infected with either vMyxGFP (WT) or vMyxM062RKO at an MOI of 5 for 24 hr before being stained with Annexin V and propidium iodide (PI) for flow cytometry. Cells from the infection group were gated first with forward scatter to side scatterplot (FSC/SSC) followed by the GFP-positive population (FIG. 2A) to analyze the Annexin V-PI staining. Next, GFP-negative cells were gated (FIG. 2B) to analyze the Annexin V-PI staining. This is a representative view of three independent experiments. In the quadrants shown, x and y axes indicate fluorescence intensity, while quadrants of each cell line were defined with the use of mock-treated samples, respectively.

FIGS. 3A-3B show MYXV treatment complements chemotherapy in a replication-independent manner against primary OC tumor cells. (FIG. 3A) MYXV complements gemcitabine for improved cytotoxicity. Primary patient-ascites-derived OvCa-2a tumor cells were mock-treated or infected with MYXV (WT or M062R null MYXV) at an MOI of 10; gemcitabine treatment at the given doses followed, or pretreatment with gemcitabine was given before viral infection. The first treatment (virus or chemotherapy) lasted 48 hr, followed by 24 hr of growth in fresh medium; cells were then treated with a second treatment (chemotherapy or virus) for another 48 hr before cell viability was measured. (FIG. 3B) MYXV complements cisplatin-associated cytotoxicity. The primary OvCa-26 OC cell line was used in this study, together with cisplatin. The study was conducted similarly to that with gemcitabine as described above. The error bar represents the SEM, and the mean is calculated from quantification in triplicate. Shown is a representative of two independent experiments.

FIGS. 4A-4C shows MYXV infection in OC ascites-associated CD14+ monocytes remodels the intracellular signaling pathway. (FIG. 4A) OC patient ascites-associated CD14+ monocytes/macrophages display non-canonical STAT3 signaling. CD14+ monocytes were enriched from ascites fluid of patient (e.g., OvCa37) and tested for phosphorylation of STAT3 on both Y705 and 5727 by flow cytometry. The signature of non-canonical STAT3 signaling is characterized by minimal phosphorylation at the Y705 site of STAT3. (FIG. 4B) MYXV infection in ascites-associated CD14+ monocytes causes inhibition of STAT3 phosphorylation at the Ser727 residue. CD14+ monocytes were enriched from patient-ascites fluid and tested for purity via flow cytometry. Monocytes were immediately mock treated and infected with WT or M062R-null MYXV at an MOI of 10 for 1 h; washing with PBS followed before the cells were cultured for 18 hr. Media was harvested for multiplex array (FIGS. 5A-5D). Cells were fixed and permeablized for intracellular staining as described in the Materials and Methods to examine the level of STAT3 phosphorylation at the Ser727 residue. (FIG. 4C) Infection by MYXV does not cause general change in cell viability in ascites CD14+ cells. Patient CD14+ ascites-associated monocytes were mock treated or infected with WT or M062R-null MYXV for 18 hr before the cells were stained with propidium iodide (PI). Live cells were gated to examine GFP (infection) and the presence of PI staining.

FIGS. 5A-5D show MYXV Infection in Patient-Ascites-Associated CD14+ Monocytes Inhibits Cytokine Secretion that Is the Signature of Immunosuppressive Tumor Environment. Patient-ascites-associated CD14+ monocytes or CD14+ monocytes from a healthy female donor were mock treated or infected with WT or M062R-null MYXV for 18 hr before supernatant was collected for multiplex array. Comparisons in levels of IL-10 (FIG. 5A) and IL-6 (FIG. 5B) are shown for mock treatment and infection in patients and healthy monocytes. To test the effect of STAT3 in cytokine secretion, patient-ascites-associated CD14+ monocytes were treated with 5 µM Stattic, a STAT3 inhibitor, for 48 hr before supernatant was collected for multiplex array. (FIGS. 5C and 5D) The effect of Stattic on the levels of IL-10 (FIG. 5C) and IL-6 (FIG. 5D) in patient monocytes. The error bars represents SD, and the mean is calculated from the quantification in triplicate.

FIGS. 6A-6D show combinatorial treatment of MYXV and cisplatin for OC disseminated tumor in a syngeneic murine model. (FIG. 6A) Multistep growth comparison of viral replication by WT and M062R-null MYXV. In the murine OC cell line ID8, similar to most cells tested, M062R-null MYXV underwent abortive infection. After infection by MYXV, ID8 cell lysates were harvested at given time points. Viral yields are quantified by titration. The error bar represents SEM, and the mean is calculated from the quantification in triplicate. Shown is a representative of two independent experiments. (FIG. 6B) MYXV pretreatment enhanced cisplatin effect in the ID8 OC dissemination model. At 7 days post-tumor-cell-injection, mice were either mock treated or treated with WT MYXV or cisplatin as described in the Materials and Methods. A second treatment occurred 5 days after the first treatment. Statistical analysis was carried out with the log-rank (Mantel-Cox) test ($p<0.0001$) and the Gehan-Breslow-Wilcoxon test ($p<0.0001$). Median survival (days) is calculated as follows: PBS (n=8) 82 (days); cisplatin (late) only (n=7), 113; WT MYXV only (n=10), undefined; WT MYXV+ cisplatin (n=10), undefined; cisplatin first+WT MYXV later (n=10), 127.5. *$p<0.05$, *$p<0.001$, **$p<0.0001$. (FIG. 6C) Response to tumor antigen in mouse splenocytes from different treatments. Splenocytes harvested from mice treated with WT MYXV followed by cisplatin showed high levels of IFNγ when they were stimulated with ID8 tumor antigen. After 140 days, surviving mice from virus treated alone or combination treatment are euthanized to collect splenocytes; as controls, splenocytes were also harvested from mice with cisplatin alone at approximately 100 days for the test. Freshly harvested splenocytes were immediately stimulated with tumor cell lysate at day 0. Samples of supernatant were collected at days 1 and 3 post-stimulation. These splenocytes continued to be cultured, and at day 6, fresh media were added to include tumor cell lysate. On days 7 and 10, supernatant was collected to test IFNγ by ELISA. The error bar represents SD from the quantification in duplicate. Shown are representative mice of following groups: cisplatin alone (n=2), WT MYXV alone (n=2), cisplatin first plus WT MYXV later (n=1), and WT MYXV first+ cisplatin later (n=2). (FIG. 6D) M062R-null MYXV can be used in combination with cisplatin to achieve therapeutic benefit. Similar to (FIG. 6C), M062R-null MYXV was tested in the combinatorial treatment. Statistical significance was determined with the log-rank (Mantel-Cox) test ($p<0.0001$), the log-rank test for trend ($p<0.0001$), and the Gehan-Breslow-Wilcoxon test ($p<0.0001$). Median survival (days) is calculated as following: PBS (n=8) 80 (days); vMyxM062RKO first+ cisplatin later (n=10), undefined; Cisplatin first+vMyxM062RKO later (n=10), undefined; cisplatin (early) alone (n=10), 127. *$p<0.05$, ****$p<0.001$.

FIGS. 7A-7B show MYXV complements chemotherapy in a replication independent manner against primary OC tumor cells. (FIG. 7A) MYXV complements cisplatin for improved cytotoxicity. Primary patient ascites—derived OvCa-2a tumor cells were mock-treated or infected with MYXV (wt or M062R-null MYXV) at an moi of 10; cisplatin treatment at 5 µM followed by infection, or cisplatin was given before viral infection. The first treatment (virus or chemotherapy) lasted 48 h, followed by 24 h of growth in fresh medium; cells were then treated with a second treatment (chemotherapy or virus) for another 48 h before cell viability was measured by MTT assay similarly as shown in FIGS. 3A-3B. (FIG. 7B). MYXV complements gemcitabine-associated cytotoxicity. The primary OvCa-26 OC cell line was used in this study to test combinatorial effect with gemcitabine at a dose of 10 µM. The study was conducted similarly to that is described above.

FIG. 8 shows single-agent MYXV used to treat ID8 disseminated tumor-bearing mice at late time point significantly prolongs survival. Mice injected with $6 \times 10^6$ tumor cells were treated with corresponding therapy as shown at 16 days post-tumor injection. Kaplan-Meier survival curve is shown along with the treatment schedule. Statistical analysis was carried out with the log-rank (Mantel-Cox) test ($p<0.0001$) and the Gehan-Breslow-Wilcoxon test ($p<0.0001$). The median survival time of each treatment group is as following: PBS (n=5) 65 days; Gemcitabine (n=8) 78; Cisplatin (n=8) 90; vMyxGFP (wt) (n=8) 101.5; vMyxM062RKO (n=8) 102.5. *$p<0.05$ and ***$p<0.0001$.

FIGS. 9A-9E show infection with MYXV and especially M062R-null MYXV produces a type I IFN response in tumor cells. (FIGS. 9A-9C) In ascites-associated primary tumor cells generated from 3 OC patients MYXV (white bars) or M062R-null MYXV (black bars) evokes message for IFNβ and ISGs. (FIG. 9D) In ID8 Trp53−/− cells infection with WT MYXV and M062R-null MYXV virus similarly evokes IFNβ and inflammatory cytokines. The M062R-null MYXV virus undergoes an abortive infection yet evokes a pronounced IFN-I response. SP17 is a known OC tumor antigen marker that is upregulated subsequent to infection (red box). This is an OC-specific tumor antigen with which the DCs are pulsed ex vivo. (FIG. 9E) In the monocytic cell line THP-1-derived macrophages, M062R-null MYXV potently stimulates IFN-1 response than does the WT MYXV. (ISD: IFN stimulatory double-stranded DNA).

FIGS. 10A-10B show infection with WT MYXV improves survival in the ID8 Trp53$^{-/-}$ model of OC. In mice implanted with ID8 Trp53$^{-/-}$ cells, WT MYXV alone improves survival as well as cisplatin alone, but in combination with cisplatin (see dosing timeline in FIG. 10A) performs significantly better than cisplatin alone (p=0.025). The regimen consisting of WT MYXV and DC vaccination performs equally well with the triple therapeutic regimen in FIG. 10B.

FIGS. 11A-11B show treatment with M062R-null MYXV is most effective in an established tumor environment. (FIG. 11A) Administration of cisplatin (3 mg/kg), DC vaccination, and either early or late virotherapy with M062R-null MYXV ($1 \times 10^8$ pfu) for combinatorial treatment result in significantly increased mean survival times (p<0.0001, Mantel-Cox test). (FIG. 11B) Different from other monotherapies that early treatment increases the chance of survival in this aggressive disease model, the late administration with M062R-null MYXV virus after tumor implantation is more efficacious than an early administration (p=0.003).

FIG. 12 shows MYXV infection upregulates expression of immune response genes and Sp17 tumor antigen in IDS TP53$^{-/-}$ cells. MYXV infection in cancer cells induced expression of interferon stimulated genes (ISGs), inflammatory cytokines, and tumor antigen Sp17 (red frame).

FIGS. 13A-13B show MYXV infection upregulates expression of immune response genes and Sp17 tumor antigen in primary human OC cells. Similar results were observed by RT-PCR screening in primary OC cells from human patients. Shown are representative results from two patients. Red frame: Sp17 tumor antigen.

FIGS. 14A-14B show infection with vMyxM062RKO is immunostimulatory and evokes a type I IFN response in THP-1 cells. (FIG. 14A) THP-1-Lucia cells express luciferase under the control of an IRF-inducible promoter and are not responsive to NFκB or AP-1. THP-1 Lucia differentiated macrophages were transfected with IFN stimulated DNA (ISD) or infected with WT or M062R-null (vMyxM062RKO) MYXV. A marked increase in luciferase activity was associated with infection by vMyxM062RKO and ISD transfection. ISD: IFN-stimulatory DNA. (FIG. 14B). RT-PCR showed a sharp increase in the quantity of IFNβ mRNA early during vMyxM062RKO infection. As a control, ISD also stimulated IFNβ expression. However, WT MYXV infection effectively suppressed IFNβ.

FIGS. 15A-15D show SAMD9 ablation diminishes the IFN-I response. We engineered THP-1 cells with shRNA SAMD9 knockdown (SAMD9 KD), and as a control THP-1 cells were constructed to stably express scramble shRNAs. (FIG. 15A) THP-1 differentiated macrophages were transfected with ISD and the expression of IFNβ mRNA was measured by qPCR at the indicated time points. BD. Expression of IFNβ (FIG. 15B) and the IFN stimulated genes (ISGs), including CXCL-10 (FIG. 15D), and ISG54 (FIG. 15C) were quantified by RT-PCR in cells infected with vMyxM062RKO (moi=10). In every case, the SAMD9-ablated cells mount a smaller IFN-I response than do the SAMD9-competent cells. Inset: WB demonstrating that SAMD9 is ablated in THP-1SAMD9 KD cells. Lane 1: THP-1 control cells expressing scrambled shRNAs have the full compliment of SAMD9, while the THP-1SAMD8 KD cells (lane 2) express less SAMD9. β-actin was used as a loading control.

FIGS. 16A-16C show the role of the cytoplasmic DNA sensor cGAS. (FIG. 16A) In cGAS-null THP-1 differentiated macrophages infection with vMyxM062RKO failed to generate an IFN-I response, in sharp contrast to the infection of cGAS-intact cells. (FIG. 16B) 2'3'-cGAMP induces a similar increase in luciferase expression (a surrogate for IFNβ) from both THP-1 with and without cGAS. (FIG. 16C) SAMD9 KD cells responded comparably to control cells when they are exposed to an intermediate dose of 2'3'-cGAMP (500 ng/ml). Expression of IFNβ was measured by RT-PCR.

FIGS. 17A-17B show MYXV M062 contributes to viral inhibition of DNA-mediated IFN-I. THP-1 Lucia cells were infected with the indicated virus for 6 hrs (VACV) or 12 hrs (MYXV) and then transfected with herring testis (HT) DNA or mock treated and the effect, if any, upon the development of the IFN-I response was determined by luciferase activity assay. (FIG. 17A) M062 contributes to direct inhibition of DNA-mediated IFN-I. (FIG. 17B) Post-replicative M062 is unlikely to participate in the inhibition of DNA-stimulated IFN-I. The experiment set-up was similar to "A" with additional treatments of Ara C to inhibit post-replicative protein synthesis (eGFP in WT MYXV is controlled by a synthetic early late promoter). M062 is expressed early and post-replicatively, and is packaged into the virion core. Thus it is highly likely that core M062 and M062 synthesized at the early time are responsible for the inhibition of DNA-mediated IFN-I.

DETAILED DESCRIPTION

Figure 1A:
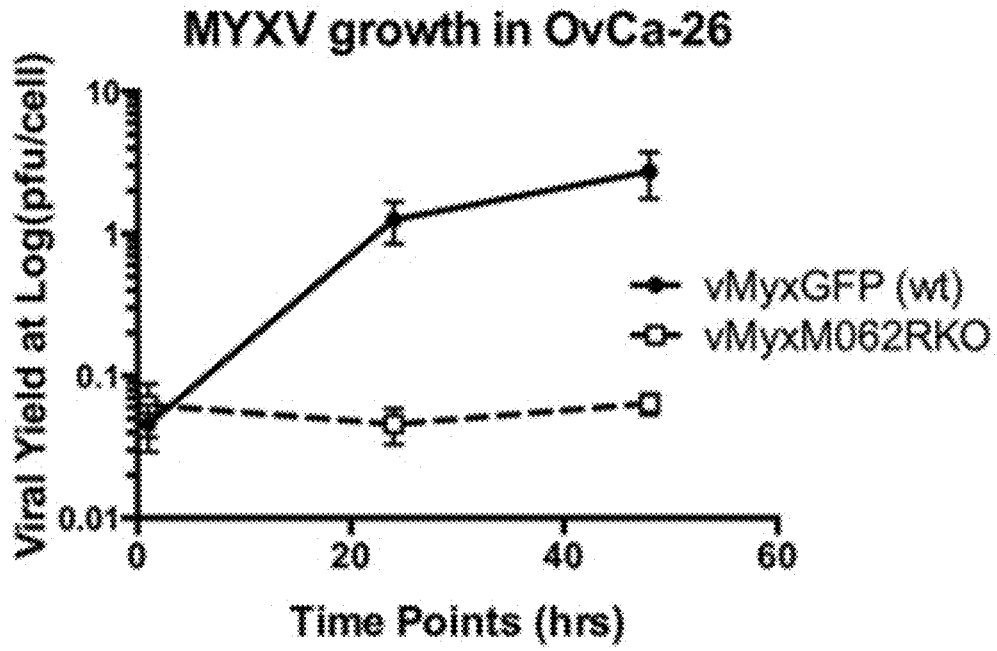

MYXV is an extremely attractive platform for immunotherapy. Wild type MYXV displays a tropism for human tumor cells, but, unlike vaccinia virus, it does not cause infection in healthy humans and therefore offers unparalleled safety. While MYXV infection targets both human tumor cells and disease macrophages in the tumor microenvironment, the wild type virus may also target companion animals such as rabbits leading to a complication with treating human subjects having such pets.

The present inventors discovered that a modified myxoma virus (MYXV) with a targeted deletion of the M062R gene therefore resulted in loss-of-function of M062 and can be used to treat various cancers as a monotherapy or in combination with other anti-cancer agents. Myxoma virus (MYXV) M062R is a functional homolog of the C7L family of host range genes from orthopoxviruses. The present inventors previously characterized the properties of a MYXV M062R loss-of-function mutant in vitro and in vivo and found that in many human cancer cells that are permissive for wild-type MYVX, the M062R mutant virus exhibited a profound replication defect. See Liu et al., *J. Virol.* 85(7):3270-3282 (2011). Because replication of MYXV was thought to be critical for the oncolytic activity of MYXV viruses, MYXV M062R loss-of-function viruses were not expected to possess potent oncolytic activities.

However, in the present application, the present inventors have discovered that MYXV-infection mediated tumor cell killing is in fact replication-independent and the mechanism is not necessarily the same as other oncolytic viruses that conduct lytic infection in cells. Thus, the inventors have demonstrated that MYXV M062R loss-of-function viruses nevertheless may be used as a potent oncolytic virotherapy to treat various types of cancer including, without limitation, ovarian and pancreatic cancers. Additionally, because MYXV M062R loss-of-function viruses exhibit significant replication defects, these viruses may alleviate concerns that such viruses would infect the companion animals of patients.

The present inventors further demonstrate that the combination of MYXV M062R loss-of-function viruses and other anti-cancer therapeutic agents can lead to improved treatment outcomes. Without being limited by theory, the present inventors conjecture that MYXV M062R loss-of-function viruses can be applied in combinations with other anti-cancer agents as a novel anticancer strategy because they not only can promote cytoreductive activity specifically against tumor cells but they also stimulate the innate immunity-mediating antitumor bystander effect and the adaptive immune response for a prolonged therapeutic effect. Moreover, treatment with MYXV M062R loss-of-function viruses can facilitate the elimination of the immunosuppressive environment that protects cancer cells from systemic immune surveillance. The present inventors have further demonstrated that MYXV M062R loss-of-function viruses are potent activators of an IFN-1 response even more so than the replication-competent wild type MYX. MYXV M062R loss-of-function viruses are able to prolong survival as a monotherapy especially when it is administered into a well-established immunosuppressive tumor environment. MYXV M062R loss-of-function viruses can also be effectively applied in combination with cisplatin or other cancer chemotherapeutics and significantly improves the treatment benefit of dendritic cell (DC) vaccines, which are often administered in combination with, and usually after treatment with, cisplatin.

Myxoma Viruses

In one aspect of the present invention, myxoma viruses are provided. The myxoma viruses may be either wild-type or mutant myxoma viruses. Myxoma virus (MYXV) is a poxvirus with a narrow host range in nature, infecting only rabbits. Wild type MYXV also displays a tropism for human tumor cells, and does not replicate productively in healthy human cells.

In some embodiments, the modified/mutant myxoma virus may be modified to eliminate or reduce as compared to a control myxoma virus the activity or expression of a Myxoma virus protein M062R (M62R). Myxoma virus protein M062R is an immunoregulatory protein in myxoma viruses. M062R gene is a functional homolog of the C7L family of host range genes from orthopoxviruses and is required for MYVX replication in most human cancer cells.

As used herein, the terms "protein" or "polypeptide" or "peptide" may be used interchangeably to refer to a polymer of amino acids. A "protein" as contemplated herein typically comprises a polymer of naturally occurring amino acids (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine).

The eliminated or reduced activity or expression of the Myxoma virus protein M062R is relative to a control myxoma virus. A "control myxoma virus" may be a wild-type myxoma virus that has not, for example, been modified as described herein. Exemplary control myxoma viruses are readily available in the art.

As used herein, the "activity" of the M062R protein refers to the ability of the protein to facilitate replication of a myxoma virus in a cancer cell. In some embodiments, the activity of the M062R protein is reduced by at least 30%, 40%, 50%, 55%, 60%, 65%, 70%, 75%, 80%, 85%, 90%, 95%, or 99% as compared to a control myxoma virus.

As used herein, the term "expression" may refer either to the levels of an RNA encoding a protein in a cell or the levels of the protein in a cell. In some embodiments, the expression of the M062R protein is reduced by at least 30%, 40%, 50%, 55%, 60%, 65%, 70%, 75%, 80%, 85%, 90%, 95%, or 99% as compared to a control myxoma virus.

As used herein, the terms "modified" or "modifying" refer to using any laboratory methods available to those of skill in the art including, without limitation, genetic engineering techniques (i.e. Recombinant DNA methodologies, CRISPR/Cas techniques, gene silencing technologies, etc.) or forward genetic techniques to affect the activity or expression of the M062R protein. It will be readily apparent to one of ordinary skill in the art that there a multiple potential ways to eliminate or reduce the activity or expression of the M062R protein by modifying the gene encoding the protein by, for example, introducing targeted mutations, by modifying a mRNA (or levels thereof) encoding the proteins using, for example, gene silencing techniques, or by inhibiting the M062R protein at the protein level.

The myxoma virus may also be modified to introduce a hypomorphic mutation or a null mutation in a polynucleotide (i.e., gene) encoding the M062R protein. A "null mutation" is an alteration in a gene that results in a gene that completely lacks its normal function. The complete lack of function may be the result of the complete absence of a gene product (i.e., protein or RNA) being produced in a cell or may result from the expression of a non-functional protein. Similarly, a "hypomorphic mutation" is an alteration in a gene that results in a gene that has reduced activity. The reduced activity may be from a reduced level of expression of gene products (i.e., protein or RNA) from the gene or may result from the expression of a gene product (i.e. protein or RNA) that has reduced activity.

It will be readily apparent to those of skill in the art that a variety of null or hypomorphic mutations may be introduced (using, for example, Recombinant DNA techniques, CRISPR/Cas or other genetic engineering techniques) into a polynucleotide encoding the M062R protein to arrive at embodiments of the present invention. For example, early stop codons may be introduced into the open reading frame of the gene encoding the M062R protein, which would result in the expression of a shorter protein sequence completely lacking or having reduced activity. Alternatively or additionally, a person of ordinary skill may introduce alterations (i.e., substitutions or deletions) into the promoter of a gene encoding the M062R protein that result in little or no expression of the M062R protein. Still further modifications contemplated herein include mutations that impact one or more of the domains of the M062R protein.

Combination Compositions

In another aspect, the present invention relates to compositions including a myxoma virus and an anti-cancer therapeutic agent, preferably the mutant myxoma virus and an anti-cancer therapeutic agent.

As used herein, an "anti-cancer therapeutic agent" may be any therapeutic agent that is used to treat cancer in a subject. Suitable anti-cancer therapeutic agents may include, without limitation, radiation, chemotherapy agents, anti-cancer biologics, immunotherapy agents and cancer vaccines. Chemotherapy agents are chemotherapeutic compounds that may be used to treat cancer. Suitable chemotherapy agents may include, without limitation, 5-fluorouracil, aclacinomycin, activated cytoxan, bisantrene, bleomycin, carmofur, CCNU, platinum based chemotherapy, such as cis-platinum (cisplatin), daunorubicin, doxorubicin, DTIC, melphalan, methotrexate, mithromycin, mitomycin, mitomycin C, peplomycin pipobroman, plicamycin, procarbazine, retinoic acid, tamoxifen, taxol, tegafur, VP16, or VM25. Chemotherapy agents may also include other small molecule anti-cancer therapeutics such as, without limitation, indoleatnine-pyrrole 2,3-dioxygenase (IDO) inhibitors. Anti-cancer therapeutic agent may be a targeted therapy, for example, a poly-ADP ribose polymerase (PARP) inhibitor. Other anti-cancer therapeutic agents include platinum-based therapeutics or nucleoside analogs such as gemcitabine.

Anti-cancer biologics are biomolecules (e.g., polynucleotides, polypeptides, lipids, or carbohydrates) that may be used to treat cancer. Anti-cancer biologics may include, without limitation, cytokines such as IL-1α, IL-2, IL-2β, IL-3, IL-4, CTLA-2, IFN-α, IFN-γ, granulocyte-macrophage colony stimulating factor (GM-CSF), IL-12, IL-23, IL-15, IL-7, IL-10 or any combination thereof; or anti-cancer antibodies such as, without limitation, Rituximab, Trastuzumab, Gemtuzumab, Alemtuzumab, Ibritumomab tiuxetan, Tositumomab, Cetuximab, Bevacizumab, Panitumumab, Ofatumumab, Brentuximab Vedotin, Pertuzumab, Adotrastuzumab emtansine, and Obinutuzumab.

The term "immunotherapy agent(s)" refers to any therapeutic that is used to treat cancer in a subject by inducing and/or enhancing an immune response in that subject. Immunotherapy agents may include, without limitation, checkpoint inhibitors, cancer vaccines, immune cells such as engineered T cells, anti-cancer viruses, or bispecific antibodies. Checkpoint inhibitors are therapeutics, such as antibodies, that block the immune checkpoint pathways in immune cells that are responsible for maintaining self-tolerance and modulating the degree of an immune response. Tumors often exploit certain immune checkpoint pathways as a major mechanism of immune resistance against T cells that are specific for tumor antigens. Many of the immune checkpoints are initiated by receptor-ligand interactions and thus may be blocked by antibodies to either the ligand or receptor or may be modulated by soluble recombinant forms of the ligands or receptors. Such immune checkpoint blockade allows tumor-specific T cells to continue to function in an otherwise immunosuppressive tumor microenvironment. Checkpoint inhibitors, however, are not effective against all cancer types. Furthermore, not every patient that is expected to respond to immune checkpoint blockade actually benefits from treatment with such agents. In part, the present inventors have found that treatment with MYXV M062R loss-of-function viruses can facilitate the elimination of the immunosuppressive environment that protects cancer cells from systemic immune surveillance and thus these viruses would be expected to work in synergy with checkpoint inhibitors to make tumors vulnerable to attack and elimination by the immune system. Thus, patients that do not respond to the administration of checkpoint inhibitors alone may benefit from administration of a checkpoint inhibitor(s) and MYXV viruses such as MYVX M062R loss-of-function viruses.

Exemplary checkpoint inhibitors include, without limitation, antibodies or other therapeutics targeting programmed cell death protein 1 (PD1, also known as CD279), programmed cell death 1 ligand 1 (PD-L1, also known as CD274), PD-L2, cytotoxic T-lymphocyte antigen 4 (CTLA4, also known as CD152), A2AR, CD27, CD28, CD40, CD80, CD86, CD122, CD137, OX40, GITR, ICOS, TIM-3, LAG3, B7-H3, B7-H4, BTLA, IDO, KIR, or VISTA. Suitable anti-PD1 antibodies include, without limitation, lambrolizumab (now pembrolizumab, Merck MK-3475, and described in U.S. Pat. Nos. 8,952,136, 8,354,5509, 8,900,587 and EP2170959), nivolumab (Bristol-Myers Squibb BMS-936558, and described in U.S. Pat. Nos. 7,595,048, 8,728,474, 9,073,994, 9,067,999, 8,008,449 and 8,779,105), AMP-224 (Merck), and pidilizumab (CureTech CT-011). Suitable anti-PD-L1 antibodies include, without limitation, MDX-1105 (Medarex), MEDI4736 (Medimmune) MPDL3280A (Genentech/Roche) and BMS-936559 (Bristol-Myers Squibb). Exemplary anti-CTLA4 antibodies include, without limitation, ipilimumab (Bristol-Myers Squibb, described in U.S. Pat. Nos. 7,605,238, 6,984,720, 5,811,097) and tremelimumab (Pfizer, described in U.S. Pat. No. 6,682,736 and EP Patent No. 1141028).

PARP inhibitors are known in the art. PARP1 is a protein that is important for repairing single-strand breaks ('nicks' in the DNA). If such nicks persist unrepaired until DNA is replicated (which must precede cell division), then the replication itself can cause double strand breaks to form, which if left unrepaired. Drugs that inhibit PARP1 cause multiple double strand breaks to form, and in tumors with BRCA1, BRCA2 or PALB2 mutations, these double strand breaks cannot be efficiently repaired, leading to the death of the cells. Suitable PARP inhibitors used in the methods as anti-cancer therapeutic agents include, but are not limited to, for example, olaparib (4-[(3[(4-cyclopropylcarbonyl)piperazin-1-yl]carbonyl)-4-fluorophenyl]methyl(2H)phthalazin-1-one, AstraZeneca Pharmaceuticals LP), rucaparib (8-Fluoro-2-{4-[(methylamino)methyl]phenyl}-1,3,4,5-tetrahydro-6H-azepino[5,4,3-cd]indol-6-one, Clovis Oncology of Boulder, CO.), niraparib (2-[4-[(3S)-3-Piperidyl]phenyl]indazole-7-carboxamide, Tesara), talazoparib ((8S,9R)-5-Fluoro-8-(4-fluorophenyl)-9-(1-methyl-1H-1,2,4-triazol-5-yl)-2,7,8,9-tetrahydro-3H-pyrido[4,3,2-de]phthalazin-3-one, Pfizer), veliparib (2-((R)-2-Methylpyrrolidin-2-yl)-1H-benzimidazole-4-carboxamide, AbbVie), BGB-290 (Pamiparib, found in WO 2013097225, Beigene), CEP 9722 (1-methoxy-2-((4-methylpiperazin-1-yl)methyl)-4,5,6,7-tetrahydro-1H-cyclopenta[a]pyrrolo[3,4-c]carbazole-1,3(2H)-dione, MedKoo), E7016 (10-((4-Hydroxypiperidin-1-yl)methyl)chromeno[4,3,2-de]phthalazin-3 (2H)-one, Eisai), 3-aminobenzamide, among others.

Cancer vaccines stimulate the body's immune system to attack cancer cells. Cancer vaccines generally include a tumor antigen in an immunogenic formulation that activates tumor antigen-specific helper T cells and/or cytotoxic T cells and B cells. Vaccines can be in a variety of formulations, including, without limitation, dendritic cells, monocytes, viral, liposomal and DNA vaccines. Suitably, the dendritic cells are autologous and transfected with tumor cells or tumor antigens. Dendritic cells are immune cells that present antigens to T cells, which prompted their application in therapeutic cancer vaccines. Following the loading of dendritic cells with tumor antigens ex vivo, the dendritic cells may be administered as a cellular vaccine which has been found to induce protective and therapeutic anti-tumor immunity.

In cancer types such as ovarian cancer in which cancer cells tend to evade the host immune responses due to the presence of regulatory T cells (Tregs), DC vaccines are useful. The Treg cells are CD4+ cells that cause anergy of Th1 and CD8+ tumor reactive cells. IL-17 producing CD4+ T cells (Th17) cells promote proinflammatory antigen specific immune responses and these responses are associated with a reduction in Tregs. DC vaccines are useful to induce Th17 cells and thus are helpful for treating ovarian cancer in particular. Exemplary cancer vaccines include those known in the art including, without limitation, the Th17-inducing dendritic cell (DC) vaccine described in the Examples or Sipuleucel-T (Provenge®, or APC8015). Sipuleucel-T is an FDA-approved cancer vaccine developed from autologous dendritic cells (DC) loaded with engineered fusion protein of prostatic acid phosphatase (PAP) and granulocyte-macrophage colony-stimulating factor (GM-CSF). TH17-inducing DC vaccine may SP17-loaded TH17 DC vaccine. A DC vaccine can be made ex vivo, by obtaining antigen-presenting dendritic cells from the patient or donor following a leukapheresis procedure and incubating the cells ex vivo in the presence of a tumor antigen (e.g. SP17, etc.) with cytokines to activate the DC (e.g., interleukin (IL)-1β, IL-6, tumor necrosis factor alpha (TNF-α), and PGE2, or granulocyte-macrophage colony-stimulating factor (GM_CSF, IL4, and TNF-α). For example, the antigen dendritic cells may be exposed to Sp17 protein and GM-CSF ex-vivo to activate the DCs. The activated DC cells are then returned to the patient to generate an immune response.

An immunotherapy agent may include immune cells (i.e., T cells or B cells) that are adoptively transferred into a subject to attack or reduce cancer cells or cancer cell growth. The immune cells may be autologous or derived from a subject that is different from the subject receiving the immune cells and modified to reduce rejection. The immune cells may also have a natural or genetically engineered reactivity to a subject's cancer. For example, natural autologous T cells have been shown to be effective in treating metastatic cancers. See, e.g., Rosenberg S A et al., *Nat. Rev. Cancer* 8 (4): 299-308 (2008). Natural autologous T cells may be found within a resected subject's tumor. Such T cells can be induced to multiply in vitro using high concentrations of IL-2, anti-CD3 and allo-reactive feeder cells. These T cells are then transferred back into the subject along with, for example, exogenous administration of IL-2 to further boost their anti-cancer activity.

The T cells may also include engineered T cells. Engineered T cells are T cells that have been genetically modified so as to direct T cells to specifically destroy a subject's cancer cells. Engineered T cells may, for example, include T cells that have been genetically modified to express chimeric antigen receptor (CAR) proteins or "CAR T cells." See, e.g., Liddy et al., *Nature Med.* 18:980-7 (2012); Grupp et al., *New England J. Med.* 368:1509-18, (2013). The CAR proteins may include a targeting moiety such as an extracellular single-chain variable fragment (scFv) capable of binding a tumor-associated antigen(s), a transmembrane domain, and intracellular signaling/activation domain(s). The intracellular signaling/activation domain(s) may include, without limitation, CD3ζ signaling domain, 41BB-signaling domains, CD28-signaling domains, or combinations thereof. Suitable tumor-associated antigens include, without limitation, CD19, carcinoembryonic antigen (CEA), diganglioside GD2, mesothelin, L1 cell adhesion molecule (L1CAM), human epidermal growth factor receptor 2 (HER2), fibroblast activation protein (FAP), interleukin 13 receptor α (IL13Rα), EGFR, or EGFR variant 3 (EGFRvIII).

CAR T cells have demonstrated remarkable success in treating blood-borne tumors such as certain kinds of leukemias. CAR T cells, however, have not been as effective at treating solid tumors, which present a number of unique barriers that are absent in blood-borne malignancies. For example, unlike the environment of blood-borne malignancies, CAR T cells must successfully traffic to solid tumor sites in spite of tumor signaling attempting to inhibit such trafficking. Furthermore, once trafficked to a tumor, CAR T cells must infiltrate into the solid tumor in order to elicit tumor-associated antigen-specific cytotoxicity. Even after successful trafficking and infiltration, CAR T cells must evade the immunosuppressive microenvironment of the tumor conferred by, for example, suppressive immune cells (regulatory T cells (Tregs), myeloid-derived suppressor cells (MDSC), tumor-associated macrophages (TAMs), and/or neutrophils (TAN). The present inventors have demonstrated that MYXV viruses such as MYVX M062R loss-of-function viruses may weaken the immunosuppressive microenvironment in tumors such as ovarian and pancreatic tumors. Given this ability to dampen the immunosuppressive microenvironment in tumors, the present inventors expect that T cell therapy such as CAR T cell therapy could be improved by also administering MYXV viruses such as MYVX M062R loss-of-function viruses.

An immunotherapy agent may include other oncolytic viruses besides MYVX viruses. As used herein, an "oncolytic virus" refers to any virus that may be used to treat cancer. Exemplary oncolytic viruses include, without limitation, PVS-RIPO, T-VEC, and Onyx-015. PVS-RIPO is a genetically modified oral poliovirus that has been fast-tracked by the FDA for the treatment of recurrent glioblastoma multiforme (GBM). T-VEC (Imlygic) is an FDA-approved oncolytic virus for the treatment of melanoma in patients with inoperable tumors. Onyx-015 is an oncolytic adenovirus.

Bispecific antibodies may also be used as an immunotherapy agent in accordance with the present invention. A bispecific antibody is an antibody having binding sites for a tumor-associated antigen and for a T-cell surface receptor that can direct the lysis of specific tumor cells by T cells. Bispecific antibodies have been used, for example, to successfully treat brain tumors in human patients. See, e.g., Nitta et al., *Lancet* 355:368-371 (1990). Numerous methods to produce bispecific antibodies are known in art including, without limitation, the quadroma method (See, e.g., Milstein and Cuello, *Nature,* 305:537-540 (1983)), use of heterobifunctional cross-linkers to chemically tether two different antibodies or antibody fragments (See, e.g., Staerz et al., *Nature* 314:628-631 (1985); European Patent Application 0453082), or DOCK-AND-LOCK methods (See, e.g., U.S. Pat. Nos. 7,550,143; 7,521,056; 7,534,866; 7,527,787 and 7,666,400).

A bispecific antibody may include a trifunctional antibody that includes two heavy and two light chains, one each from two different antibodies. The two Fab regions are directed against two antigens while the Fc region is made up from the two heavy chains and forms the third binding site, which typically may elicit effector functions. A bispecific antibody may include chemically linked Fab regions, various types of bivalent and trivalent single-chain variable fragments (scFvs), or fusion proteins mimicking the variable domains of two antibodies. Suitable bispecific antibodies include, without limitation, Removab (Trion Pharma), Blincyto (Amgen), AMG-110 (Amgen), ABT-122 (Abbvie), ABT-981 (Abbvie), AFM13 (Affimed Therapeutics), MM-111 (Merrimack Pharmaceuticals), SAR156597 (Sanofi), RG7221 (Roche), RG6013 (Roche), RG7597 (Roche), ALX-0761 (Ablynx), MCLA-128 (Merus), MEDI-565 (AMG-211), MGD006 (Macrogenics), and REGN1979 (Regeneron).

Pharmaceutical Compositions

In a further aspect, the present invention relates to pharmaceutical compositions including any one of the compositions described herein and a pharmaceutically acceptable carrier and/or an adjuvant.

The vaccine compositions may include a pharmaceutical carrier, excipient, or diluent, which are nontoxic to the cell or subject being exposed thereto at the dosages and concentrations employed. Often a pharmaceutical diluent is in an aqueous pH buffered solution. Examples of pharmaceutical carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ brand surfactant, polyethylene glycol (PEG), and PLURONICS™ surfactant.

The pharmaceutical compositions described herein may include adjuvants to increase immunogenicity of the composition. In some embodiments, these compositions comprise one or more of a mineral adjuvant, gel-based adjuvant, tensoactive agent, bacterial product, oil emulsion, particulated adjuvant, fusion protein, and lipopeptide. Mineral salt adjuvants include aluminum adjuvants, salts of calcium (e.g. calcium phosphate), iron and zirconium. Gel-based adjuvants include aluminum gel-based adjuvants and acemannan. Tensoactive agents include Quil A, saponin derived from an aqueous extract from the bark of *Quillaja saponaria*; saponins, tensoactive glycosides containing a hydrophobic nucleus of triterpenoid structure with carbohydrate chains linked to the nucleus, and QS-21. Bacterial products include cell wall peptidoglycan or lipopolysaccharide of Gram-negative bacteria (e.g. from *Mycobacterium* spp., *Corynebacterium parvum, C. granulosum, Bordetella pertussis* and *Neisseria meningitidis*), N-acetyl muramyl-L-alanyl-D-isoglutamine (MDP), different compounds derived from MDP (e.g. threonyl-MDP), lipopolysaccharides (LPS) (e.g. from the cell wall of Gram-negative bacteria), trehalose dimycolate (TDM), cholera toxin or other bacterial toxins, and DNA containing CpG motifs. Oil emulsions include FIA, Montanide, Adjuvant 65, Lipovant, the montanide family of oil-based adjuvants, and various liposomes. Among particulated and polymeric systems, poly (DL-lactide-coglycolide) microspheres have been extensively studied and find use herein. Notably, several of the delivery particles noted above may also act as adjuvants.

In some embodiments, the pharmaceutical compositions further include cytokines (e.g. IFN-γ, granulocyte-macrophage colony stimulating factor (GM-CSF) IL-2, or IL-12) or immunostimulatory molecules such as FasL, CD40 ligand or a toll-like receptor agonist, or carbohydrate adjuvants (e.g. inulin-derived adjuvants, such as, gamma inulin, algammulin, and polysaccharides based on glucose and mannose, such as glucans, dextrans, lentinans, glucomannans and galactomannans). In some embodiments, adjuvant formulations are useful in the present invention and include alum salts in combination with other adjuvants such as Lipid A, algammulin, immunostimulatory complexes (ISCOMS), which are virus like particles of 30-40 nm and dodecahedric structure, composed of Quil A, lipids, and cholesterol.

In some embodiments, the additional adjuvants are described in Jennings et al. Adjuvants and Delivery Systems for Viral Vaccines-Mechanisms and Potential. In: Brown F, Haaheim L R, (eds). Modulation of the Immune Response to Vaccine Antigens. Dev. Biol. Stand, Vol. 92. Basel: Karger 1998; 19-28 and/or Sayers et al. J Biomed Biotechnol. 2012; 2012: 831486, and/or Petrovsky and Aguilar, Immunology and Cell Biology (2004) 82, 488-496.

In some embodiments, the adjuvant is an aluminum gel or salt, such as aluminum hydroxide, aluminum phosphate, and potassium aluminum sulfate, AS04 (which is composed of aluminum salt and MPL), and ALHYDROGEL. In some embodiments, the aluminum gel or salt is a formulation or mixture with any of the additional adjuvants described herein.

In some embodiments, pharmaceutical compositions include oil-in-water emulsion formulations, saponin adjuvants, ovalbumin, Freunds Adjuvant, cytokines, and/or chitosans. Illustrative compositions comprise one or more of the following.

(1) ovalbumin (e.g. ENDOFIT);

(2) oil-in-water emulsion formulations, with or without other specific immunostimulating agents, such as: (a) MF59 (PCT Publ. No. WO 90/14837), which may contain 5% Squalene, 0.5% Tween 80, and 0.5% Span 85 (optionally containing various amounts of MTP-PE) formulated into submicron particles, (b) SAF, containing 10% Squalane, 0.4% Tween 80, 5% pluronic-blocked polymer L121, and thr-MDP either microfluidized into a submicron emulsion or vortexed to generate a larger particle size emulsion, (c) RIBI adjuvant system (RAS), (RIBI IMMUNOCHEM, Hamilton, MO.) containing 2% Squalene, 0.2% Tween 80, and, optionally, one or more bacterial cell wall components from the group of monophosphorylipid A (MPL), trehalose dimycolate (TDM), and cell wall skeleton (CWS), including MPL+CWS (DETOX™); and (d) ADDAVAX (Invitrogen);

(3) saponin adjuvants, such as STIMULON (Cambridge Bioscience, Worcester, Mass.);

(4) Complete Freunds Adjuvant (CFA) and Incomplete Freunds Adjuvant (IFA);

(5) cytokines, such as interleukins (by way of non-limiting example, IL-1, IL-2, IL-4, IL-5, IL-6, IL-7, IL-12, etc.), interferons (e.g., gamma interferon), macrophage colony stimulating factor (M-CSF), tumor necrosis factor (TNF), etc;

(6) chitosans and other derivatives of chitin or poly-N-acetyl-D-glucosamine in which the greater proportion of the N-acetyl groups have been removed through hydrolysis; and (7) other substances that act as immunostimulating agents to enhance the effectiveness of the composition, e.g., monophosphoryl lipid A.

In other embodiments, adjuvants include a flagellin-based agent, an aluminium salt or gel, a pattern recognition receptors (PRR) agonist, CpG ODNs and imidazoquinolines. In some embodiments, adjuvants include a TLR agonist (e.g. TLR1, and/or TLR2, and/or TLR3, and/or TLR4, and/or TLR5, and/or TLR6, and/or TLR7, and/or TLR8, and/or TLR9, and/or TLR10, and/or TLR11, and/or TLR12, and/or TLR13), a nucleotide-binding oligomerization domain (NOD) agonist, a stimulator of interferon genes (STING) ligand, or related agent.

Kits

In another aspect, the present invention relates to kits. The kits may include a myxoma virus, such as any of the myxoma viruses described herein, and an anti-cancer therapeutic agent. Optionally, the kits may further include the components required to perform any of the methods disclosed herein.

Methods of Treating Cancer

In a still further aspect of the present invention, methods of treating cancer in a subject are provided. The methods may include administering a therapeutically effective amount of any of the compositions described herein to the subject. Alternatively, the methods may include administering to the subject a therapeutically effective amount of any one of the myxoma viruses described herein, and administering to the subject a therapeutically effective amount of an anti-cancer therapeutic agent. The methods may also include administering to the subject a therapeutically effective amount of a first anti-cancer therapeutic agent, administering to the subject a therapeutically effective amount of any one of the myxoma viruses described herein, and administering to the subject a therapeutically effective amount of a second anti-cancer therapeutic agent. The first and second anti-cancer therapeutic agents may be the same agent or different agents.

As used herein, the "subject" may be any mammal, suitably a human, or domesticated animal such as a dog, cat, horse, cow, pig, or a mouse or rat.

Exemplary "cancers" in accordance with the present invention include, without limitation, ovarian, primary and metastatic breast, lymphoma, myeloma, pancreatic, prostate, bladder, lung, osteosarcoma, pancreatic, gastric, esophageal, colon, skin cancers (basal and squamous carcinoma; melanoma), testicular, colorectal, urothelial, renal cell, hepatocellular, leukemia, and central nervous system cancers or pre-cancers.

Treating cancer includes, without limitation, reducing the number of cancer cells or the size of a tumor in the subject, reducing progression of a cancer to a more aggressive form (i.e. maintaining the cancer in a form that is susceptible to a therapeutic agent), reducing proliferation of cancer cells or reducing the speed of tumor growth, killing of cancer cells, reducing metastasis of cancer cells or reducing the likelihood of recurrence of a cancer in a subject. Treating a subject as used herein refers to any type of treatment that imparts a benefit to a subject afflicted with cancer or at risk of developing cancer or facing a cancer recurrence. Treatment includes improvement in the condition of the subject (e.g., in one or more symptoms), delay in the progression of the disease, delay in the onset of symptoms or slowing the progression of symptoms, etc.

An "effective amount" or a "therapeutically effective amount" as used herein means the amount of a composition that, when administered to a subject for treating a state, disorder or condition is sufficient to effect a treatment (as defined above). The therapeutically effective amount will vary depending on the compound, formulation or composition, the disease and its severity and the age, weight, physical condition and responsiveness of the subject to be treated.

The compositions and pharmaceutical compositions described herein may be administered by any means known to those skilled in the art, including, without limitation, intravenously, intra-tumoral, intra-lesional, intradermal, topical, intraperitoneal, intramuscular, parenteral, subcutaneous and topical administration. Thus the compositions may be formulated as an injectable, topical or ingestible, suppository formulation. Administration of the compositions and pharmaceutical compositions to a subject in accordance with the present invention may exhibit beneficial effects in a dose-dependent manner. Thus, within broad limits, administration of larger quantities of the compositions is expected to achieve increased beneficial biological effects than administration of a smaller amount. Moreover, efficacy is also contemplated at dosages below the level at which toxicity is seen.

It will be appreciated that the specific dosage of a myxoma virus and/or anti-cancer therapeutic agent administered in any given case will be adjusted in accordance with the composition or compositions being administered, the volume of the composition that can be effectively delivered to the site of administration, the disease to be treated or inhibited, the condition of the subject, and other relevant medical factors that may modify the activity of the compositions or the response of the subject, as is well known by those skilled in the art. For example, the specific dose of a myxoma virus and/or anti-cancer therapeutic agent for a particular subject depends on age, body weight, general state of health, diet, the timing and mode of administration, the rate of excretion, medicaments used in combination and the severity of the particular disorder to which the therapy is applied. Dosages for a given patient can be determined using conventional considerations, e.g., by customary comparison of the differential activities of the compositions described herein and of a known agent, such as by means of an appropriate conventional pharmacological protocol. The compositions can be given in a single dose schedule, or in a multiple dose schedule.

The maximal dosage of a myxoma virus and/or anti-cancer therapeutic agent for a subject is the highest dosage that does not cause undesirable or intolerable side effects. The number of variables in regard to an individual treatment regimen is large, and a considerable range of doses is expected. The route of administration will also impact the dosage requirements. It is anticipated that dosages of the compositions will treat cancer by, for example, by reducing tumor size or decreasing the rate of tumor growth by least 10%, 20%, 30%, 40%, 50%, 60%, 70%, 80%, 90%, 100% or more as compared to no treatment.

The effective dosage amounts of a myxoma and/or anti-cancer therapeutic agent herein refer to total amounts administered, that is, if more than one composition is administered, the effective dosage amounts of a myxoma and/or anti-cancer therapeutic agent corresponds to the total amount administered. The compositions can be administered as a single dose or as divided doses. For example, the composition may be administered two or more times separated by 4 hours, 6 hours, 8 hours, 12 hours, a day, two days, three days, four days, one week, two weeks, or by three or more weeks.

The compositions and pharmaceutical compositions described herein may be administered one time or more than one time to the subject to effectively treat cancer.

The effectiveness of an anti-cancer therapeutic agent may be enhanced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% when combined with a myxoma virus and relative to a control treated with the anti-cancer therapeutic agent alone. Suitably, the compositions and methods described herein may reduce the size of a tumor or the spread of a tumor in a subject by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 99% relative to a control such as saline or relative to administration of the anti-cancer therapeutic agent alone.

The myxoma virus may be administered before, after, or concurrently with the anti-cancer therapeutic agent. In some embodiments, the myxoma virus is administered at least 6 hours, 12 hours, 18 hours, 1 day, 2 days, 3 days, 4 days, 5 days, or more prior to the anti-cancer therapeutic agent. In some embodiments, the anti-cancer therapeutic agent is administered at least 6 hours, 12 hours, 18 hours, 1 day, 2 days, 3 days, 4 days, 5 days, or more prior to the myxoma virus.

In some embodiments, the methods may include treating cancer in a human subject including: administering to the human subject a therapeutically effective amount of cisplatin, gemcitabine or another anti-cancer therapeutic agent, such as a platinum-based therapeutic or a nucleoside analog, to the human subject, and administering to the human subject a therapeutically effective amount of a myxoma virus, the myxoma virus suitably modified to eliminate or reduce as compared to a control myxoma virus the activity or expression of a Myxoma virus protein M062. Suitably, the myxoma virus is administered after the therapeutic agent. The timing for virus administration may be at least 6 hours, 12 hours, 18 hours, 1 day, 2 days, 3 days, 4 days, 5 days, or more after the chemotherapeutic agent.

In some embodiments, the methods may include treating cancer in a human subject including administering to the human subject a therapeutically effective amount of a myxoma virus, the myxoma virus suitably modified to eliminate or reduce as compared to a control myxoma virus the activity or expression of a Myxoma virus protein M062, and administering to the human subject a therapeutically effective amount of a dendritic cell (DC) cancer vaccine to the human subject. Suitably, the myxoma virus is administered before the cancer vaccine. The myxoma virus may be administered at least 6 hours, 12 hours, 18 hours, 1 day, 2 days, 3 days, 4 days, 5 days, or more before the dendritic cell (DC) cancer vaccine.

In some embodiments, the methods may include treating cancer in a human subject including: administering to the human subject a therapeutically effective amount of anti-cancer therapy (for example, a platinum based chemotherapy, such as cisplatin) to the human subject, administering to the human subject a therapeutically effective amount of a myxoma virus, the myxoma virus modified to eliminate or reduce as compared to a control myxoma virus the activity or expression of a Myxoma virus protein M062, and administering to the human subject a therapeutically effective amount of a dendritic cell (DC) cancer vaccine to the human subject. The myxoma virus may be administered at least 6 hours, 12 hours, 18 hours, 1 day, 2 days, 3 days, 4 days, 5 days, or more after the chemotherapeutic agent, and the virus may be administered at least 6 hours, 12 hours, 18 hours, 1 day, 2 days, 3 days, 4 days, 5 days, or more before the dendritic cell (DC) cancer vaccine.

In some embodiments, methods of eliciting an interferon response in a subject having cancer are provided. The methods comprise administering to the subject a therapeutically effective amount of mutant myxoma virus modified to eliminate or reduce the activity or expression of myxoma virus protein M62 as compared to a control myxoma virus to elicit an interferon response in the subject. In some embodiments, the interferon response comprises an increase in IFN-β and IFN-I in a subject. In some embodiments, the cancer subject has been treated with an anti-cancer therapeutic agent or a cancer vaccine prior to administering the mutant myxovirus. For example, in some instances, the cancer subject is first treated with an anti-cancer therapy, for example, a chemotherapy before administration of the mutant myxoma virus. In some examples, the anti-cancer therapeutic agent is a chemotherapeutic agent, PARP inhibitor or checkpoint inhibitor. In some examples, the subject is subsequently administered a DC vaccine after eliciting the interferon response in order to increase the anti-tumor effect.

In another embodiment, methods of inhibiting, reducing or eliminating a CD14+ tumor associated macrophage (TAM) inhibition of CD4+ T cells in a subject having cancer are provided. The method comprises administering a therapeutically effective amount of mutant myxoma virus modified to eliminate or reduce the activity or expression of myxoma virus protein M62R as compared to a control myxoma virus to increase the CD4+ T cell response in a subject. Not to be bound by any theory, but as demonstrated in the Examples below, the administration of mutant myxoma virus enhanced the CD4+ T cell response by reducing the TAM's ability to create an immunosuppressive tumor microenvironment. In some examples, the cancer subject has been treated with an anticancer agent prior to inhibiting, reducing or prior to administering the mutant myxoma virus. In other examples, the cancer subject is subsequently treated with an anti-cancer therapeutic agent after enhancement of the CD4+ T cell response.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference in their entirety, unless explicitly indicated otherwise. The present disclosure shall control in the event there are any disparities between any definitions and/or description found in the cited references.

Unless otherwise specified or indicated by context, the terms "a", "an", and "the" mean "one or more." For example, "a protein" or "an RNA" should be interpreted to mean "one or more proteins" or "one or more RNAs," respectively.

EXAMPLES

The following examples are meant only to be illustrative and are not meant as limitations on the scope of the invention or of the included claims.

Example 1: Myxoma Virus Optimizes Cisplatin for the Treatment of Ovarian Cancer In Vitro and in a Syngeneic Murine Dissemination Model A therapeutic approach to improve treatment outcome of ovarian cancer (OC) in patients is urgently needed. Myxoma virus (MYXV) is a candidate oncolytic virus that infects to eliminate OC cells. We found that in vitro MYXV treatment enhances cisplatin or gemcitabine treatment by allowing lower doses than the corresponding $IC_{50}$ calculated for primary OC cells. MYXV also affected OC patient ascites-associated CD14$^+$ myeloid cells, one of the most abundant immunological components of the OC tumor environment; without causing cell death, MYXV infection reduces the ability of these cells to secrete cytokines such as IL-10 that are signatures of the immunosuppressive tumor environment. We found that pretreatment with replication-competent but not replication-defective MYXV-sensitized tumor cells to later cisplatin treatments to drastically improve survival in a murine syngeneic OC dissemination model. We thus conclude that infection with replication-competent MYXV before cisplatin treatment markedly enhances the therapeutic benefit of chemotherapy. Treatment with replication-competent MYXV followed by cisplatin potentiated splenocyte activation and IFNγ expression, possibly by T cells, when splenocytes from treated mice were stimulated with tumor cell antigen ex vivo. The impact on immune responses in the tumor environment may thus contribute to the enhanced antitumor activity of combinatorial MYXV-cisplatin treatment.

Prolonging survival and preventing relapse for ovarian cancer (OC) patients remain challenging, despite the availability of appropriate surgery and highly effective first-line chemotherapy.[1] It is estimated that 70% of patients with advanced OC eventually relapse in spite of remission achieved after initial treatment.[1,2] Developing novel treatment approaches is urgently needed.

Immune response and especially immune status within the tumor environment play critical roles in OC progression, overall prognosis, and survival.[3,4] The presence of tumor-infiltrating lymphocytes is associated with prolonged survival.[3] Tumor cells, however, cultivate the tumor environment to impair antitumor immunity, an activity that has been associated with poor survival and prognosis;[5] this immunosuppressive tumor environment is also a major obstacle for effective treatments of OC, including dendritic cell vaccination.[6] Thus, an integrated treatment strategy that not only complements current chemotherapy but also alleviates immune suppression in the tumor environment could benefit the treatment of patients with OC.

Oncolytic virotherapy can be applied as a novel anticancer strategy because it not only can promote cytoreductive activity specifically against tumor cells[7,8] but also stimulates the innate immunity-mediating antitumor bystander effect[9] and the adaptive immune response for a prolonged therapeutic effect.[10,11] The mechanism by which a long-lasting treatment benefit is triggered depends on the virus used. In general, oncolytic virotherapy has a direct cytolytic effect on cancer cells, resulting in the release of tumor antigens that leads to a cascade of events ultimately inducing antitumoral adaptive immunity. This outcome is especially valuable in the elimination of micrometastases in distant locations. Moreover, oncolytic virotherapy can facilitate the elimination of the immunosuppressive environment that protects cancer cells from systemic immune surveillance.[12] The immunotherapeutic value of oncolytic virotherapy is gradually being recognized.[13]

The combination of oncolytic virotherapy and cytotoxic chemotherapy agents for improved treatment outcomes has been proposed.[14] The synergistic effect observed through this combination treatment may be due to an escalated induction of systemic antitumor immunity.[15] Myxoma virus (MYXV) is a candidate oncolytic virus on the path to clinical usage[16] and possesses immunogenic properties.[17,18] Although in vitro MYXV oncolytic potential has been evaluated that can effectively infect and kill patient ascites-derived OC cells grown in monolayer[19] (FIGS. 1B and 1D), other than three-dimensional spheroids,[20] it has not been investigated in the animal model.

The combination of MYXV and gemcitabine tested in a pancreatic tumor model showed a significant treatment benefit.[21] Based on the findings in this study, the use of MYXV to treat tumor dissemination within the peritoneal space shows promise. Moreover, in the pancreatic syngeneic model tested in this earlier study, an immunosuppressive tumor environment is present,[22,23] which shares similarity to the immunological property of the OC environment. Because gemcitabine is a second-line chemotherapy option for OC, we considered it as one treatment option in our OC model as a control.

In this study, we focused on using the combination of MYXV and cisplatin to treat disseminated OC associated with an immunosuppressive tumor microenvironment. Cisplatin, an alkylating agent that causes DNA damage and subsequent apoptosis,[24] is a first-line platinum-based chemotherapy agent against OC. Cisplatin has also been observed to impact host immune response by reducing regulatory T cells while enhancing antigen-specific CD8$^+$ T cell activities.[25] When cisplatin and oncolytic virotherapy are used together to achieve therapeutic benefit, however, the immunological impact differs, and specific characterization of the mechanism involved is needed.[26,27] Our study marks a first attempt to utilize MYXV and cisplatin together to treat disseminated OC in vivo. We show that combinatorial MYXV/cisplatin produced a significant improvement in overall survival in a mouse model of this deadly cancer.

Results

MYXV Oncolytic Potential Against OC Cells

Figure 1B:
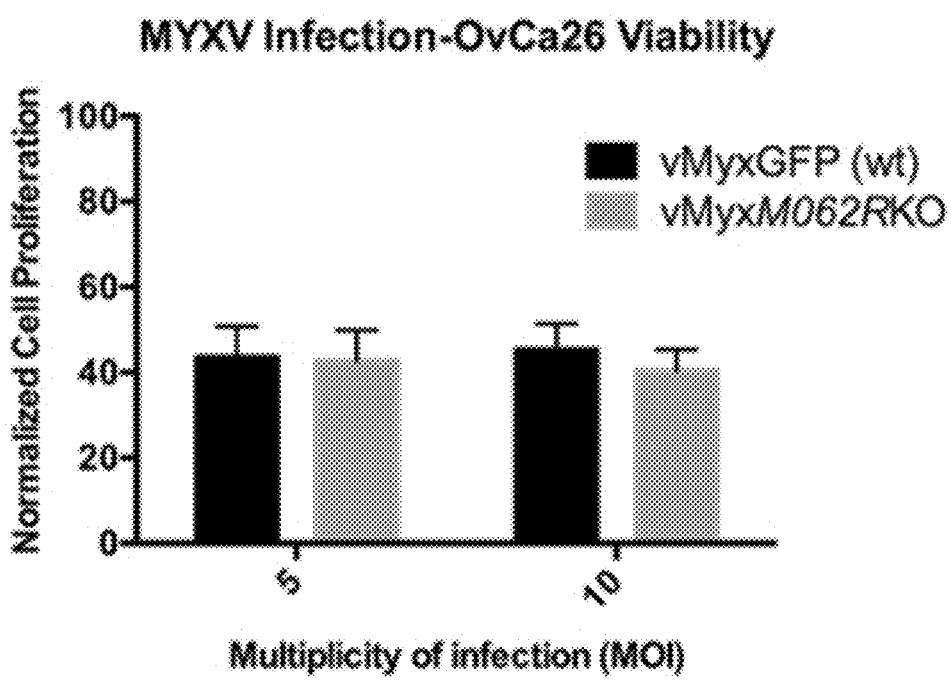
Figure 1C:
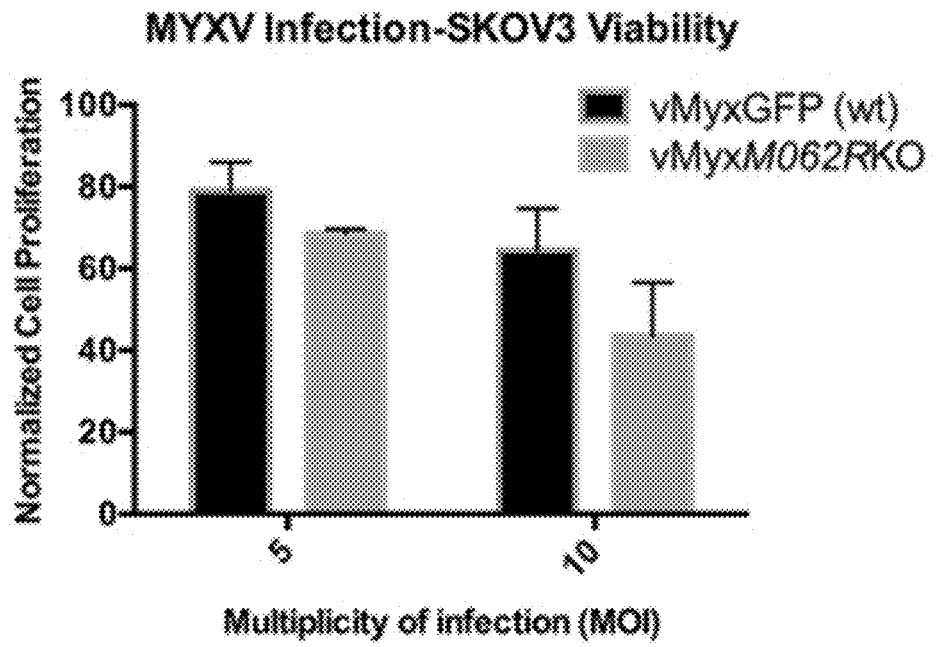
Figure 1D:
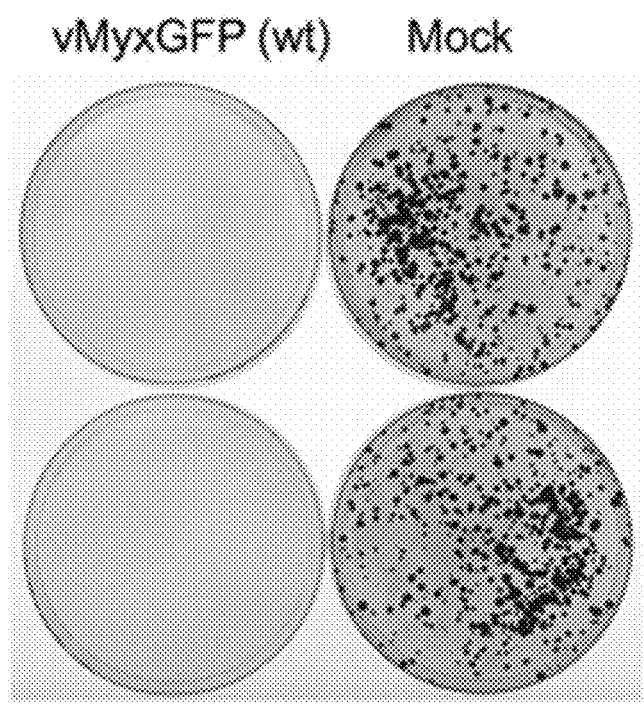
Figure 2A:
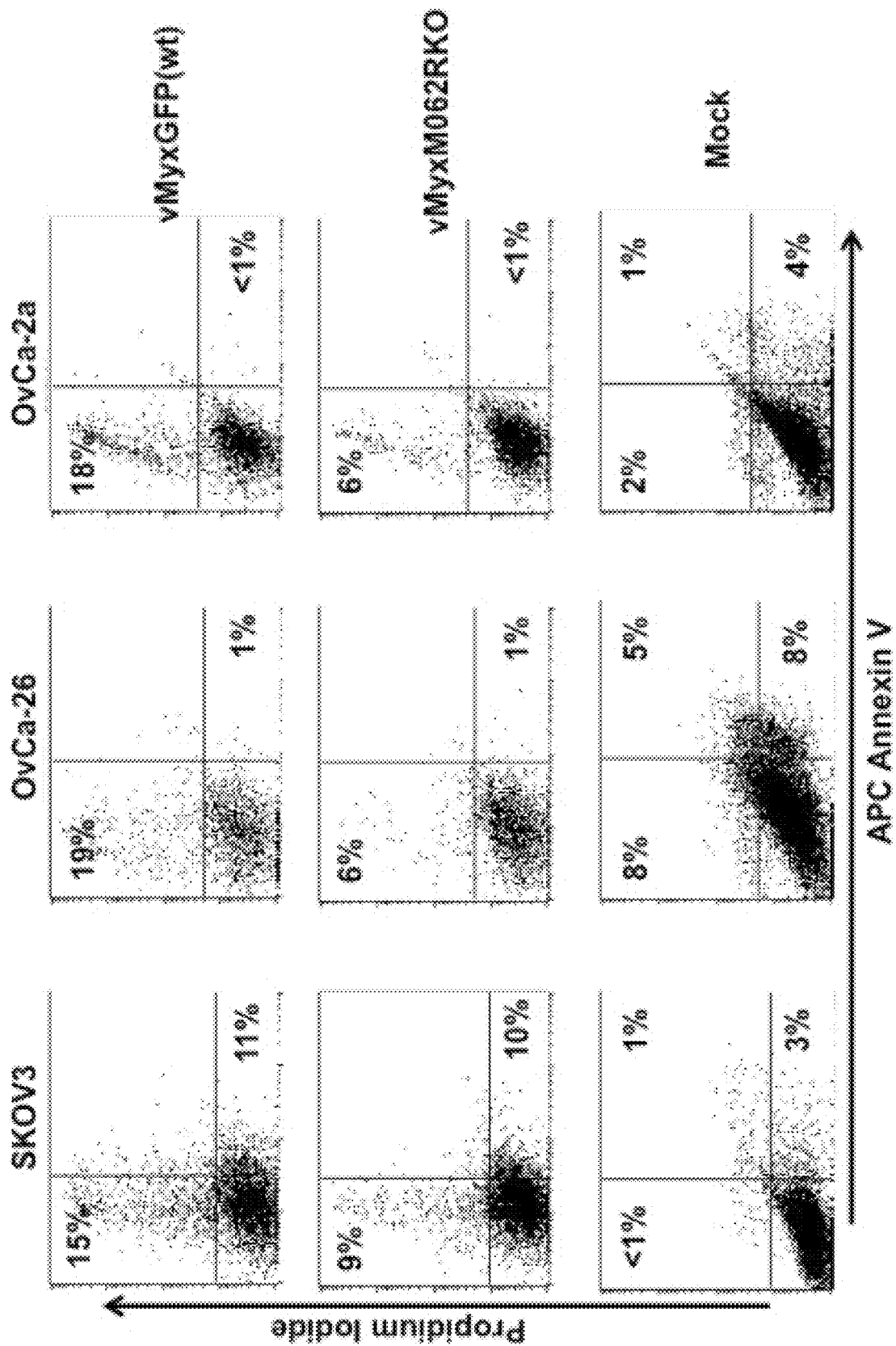
Figure 2B:
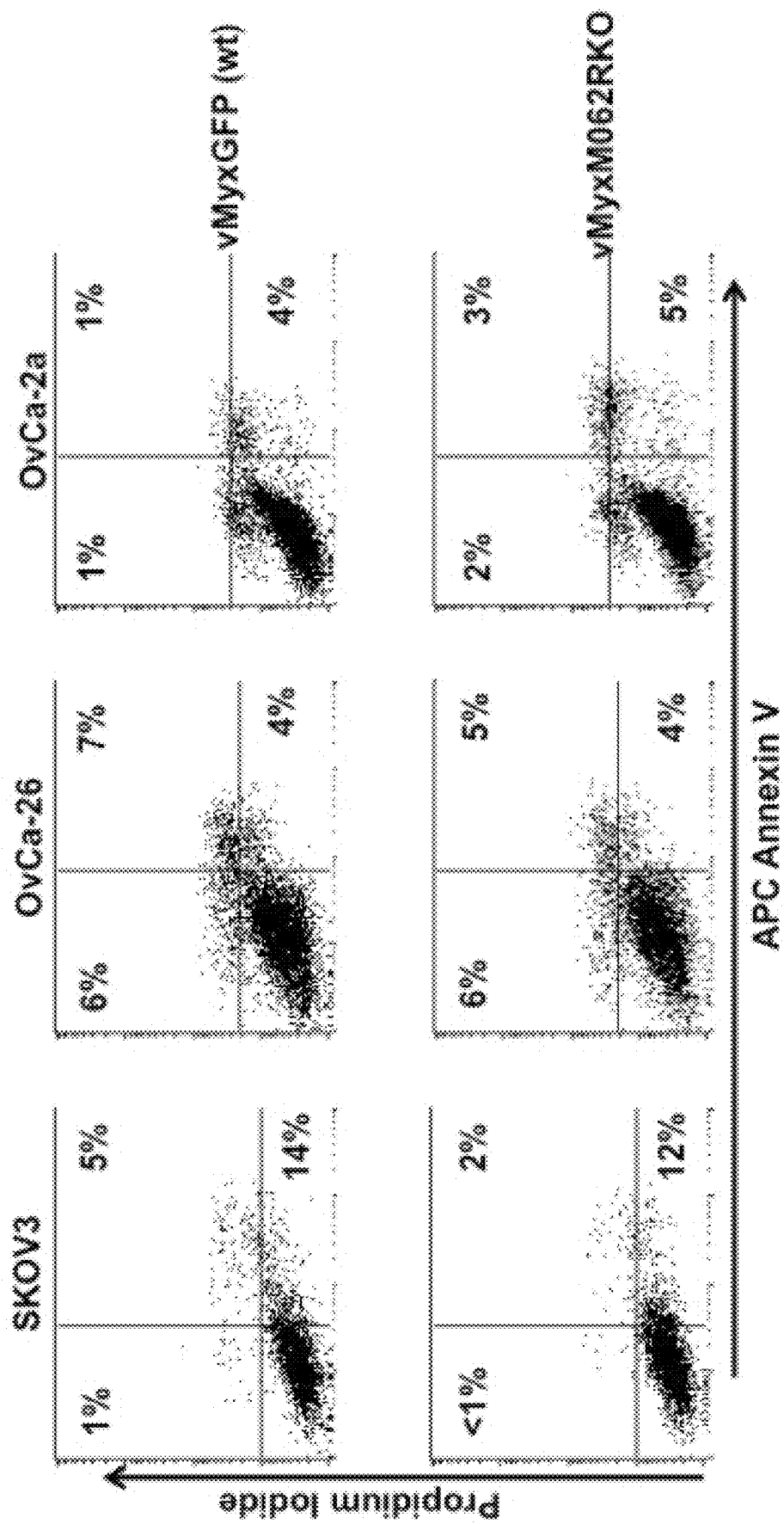

We evaluated the oncolytic potential of MYXV in the established OC cell line SKOV3 and in two primary OC cell lines, OvCa-2a and OvCa-26, that were developed from patient ascites. Wild-type (WT) MYXV (vMyxGFP) could productively infect the cells, while a mutant virus lacking the replication-essential gene M062R (M062R-null MYXV or vMyxM062RKO) caused abortive infection in all OC cell lines tested (FIG. 1A). Interestingly, however, infection by either mutant (M062R-null MYXV) or WT MYXV caused comparable reductions in cell viability as measured by MTT assay (FIGS. 1B and 1C). In patient ascites-derived OC cells, MYXV infection-associated reduction in viability is much more evident than that in the established cell line, SKOV3 (FIGS. 1B and 1C, respectively). Infection of SKOV3 cells with MYXV led to loss of the ability to form colonies (FIG. 1D); comparable effects by MYXV were also seen in the two primary OC cell lines (data not shown). Cell death associated with MYXV infection in the two primary OC cell lines did not show a signature of apoptosis (FIGS. 2A-2B). WT MYXV infection in OvCa-2a and OvCa-26 caused a moderate increase of cell death in infected cells that was not seen in replication-defective infection (GFP+; FIG. 2A). On the other hand, MYXV infection of SKOV3 cells caused a slight increase in the number of cells positive for early signs of apoptosis; however, this effect was replication independent (FIGS. 2A-2B).

MYXV Treatment as a Complement to Chemotherapy Drugs In Vitro

Figure 3A:
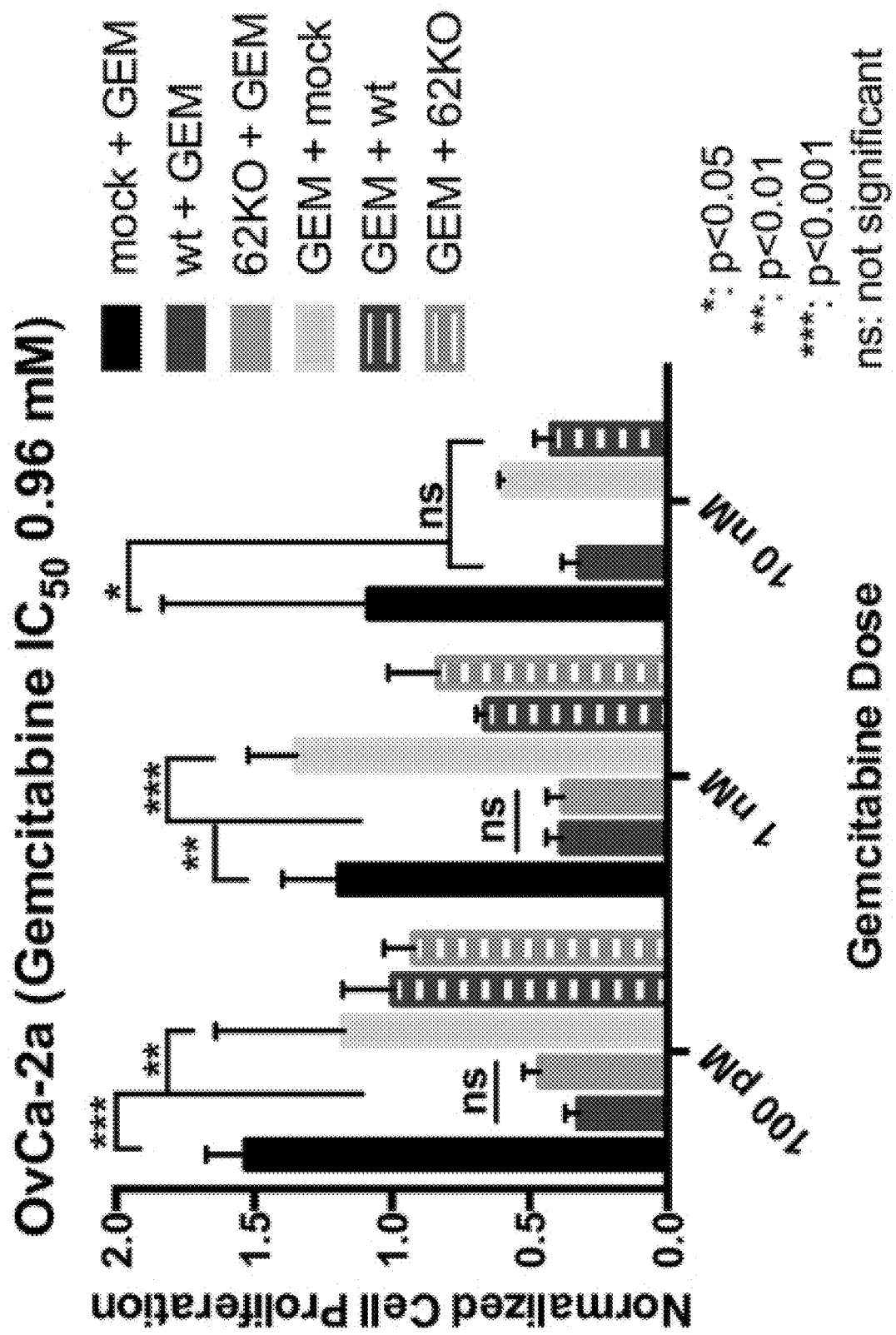
Figure 3B:
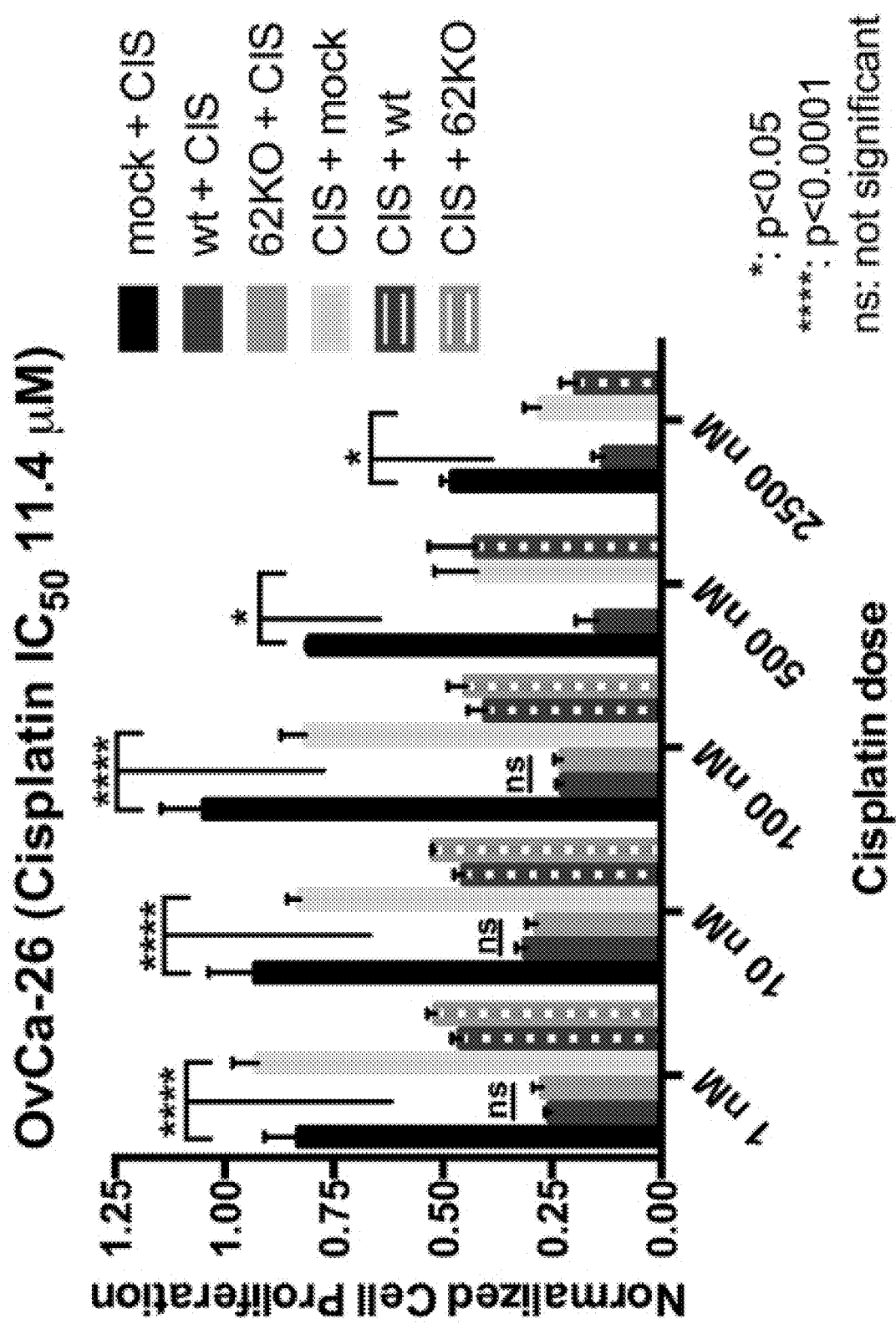
Figure 7A:
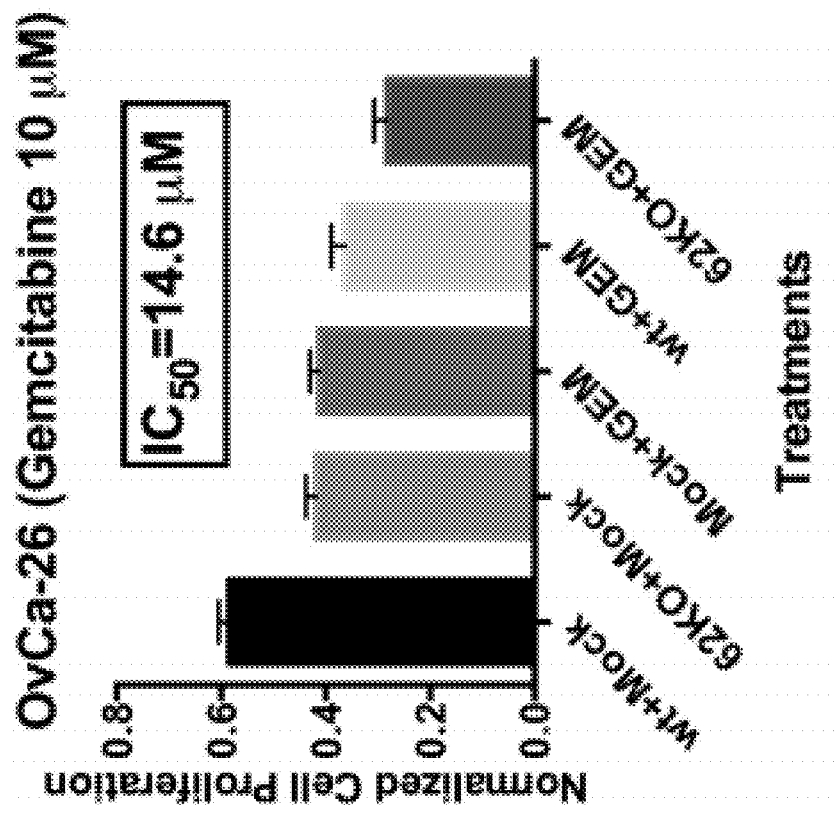
Figure 7B:
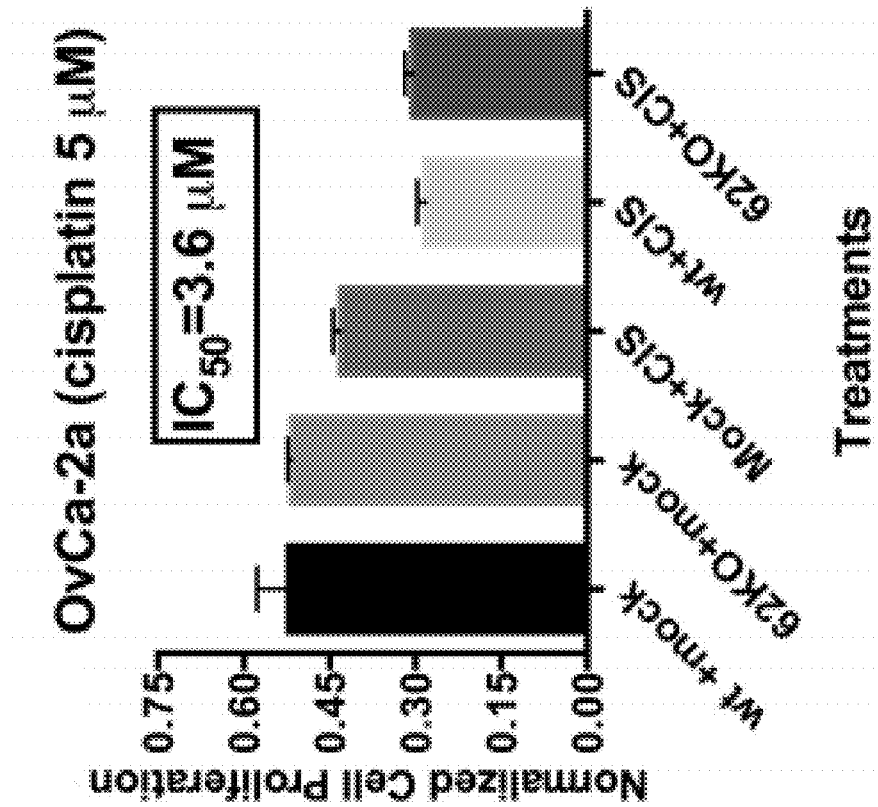

We tested the sensitivity of OvCa-2a and OvCa-26 to cisplatin in comparison to SKOV3 and found OvCa-26 (calculated IC50=11.4 µM) to be slightly more resistant than OvCa-2a (calculated IC50=3.6 µM) and SKOV3 (8.4 µM). We thus focused on OvCa-26 for further testing on cisplatin response. We also found OvCa-2a (calculated IC50=0.96 mM) to be relatively resistant to the gemcitabine treatment compared with SKOV3 (IC50=9.32 µM) and OvCa-26 (14.6 µM) and chose to focus on OvCa-2a for further testing related to gemcitabine. At doses comparable to IC50, additive effects of drug and virus were observed in primary OC cells (FIGS. 7A-7B). When we treated primary OC cells with cisplatin or gemcitabine at doses much lower than their calculated IC50, we did not observe significant growth inhibition with drug treatment alone (FIGS. 3A-3B); the reduced cell viability in groups treated with the MYXV treatment following cisplatin or gemcitabine is caused by MYXV infection (FIGS. 1B and 3B). When we evaluated the effects of combinatorial treatment with MYXV followed by chemotherapy (cisplatin or gemcitabine), consistent and significant further reductions in cell viability could be detected compared with the treatment outcomes of drug first followed by MYXV (FIGS. 3A-3B) or MYXV alone (FIG. 1B).

MYXV Infection in OC Patient Ascites-Associated CD14+ Monocytes

Figure 4A:
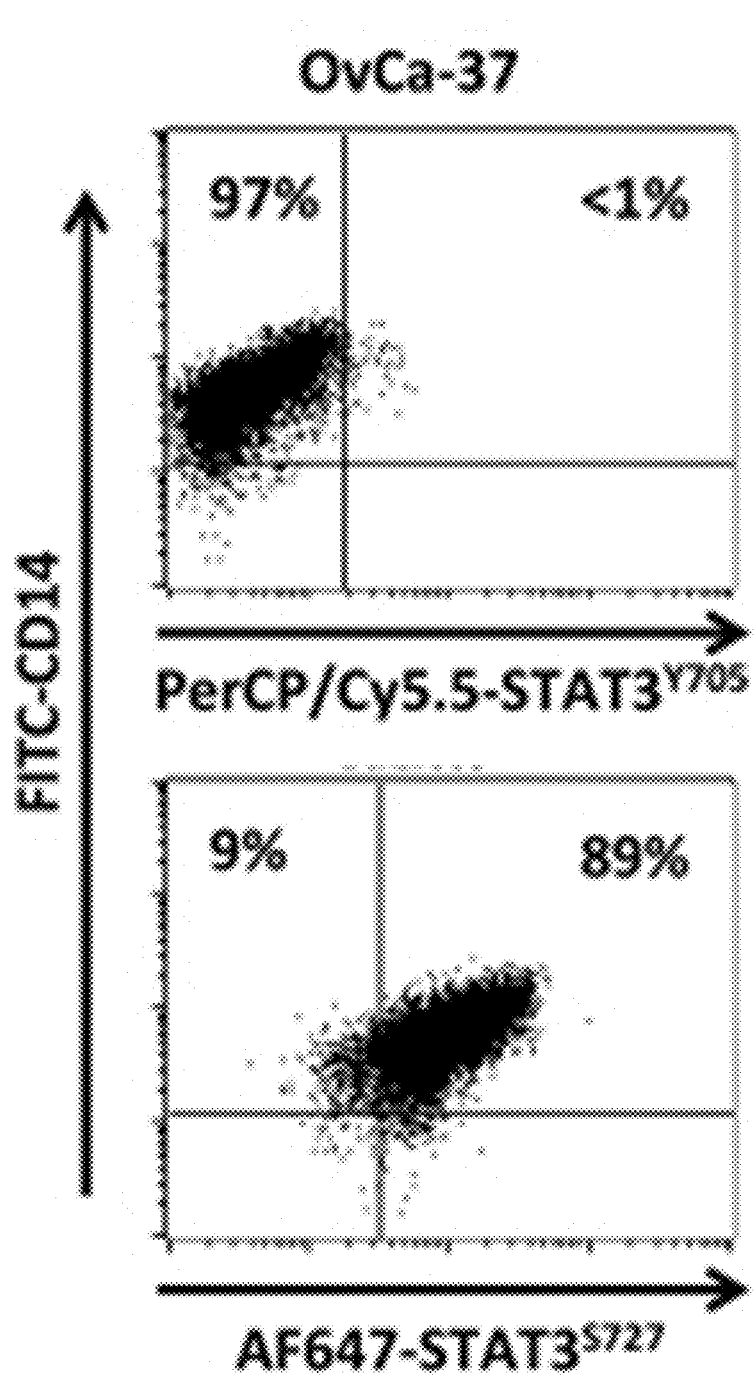
Figure 4B:
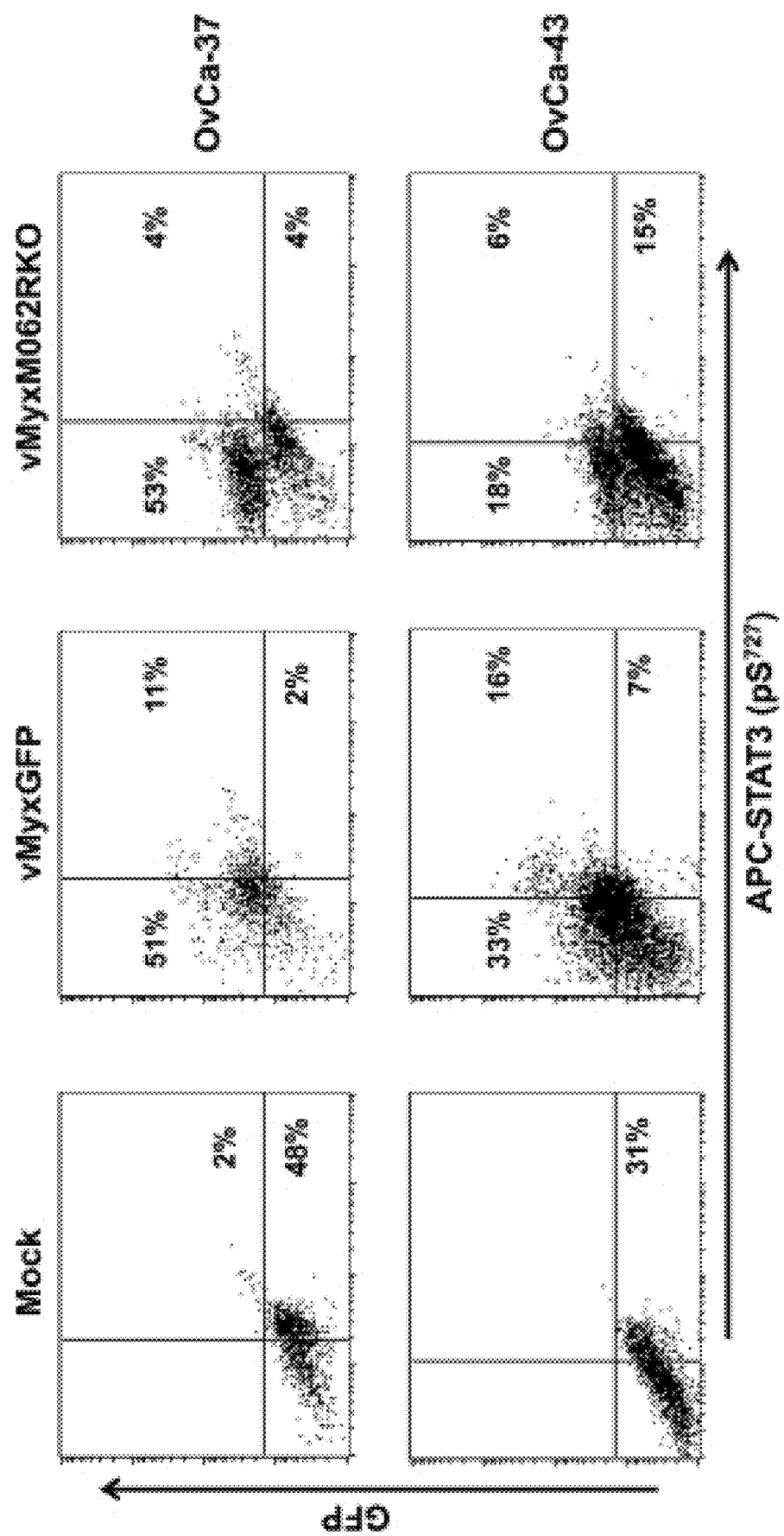
Figure 4C:
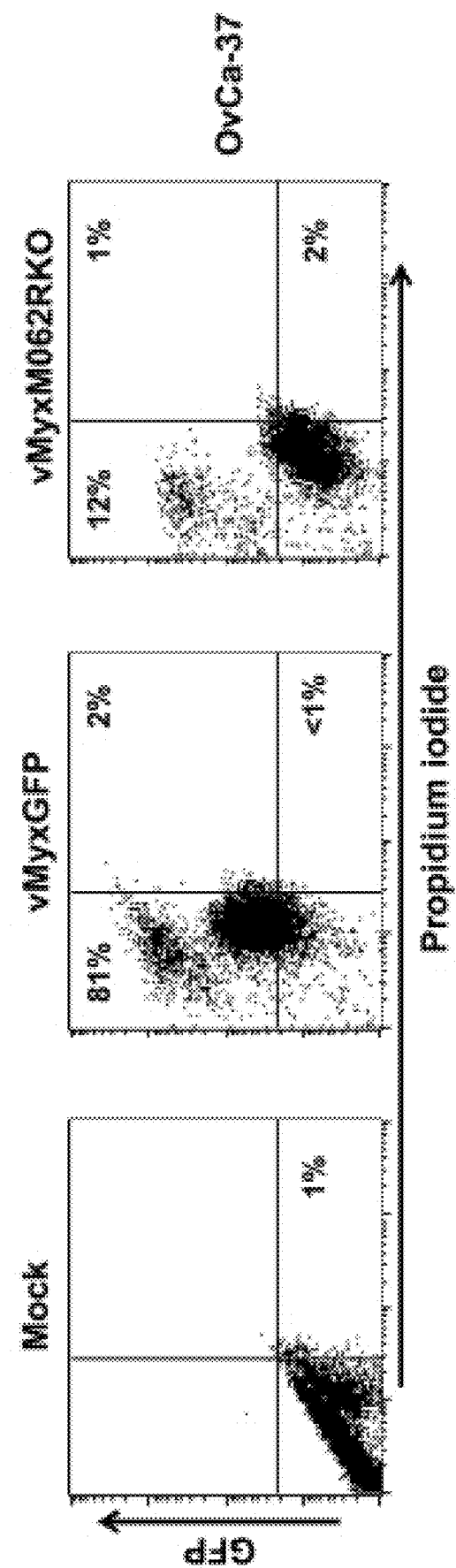
Figure 5A:
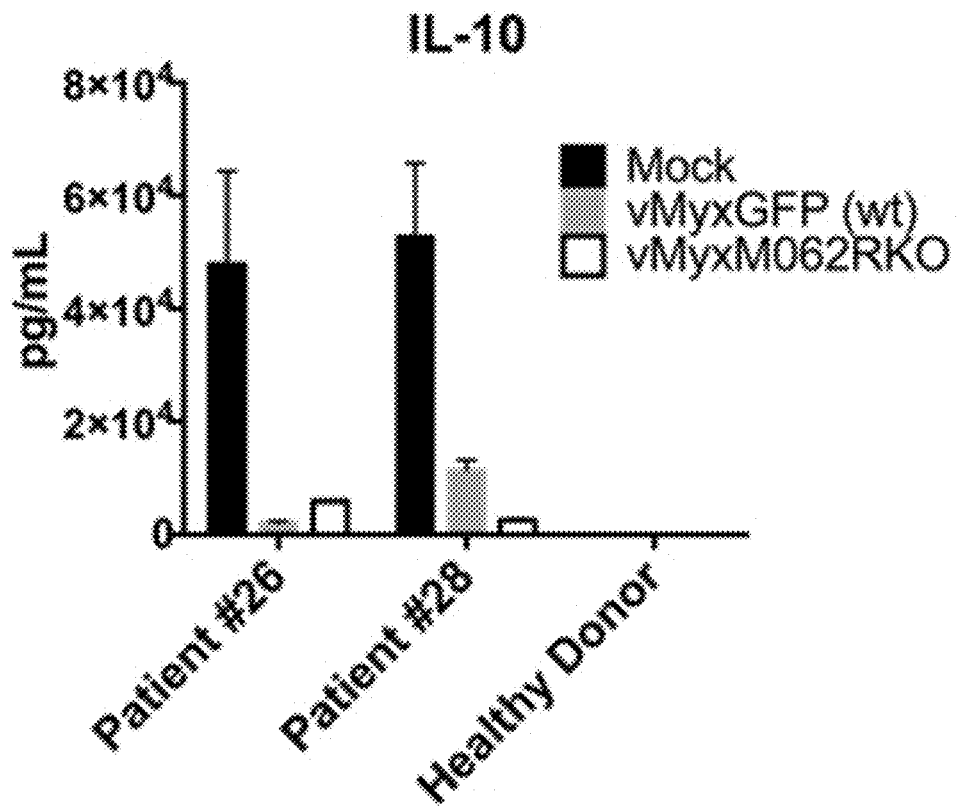
Figure 5B:
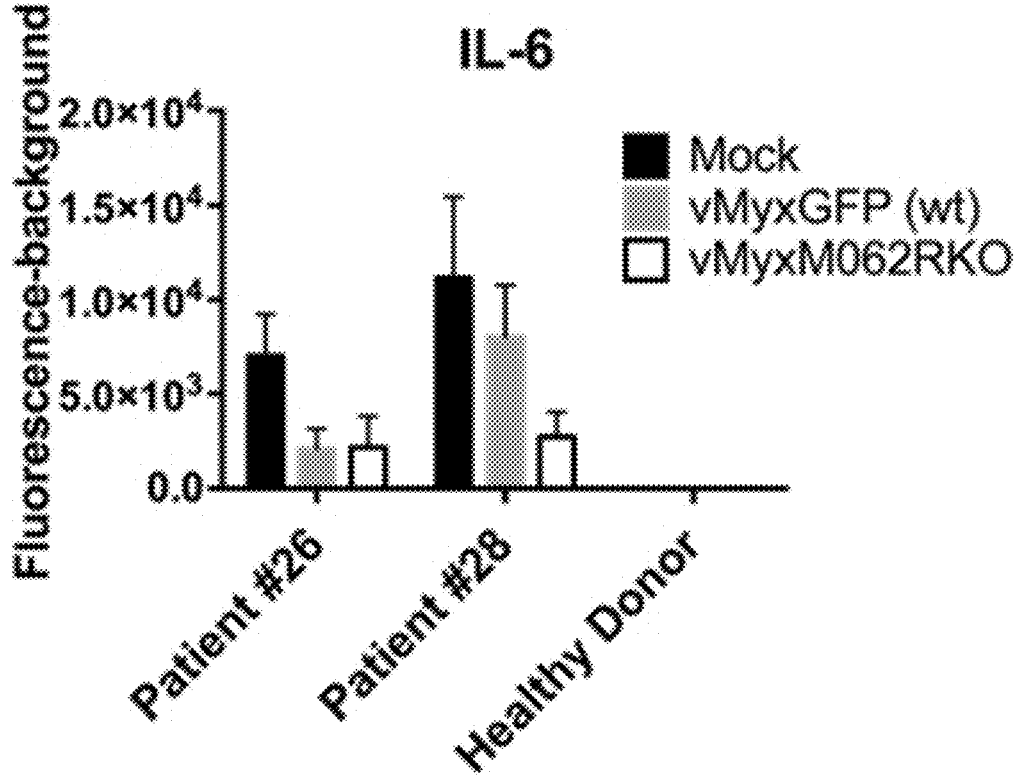
Figure 5C:
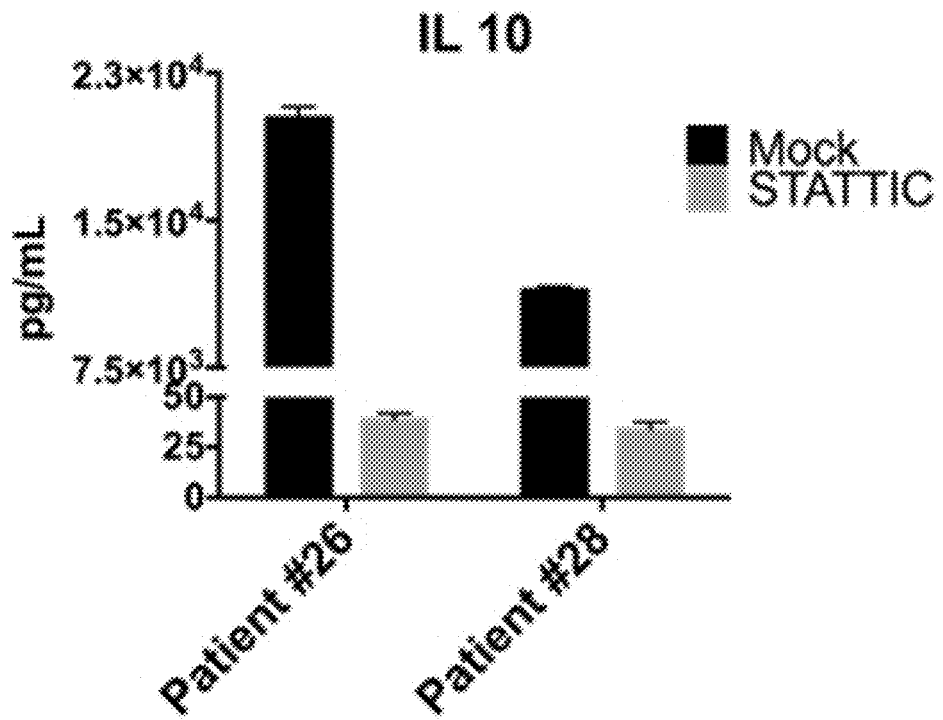
Figure 5D:
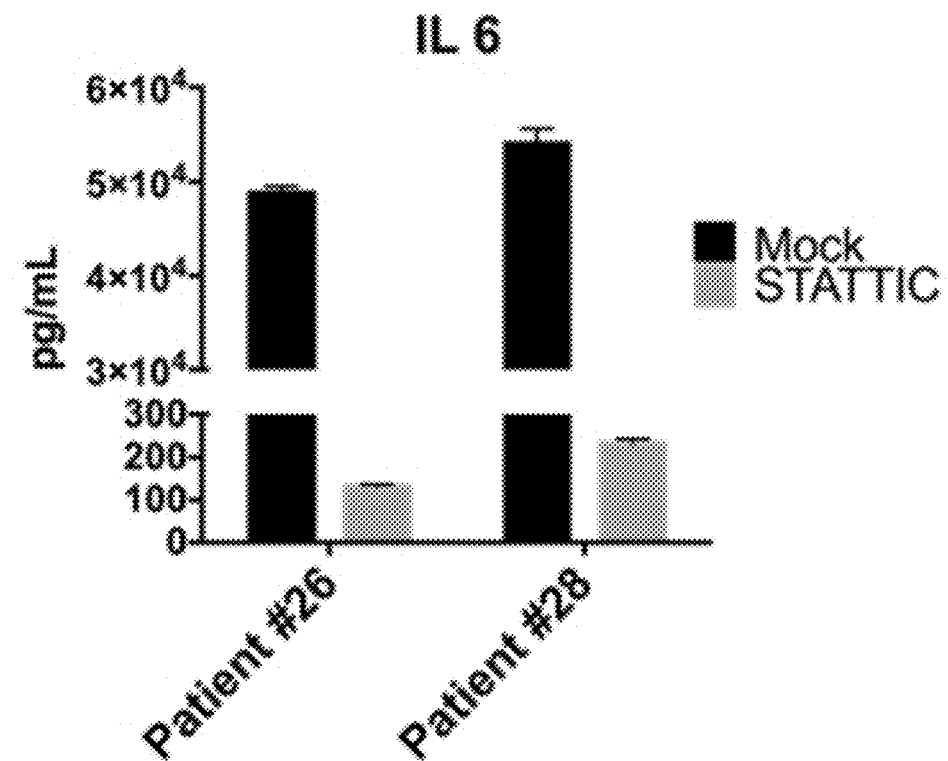

We investigated whether MYXV infection could impact the immunological properties of the OC tumor environment. We chose to examine the interaction between MYXV and OC patient ascites-associated CD14+ cells, as these cells are one of the most abundant and important players in ascites maintaining the immunosuppressive tumor environment.[28] Moreover, MYXV prefers to bind and enter human CD14+ myeloid cells rather than other immune cell types[29] and can activate the type I interferon (IFN) response by RIG-I in differentiated macrophages through an attachment-based induction.[17] However, interestingly, MYXV infection does not cause cell death in either healthy monocytes (data not shown) or OC ascites-associated CD14+ cells (FIG. 4C). We observed an unusual pattern of STAT3 phosphorylation in OC patient ascites-associated CD14+ cells with minimal phosphorylation at Y705 but a high level of phosphorylation at S727 (FIG. 4A). In OC patient ascites-associated CD14+ monocytes, infection by MYXV led to reduced phosphorylation of STAT3 at serine 727 (pS727) (FIG. 4B) and AKT (data not shown). The consequence of MYXV infection was a significant reduction in cytokine secretion, as shown by multiplex array (FIGS. 5A and 5B), which was comparable to the outcome caused by STAT3 inhibitor (Stattic) treatment (FIGS. 5C and 5D). Treatment of Stattic did not cause noticeable toxicity, and unchanged levels of IL-8 were detected by multiplex array (data not shown).

MYXV Treatment in a Syngeneic Murine OC Dissemination Model

We examined murine OC ID8 cells and found them to be sensitive to cisplatin treatment (IC50, 2.0 µM), compared to human SKOV3 cells (IC50, 8.4 µM). We evaluated MYXV as either a single agent or in combination with cisplatin in immunocompetent ID8 disseminated tumor-bearing mice.

Figure 8:
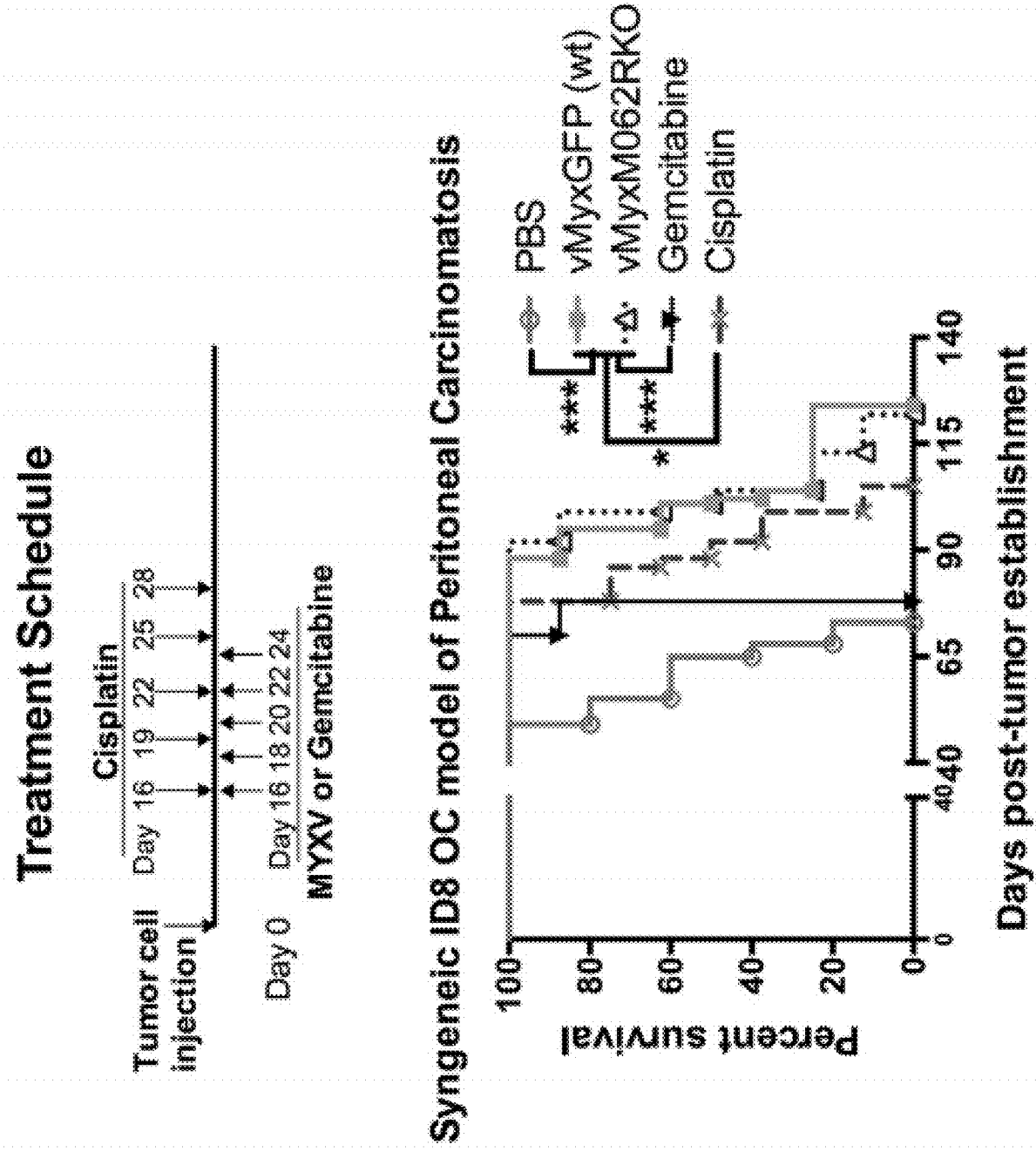

We found that as single-agent treatment given late after tumor cell injection in the syngeneic ID8 OC model, either replication-competent (vMyxGFP or WT MYXV) or -defective (M062R-null MYXV or vMyxM062RKO) MYXV provided similar benefit in prolonging survival. The treatment benefit by MYXV reached statistical significance compared to that of mock treatment, cisplatin, or gemcitabine treatment alone (FIG. 8). Gemcitabine treatment alone (50 mg/kg every other day for a total four treatments, which was modified from regimens described previously),[21,30] did not lead to significant therapeutic benefit in this model (FIG. 8).

Figure 6A:
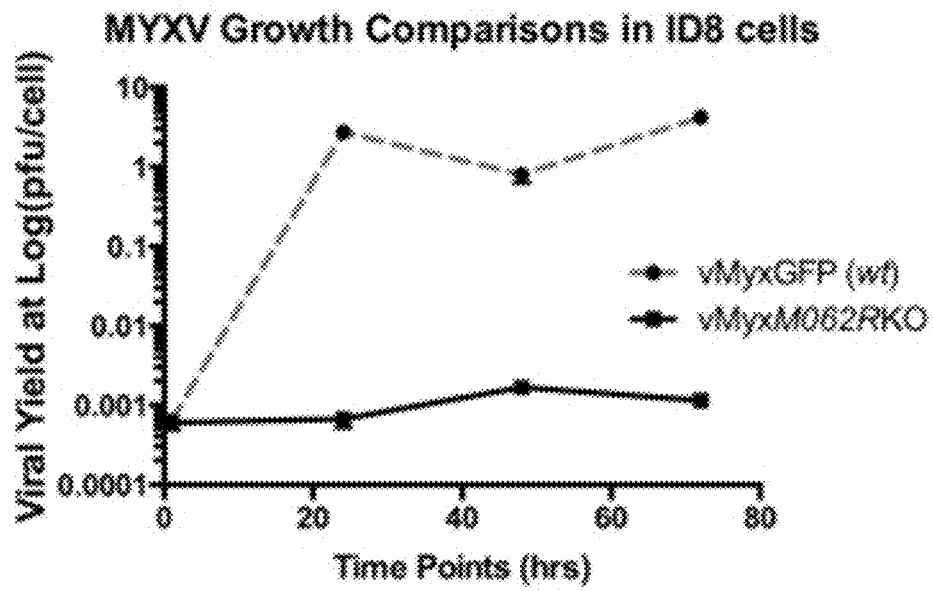
Figure 6B:
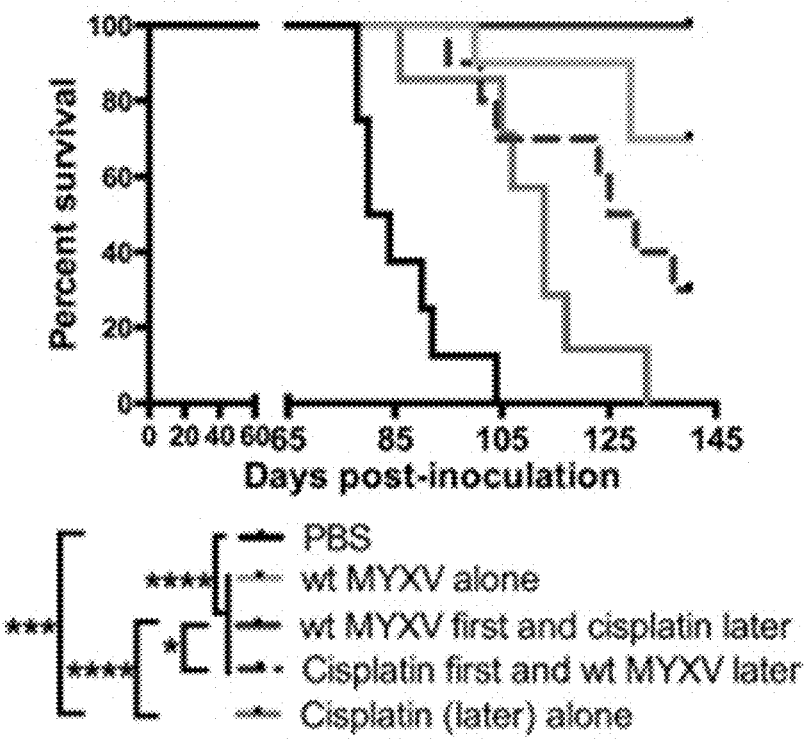

We found that the group of mice treated first with WT MYXV and then later with cisplatin remained healthy 2 months after the median survival time of the mock-treatment group (80 days), while mice in the cisplatin-alone and mock-treatment groups had all succumbed to the disease (FIG. 6B). The differences are statistically significant analyzed by log rank (Mantel-Cox) test (p<0.0001). Interestingly, although it also reached statistical significance in comparison to cisplatin-alone and mock-treatment groups (both p<0.01), treatment first with cisplatin followed by WT MYXV (30% survival) did not provide the same benefit as MYXV pretreatment followed by cisplatin (100% survival) (FIG. 6B) (p=0.0011). More importantly, when the replication-defective mutant MYXV, vMyxM062RKO, was used for pretreatment before cisplatin (60% survival), we did not observe the same benefit conferred by WT MYXV pretreatment (FIG. 6B and solid orange line in FIG. 6D; 100% survival). Thus, a replication-competent MYXV is important to sensitize cancer cells to a following cisplatin treatment in order to achieve an optimal therapeutic outcome. Unexpectedly, the regime of M062R-null MYXV treatment after cisplatin (90% survival) provided a better survival outcome than cisplatin alone (40% survival) (log rank Mantel-Cox test; p=0.0329) or mutant virus followed by cisplatin (FIG. 6D) (60% survival; p=0.1605).

We collected splenocytes from surviving mice from the following groups 100 days after tumor cell injection: cisplatin alone (early treatment group as in FIG. 6B, collected after 100 days), WT MYXV alone (FIG. 6B) (collected after 140 days), cisplatin plus WT MYXV (FIG. 6B) (collected after 140 days), and WT MYXV plus cisplatin (FIG. 6B) (collected after 140 days). After stimulation of spleen cells with ID8 tumor antigen, we examined IFNγ secretion in the supernatant as a measurement of immune cell activation. Splenocytes from the group treated with WT MYXV plus cisplatin consistently showed a strong IFNγ response (FIG. 6C).

Discussion

The oncolytic potential of MYXV is largely due to the intracellular environment of tumor cells that permits a productive MYXV infection, including highly phosphorylated AKT31 and loss of synergistic effects of the tumor necrosis factor (TNF) and IFN responses, in the transformed cells.[32,33] The mechanism of oncolysis by MYXV, however, varies by the type of cancer.[34,35] We found that apoptosis was not the major driver of oncolysis by MYXV in the OC cells tested, including primary OC cells derived from patient ascites. Although replication competence can moderately increase cell death, such as in WT MYXV-infected primary OC cells, the overall inhibitory effect to OC cell growth seemed to be replication independent. Further investigation on the mechanism is ongoing. More importantly, pretreatment with MYXV sensitized OC cells to much lower doses of chemotherapy agents than those given when the agents are used alone. Further investigation into the mechanism of this sensitization process is needed. It is encouraging to examine whether this treatment approach may be an alternative strategy to target chemoresistance in many OC cells, especially recurrent tumor arising after first-line chemotherapy treatment.

Within human OC ascites, CD14+ monocytes/macrophages are one of the most abundant immune cell populations.[5,28] These myeloid cells have an M2 immunosuppressive phenotype and have been linked to resistance to platinum-based chemotherapy agents.[36] The ability of CD14+ myeloid cells to produce IL-10 has a suppressive effect on T cells present in the OC tumor environment in the peritoneal cavity.[37,38] MYXV preferentially binds and enters human CD14+ cells rather than other immune cells to initiate early gene expression without resulting in a productive infection.[29] We found that MYXV did not affect the general viability of healthy human CD14+ cells. However, MYXV infection in OC ascites-associated CD14+ cells led to an inhibitory effect on multiple signaling pathways associated with cytokine secretion patterns that contribute to the immunosuppressive tumor environment. Thus, MYXV can be a potential immunotherapeutic tool for targeting CD14+ monocytes in the tumor environment. In the murine ID8 model of OC, we found the presence of CD11b+ cell population but few F4/80+ cells (mature macrophages) in the ascites of mice injected with this clone of ID8 cells (data not shown). It is not an optimal system to investigate the MYXV therapeutic effect against the equivalent of CD14+ cell type in human OC ascites. A recently developed model using p53 null ID8 cells with high levels of macrophages infiltration in the ascites[39] can be a system to extend the investigation.

An initial characterization of OC patient ascites-associated CD14+ cells showed active AKT signaling and a non-canonical state of STAT3 signaling (STAT3 pY705low/none pS727high). Targeting STAT3 signaling to reverse chemoresistance in OC has been suggested.[40] However, the roles of non-canonical STAT3 signaling in OC disease progression and maintenance of immunological properties of OC are not yet characterized. Phosphorylation at serine 727 of STAT3 permits a maximal transcription activity in principle.[41] We utilized a specific inhibitor of STAT3, Stattic, to prevent STAT3 homodimerization and DNA binding[42] and observed suppressive effect in cytokine secretion of tumor-associated CD14+ macrophages (FIGS. 5A-5D, control). Our results showed that MYXV infection could suppress STAT3 (STAT3 pY705low/none pS727high) and ATK signaling; this effect could be further enhanced when engineered M062R-null MYXV was used.

Cisplatin treatment can also affect the tumor environment, including induction of a tumor-specific CD8+ T cell response.[43] We found that pretreatment with replication-competent MYXV followed by cisplatin greatly improved survival, compared with cisplatin alone. Interestingly, treating mice first with cisplatin followed by replicating MYXV did not achieve the same treatment benefit. Even with replicating MYXV, the viral infection was eliminated within 7 days in immunocompetent mice.[21] Thus, it is possible that transient MYXV infection remodels the tumor environment, sensitizing tumor cells to a later cisplatin intervention. It seems that the initial phase of viral replication is crucial to a favorable treatment outcome when the combinatorial and sequential WT MYXV-cisplatin regimen is used.

However, intriguingly, use of the replication-defective MYXV, M062R-null MYXV, after cisplatin treatment in this OC dissemination model led to 90% survival in mice and was much more effective than the use of replicating MYXV after cisplatin treatment (60% survival). Cisplatin inhibits DNA replication of MYXV (data not shown); therefore, cisplatin and MYXV cannot be applied at the same time, as was explored with reovirus virotherapy.[26] The lack of statistically significant differences in disease progression between groups treated with cisplatin alone and cisplatin followed by WT MYXV suggests that even 5 days after cessation of cisplatin treatment, the effect of inhibiting a subsequent productive MYXV infection in the tumor environment persists. Accordingly, we speculate that the favorable outcome of cisplatin plus later M062R null MYXV treatment may be unique to this mutant-virus. In human cells, M062R-null MYXV infection activates the anti-neoplastic SAMD9 pathway.[44] It is not known whether infection with M062R-null MYXV in this murine model stimulates a similar pathway that can specifically enhance the outcome of preceding cisplatin treatment.

In human OC ascites-associated CD14+ cells, M062R-null MYXV effectively suppresses STAT3 phosphorylation (FIG. 4B) and AKT (data not shown) and reduces phosphorylated CREB (data not shown), all important signaling molecules in the maintenance of the M2 state of tumor-associated myeloid cells.

Development of novel treatment approaches for OC patients is urgently needed. We showed that an oncolytic virotherapy candidate, MYXV, could be integrated into and complement an existing chemotherapy regimen to improve the treatment benefit in an immunocompetent preclinical model. We are investigating the mechanism of MYXV immunotherapeutic potential in the OC tumor environment, especially the effect on OC ascites-associated CD14+ cells. To the best of our knowledge, this is the first study that investigates the benefit of combining MYXV with cisplatin in the treatment of OC in a syngeneic model in vivo.

Materials and Methods

Human Subjects

Ovarian cancer patients were recruited from patients attending the Women's Oncology clinic in the Winthrop P. Rockefeller Cancer Institute, University of Arkansas for Medical Sciences (UAMS), under an IRB-approved protocol. Ovarian tumor ascites samples were recovered at the time of surgery.

Characterization of Patient Samples (1) Clinical characteristics of patient tumor samples are as follows:

OvCa-2a, clear cell carcinoma

OvCa-26, metastatic adenocarcinoma that is moderately differentiated but lacks clear-cut high-grade serous, clear cell, or endometrioid differentiation OvCa-2a and OvCa-26, both newly established ovarian cancer cell lines. OvCa-2a is EpCAM$^{hi}$ CD133$^{hi}$ A-cadherin$^{neg}$ and it has a stem-like phenotype. OvCa-26 is EpCAM$^{hi}$, CD133$^{hi}$ E-cadherin$^{lo}$ and also has elements of a stem-like phenotype. Both cell lines express ALDH1. TP53 mutation status is unknown.

(2) Clinical characterization of patient tumor type with which tumor-associated macrophages were purified from ascites are as follows:

OvCa-28, mucinous cystadenocarcinoma

OvCa-37, high-grade serous carcinoma

OvCa-43, high-grade serous carcinoma.

Cell Lines and Viruses

SKOV3,[45] OvCa-26 (primary human OC cells), OvCa-2a (primary human OC cells), and ID8 (courtesy of Katherine Roby, PhD, University of Kansas Medical Center) cells[46] were cultured in RPMI1640 (Mediatech, Corning, NY) supplemented with 2 mM L-glutamine (Invitrogen, Carlsbad, CA), 5×10-5 M 2-mercaptoethanol (Thermo Fisher Scientific, Waltham, MA), and 100 µg/mL of penicillin/streptomycin (Invitrogen). MYXV viruses, vMyxGFP-WT and M062R-null MYXV (vMyxM062RKO), have been described previously.[47] Both viruses were engineered to express GFP driven by a viral synthetic promoter from which GFP is synthesized throughout the course of infection. Viruses are amplified on BSC-40 cells and purified through 36% sucrose gradient as previously described.[21, 47, 48] BSC-40 cells were cultured in Dulbecco's minimal essential medium (Lonza, Basel, Switzerland, and Invitrogen) supplemented with 10% fetal bovine serum (Atlanta Biologicals, Flowery Branch, GA), 2 mM glutamine (Corning, Corning, NY), and 100 µg/mL of penicillin/streptomycin (Invitrogen).

Reagents and Antibodies

Chemotherapy drugs cisplatin (Sigma-Aldrich, St. Louis, MO) and gemcitabine (Sigma-Aldrich) were diluted to appropriate concentrations in growth medium for treatment in vitro and were diluted in PBS for animal treatment. Stattic (Selleckchem, Houston, TX) was dissolved in DMSO at 10 mM, and patient ascites-associated monocytes were treated at a concentration of 5 µM before cytokine secretion was tested. The antibodies STAT3 pY705, STAT3 pS727, total STAT3, AKT pS473, and pCREB, as well as the Annexin V Apoptosis Detection Kit APC, are from Affymetrix eBioscience (San Diego, CA).

Colony-Formation Assay and MTT Assay

Colony-formation assay was conducted as previously described.[21] Briefly, cancer cells were treated with MYXV at an MOI of 50 before they were diluted for seeding in a 10-cm dish. Depending on the cell lines used, after 2-6 weeks of growth, cells were fixed and stained with crystal violet for imaging. Cell viability was measured by MTT assay (Promega, Madison, WI) according to the manufacturer's protocol.

Combinatorial Treatment Test In Vitro

To calculate IC50 dose for each cell line, we adopted a method similar to what was previously reported.[21] Briefly, cells were treated with chemotherapy drug at serial diluted doses for 48-72 hr before cell proliferation was measured with MTT assay.

Primary patient ascites-derived tumor cells (OvCa-2a and OvCa-26) were mock-treated or infected with MYXV (replicating WT or defective M062R-null MYXV) at an MOI of 10 for 48 hr before they were cultured for 24 hr in fresh medium without any treatment; cells were then treated with a second treatment (chemotherapy or virus) for another 48 hr before cell viability was measured with MTT assay (Promega).

Human Healthy CD14+ Monocytes and OC Patient Tumor-Associated CD14+ Monocytes

Human CD14+ monocytes are from healthy female donors (Lonza). OC tumor-associated CD14+ monocytes were purified from patient ascites as described previously.[38] Briefly, primary ovarian tumor ascites CD14+ cells were separated magnetically using commercially available columns and anti-CD14 conjugated microbeads (Miltenyi Biotec, Auburn, CA), according to the manufacturer's instructions. The purity of recovered ascites CD14+ cells was typically 95%-98%.

Flow Cytometry, ELISA, and Multiplex Array

After appropriate treatments, cells were fixed and permeablized with fixation/permeablilization concentrate (Affymetrix eBioscience) and stained according to the manufacturer's instructions with antibodies recognizing intracellular signaling phosphoproteins. The mouse IFNγ ELISA and ProcartaPlex human inflammation panel (20 plex) (Affymetrix eBioscience) were performed according to manufacturer's instructions. A customized multiplex array (Millipore, Billerica, MA) was used to characterize Stattic-treated patient-ascites monocytes. To examine IFNγ secretion in splenocytes to tumor antigen stimulation, mouse splenocytes were harvested and treated with ACK lysing buffer (Thermo Fisher Scientific) at 1:1 volume ratio for 5 min at room temperature before cells were pelleted. Approximately 10 million cells per mouse were either mock treated or stimulated with ID8 cell lysate (technical replicates in duplicate). At 1 day and 3 days post-stimulation, a sample of supernatant was taken per well and stored at −80° C. for ELISA (eBioscience). These splenocytes continued to be cultured, and at day 6, media were replaced to contain ID8 tumor lysate for the second round of stimulation. At days 7 and 10, samples of supernatant were again taken per well for ELISA. To prepare ID8 tumor cell lysate as a crude tumor antigen preparation, we resuspended one million ID8 cells in 1 mL of medium for 3 rounds of freeze-thaw cycle followed by sonication; 125 µL of tumor cell lysate was used to stimulate 10 million splenocytes.

Murine Model of OC Dissemination and Treatments

The animal studies were approved by the IACUC at the University of Arkansas for Medical Sciences (UAMS). Cisplatin was administered at 3 mg/kg every 3 days as described previously.[49] In a regimen modified from those described previously,[21, 30] gemcitabine was administered at 50 mg/kg every other day for a total four treatments. Virotherapy was carried out every other day for a total of four or five intraperitoneal (i.p.) injections as described previously.[21]

To test the therapeutic effect of combined virus and chemotherapy treatment, treatment started 7 days after i.p. injection of a dose of 6×10$^6$ tumor cells/mouse. Injecting fewer cells of this ID8 clone (e.g., 1×10$^6$ or 3×10$^6$ cells) failed to provide the same disease progression and survival outcome as shown in this study (e.g., FIG. 8). For combinatorial treatment of virus followed by cisplatin, four i.p. injections of 1×10$^8$ plaque-forming units (PFUs)/mouse every other day were carried out, and cisplatin treatment was begun 5 days after the last injection of virus as described above. For combination treatment of cisplatin first followed by virus, cisplatin treatment was carried out as described above with a 5-day interval before the virus treatment (five injections every other day). As a control, cisplatin treatment was tested at either 7 days (early) or 16 days (late) post-injection of tumor cells. To test single-agent virotherapy, cisplatin, or gemcitabine treatment, treatments were initiated at 16 days post-tumor-injection.

Example 2: Myxoma Virus Virotherapy Enhances Treatment Benefit of Chemotherapy and Th17-Inducing Dendritic Cell Immunotherapy in Ovarian Cancer Preclinical Model Introduction Ovarian cancer (OC) is a leading cause of gynecological cancer deaths worldwide and the second most prevalent cause of new cancer diagnoses. In recent years, the immunosuppressive property of the OC tumor environment has been found to be correlated with poor prognosis and reduced survival limes. In the tumor environment tumor-associated macrophages (TAMs) make up a largo portion of immune cell population. These cells create an immunologically privileged space which allows the tumor to escape host immunosurveillance, resist chemotherapeutic agents and blunt the anti-tumor immune response. Now immunotherapeutic agents which break the immunosuppression protecting the tumor are needed to augment current therapies. Novel immunotherapeutic strategies such as our Th17-stimulating dendritic cell (DC) vaccine are being tested in the clinic.

Myxoma virus (MYXV) is a poxvirus with a narrow host range in nature, infecting only rabbits. However, MYXV possesses oncolytic potential and has recently been shown to be an excellent immunotherapeutic agent. We study a viral immunoregulatory gene, M062R, and found that mutant virus deleted for this gene (M062R-null MYXV) have a beneficial therapeutic effect despite an abortive infection. In human primary OC cells M062R-null MYXV induces a potent IFNβ and type I interferon (IFN-I) response. Moreover, it effectively improved survival when it is administrated after cisplatin, the first line chemotherapy for OC. We hypothesize that the IFN-I response evoked by infection with MYXV and M062R-null MYXV facilitates improved survival times by amelioration of the immunosuppressive tumor microenvironment, which allows clearance of tumor cells. The treatment regimen was tested in a model of OC model (a syngeneic ID8 Trp53$^{-/-}$ tumor cell implantation model in immunocompetent mice) that closely portrays human high grade serous OC (HGSOC). We find that 1) infection with WT and M062R-null MYXV in tumor cells evokes IFN-I expression; 2) M062R-null MYXV can synergize with Th17-DC vaccine to eliminate tumor cells.

Results

Figure 9C:
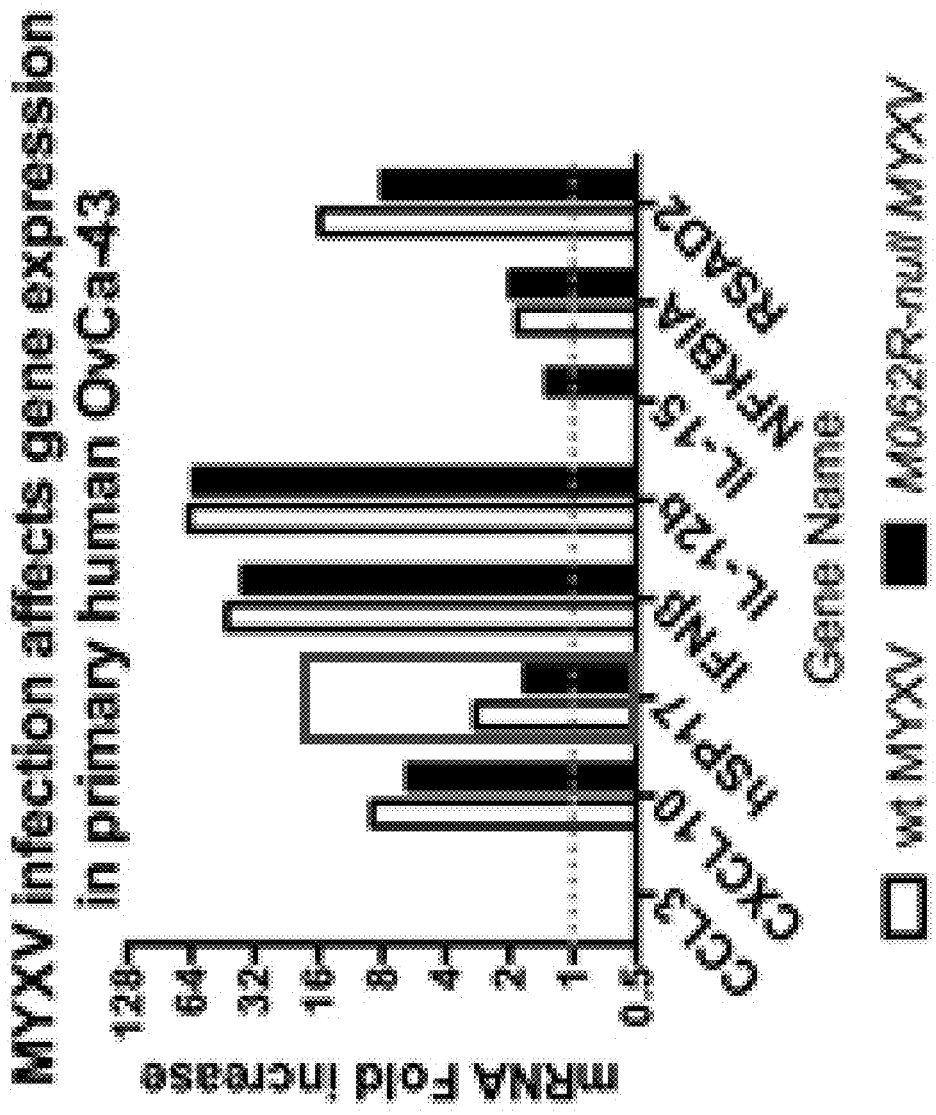
Figure 9D:
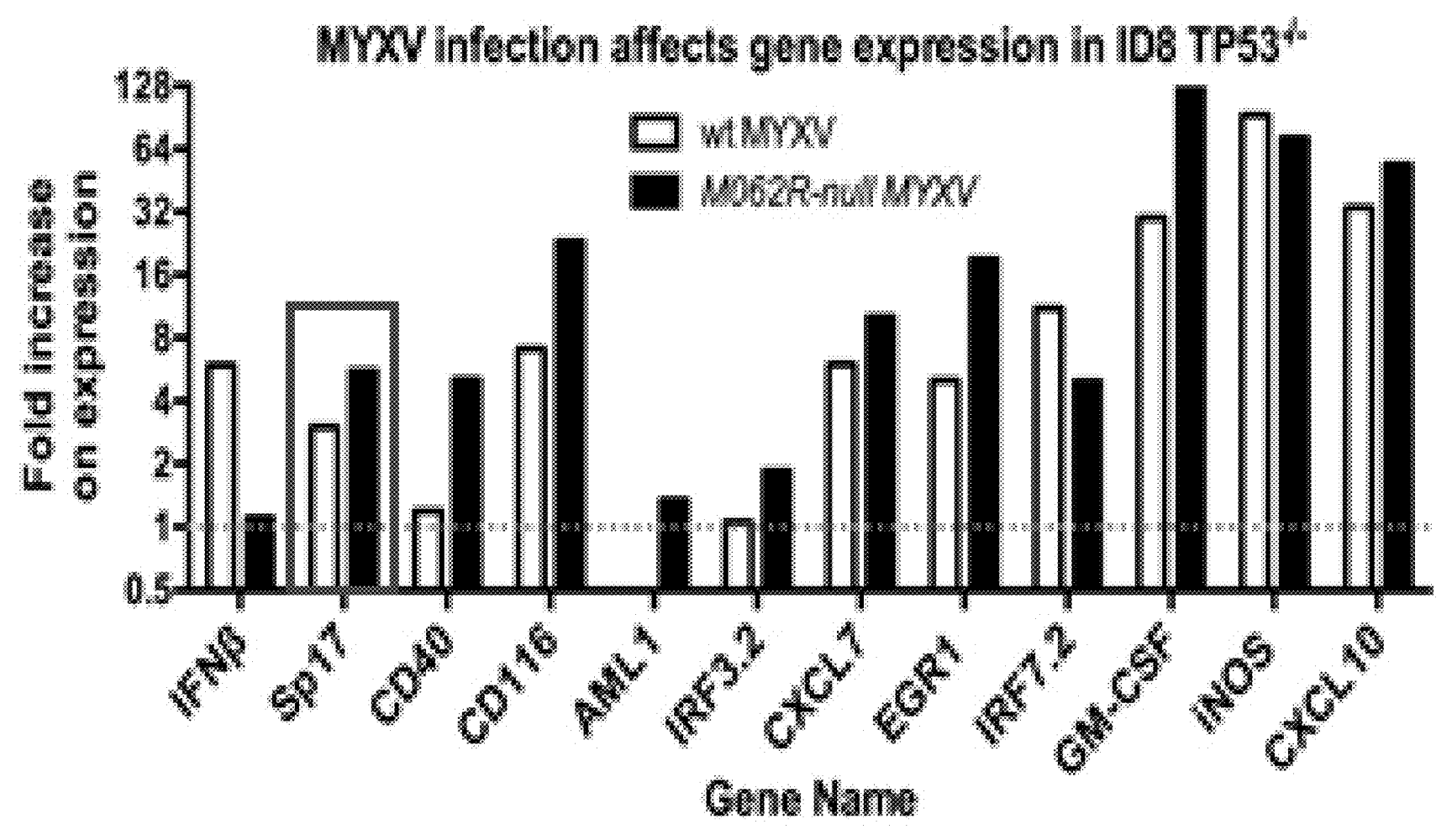
Figure 9E:
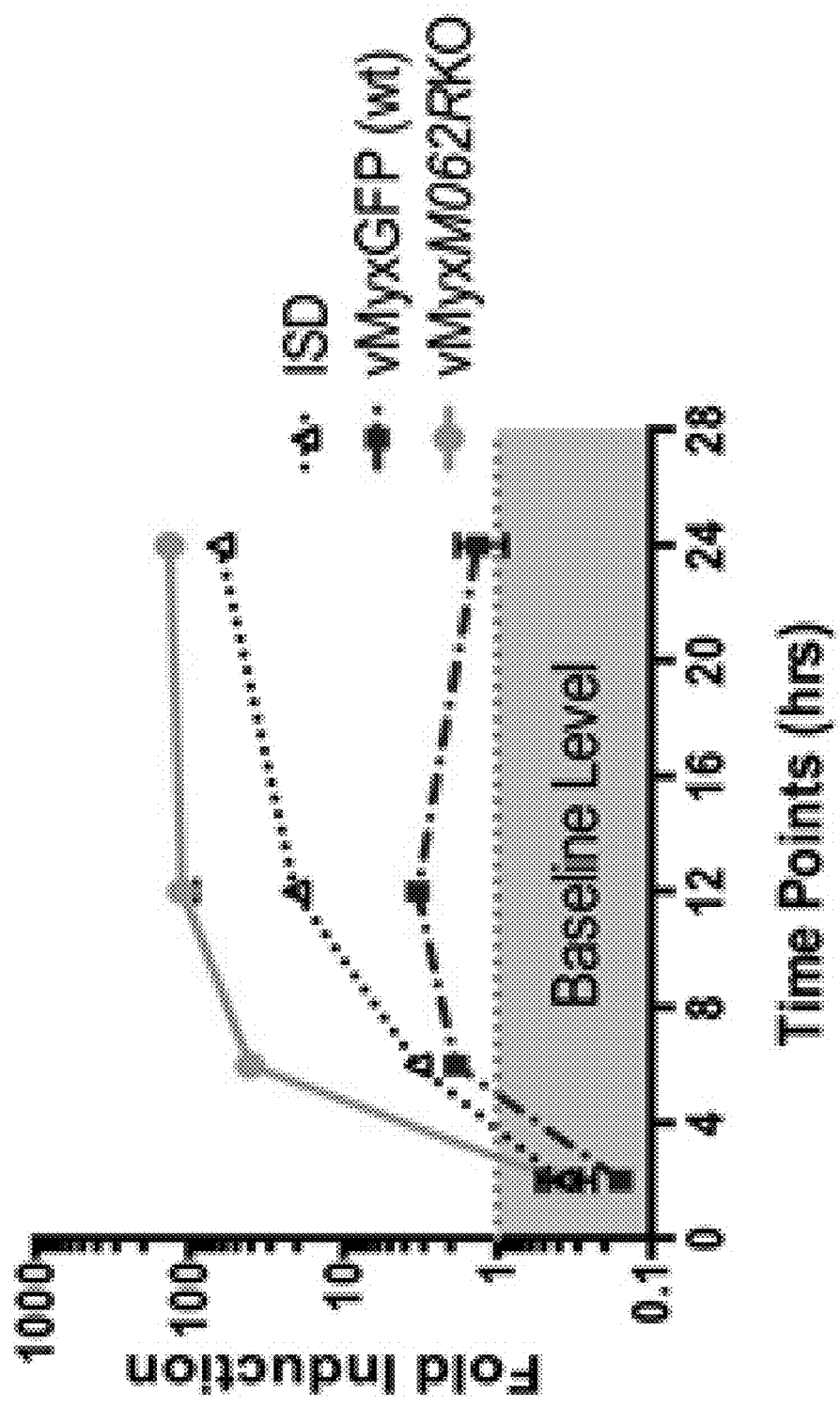

In human primary OC cells M062R-null MYXV induces a potent IFNβ and IFN-I responses (FIG. 9A-C). This pro-inflammatory stimulation by M062R-null MYXV in primary patient OC tumor cells is comparable or significantly enhanced compared to what was observed in WT MYXV infected cells. In addition to human OC tumor cells, we also observed similar effect by M062R-null MYXV in ID8 Trp53$^{-/-}$ tumor cell (FIG. 9D). Moreover, M062R-null MYXV infection in human and mouse OC tumor cells provoked elevated Sp17 expression that is a signature tumor antigen in not only OC tumor cells but also detected many other malignant tumor cells (red box in FIGS. 9A, 9C, and 9D). In human macrophages derived from THP-1 monocytic cells we found M062R-null MYXV infection uniquely provoked IRF-dependent gene expression (FIG. 9E) that can be used as a surrogate of IFN-I and ISGs. Thus the mechanism for M062R-null MYXV-mediated IFN-I responses is IRF-dependent.

Figure 10A:
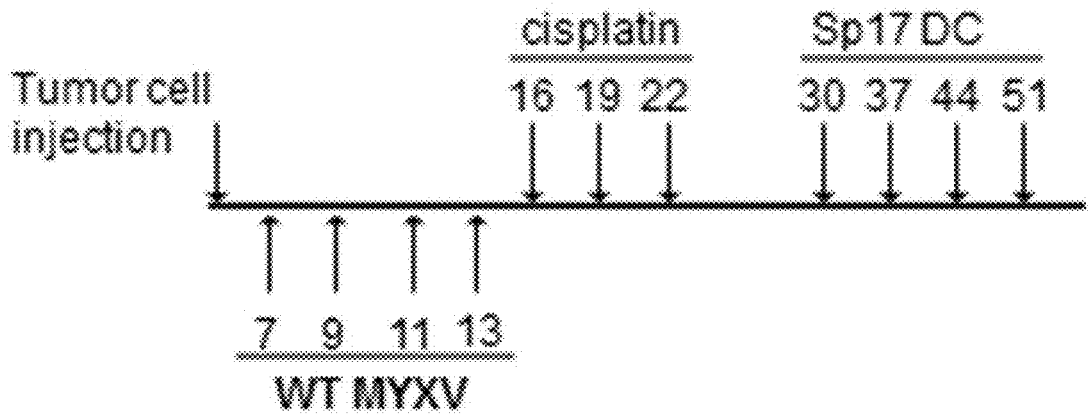
Figure 10B:
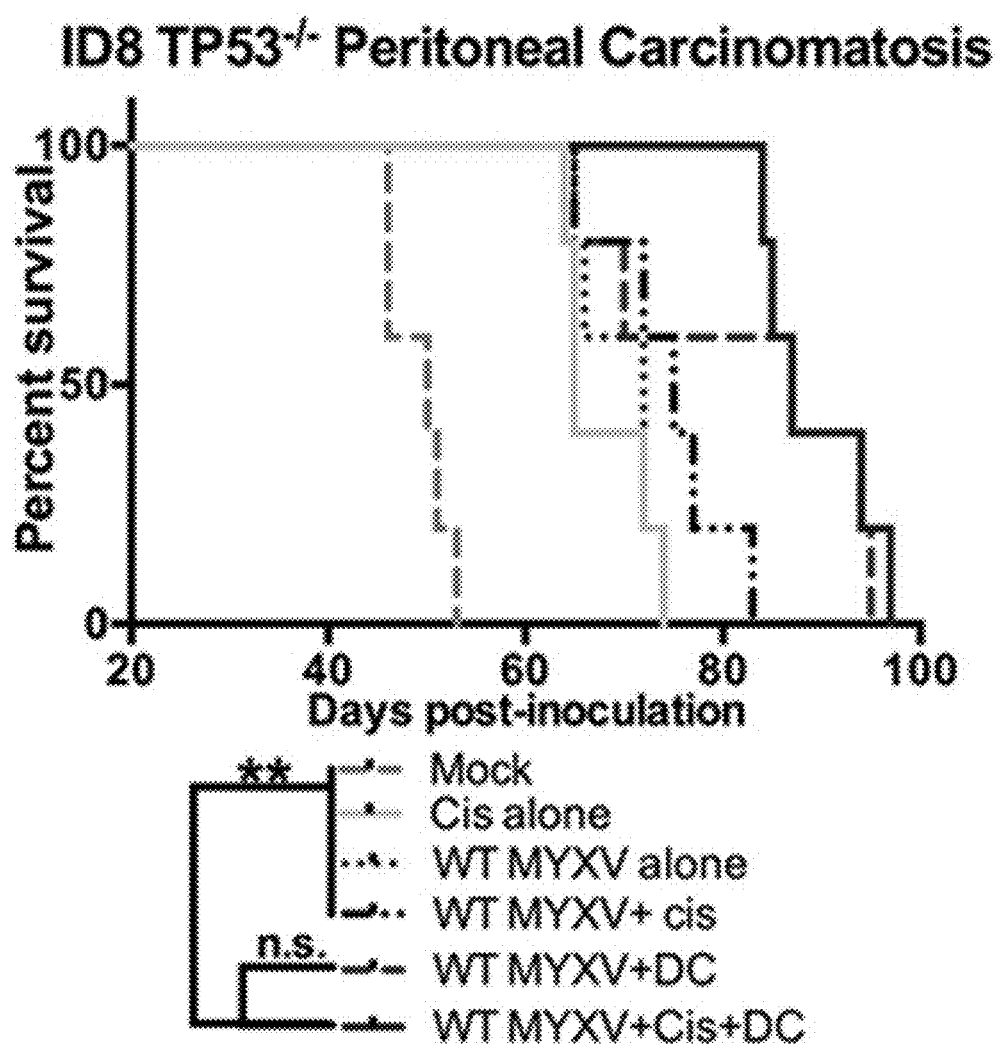
Figure 11A:
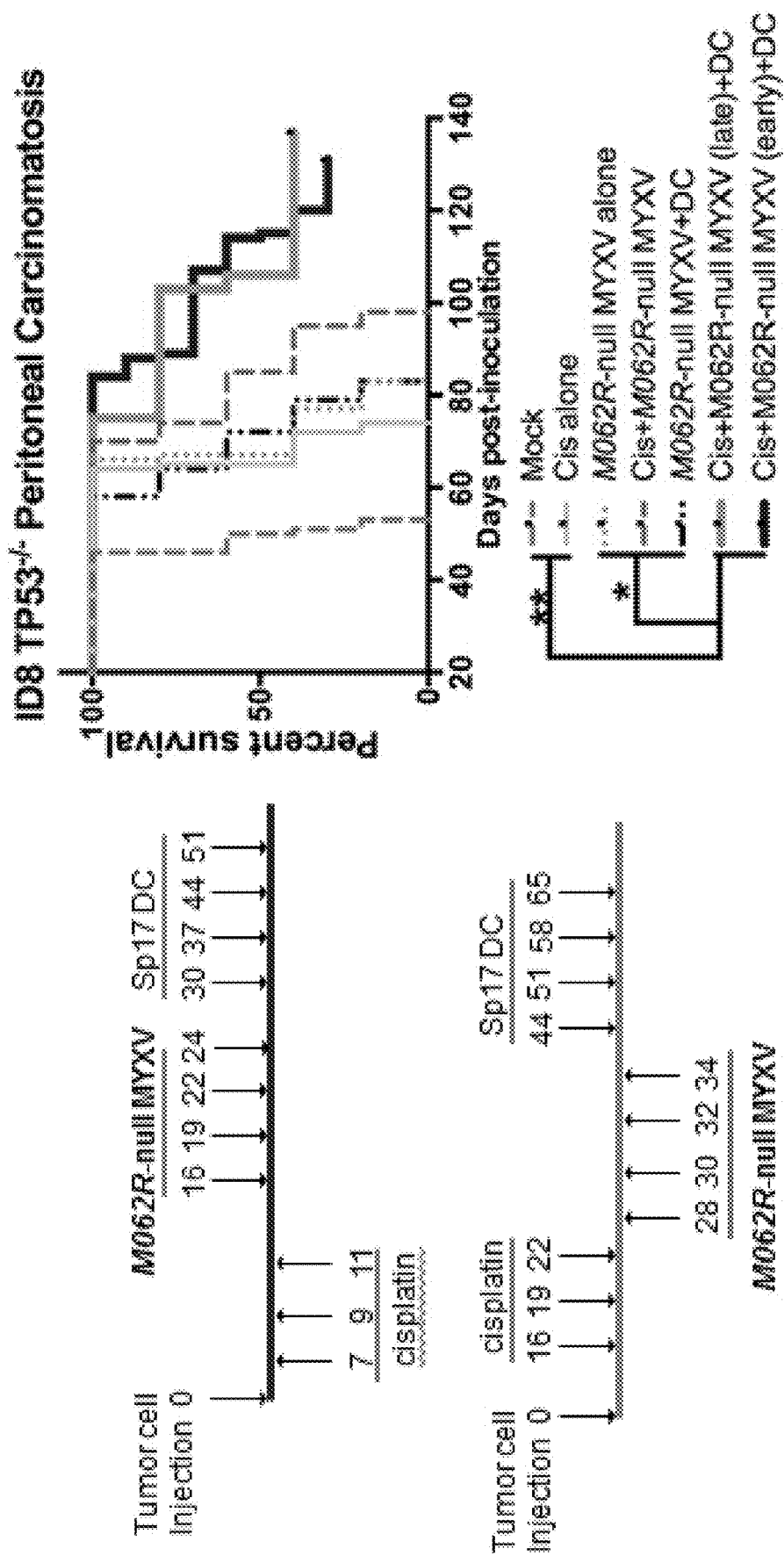
Figure 11B:
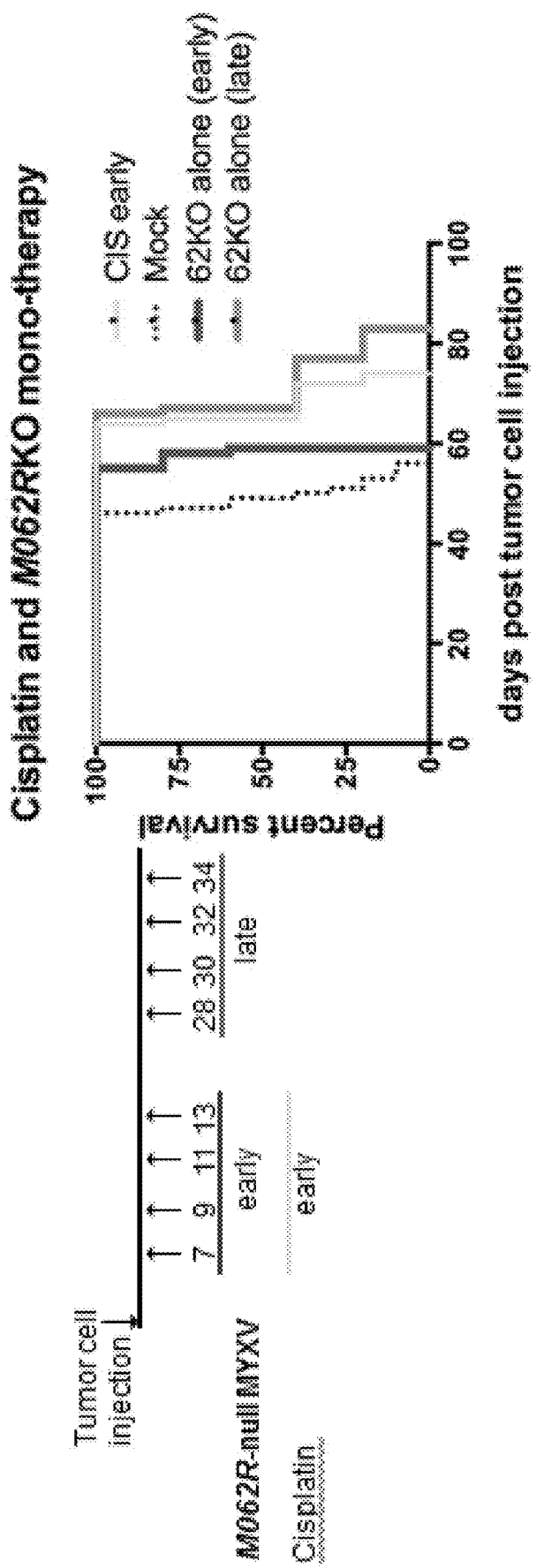

We initially tested the application of combining cisplatin, MYXV, and DC vaccine in treating OC in the syngeneic ID8 Trp53$^{-/-}$ tumor cell implantation model that closely portrays high grade serous OC (HGSOC) in patients. We found that WT MYXV reasonably prolonged survival (FIG. 10). More importantly, we found that in this model M062R-null MYXV presented therapeutic benefits when used alone, in combination with cisplatin, with DC or in combination with cisplatin and DC vaccine (FIG. 11A). Applying M062R-null MYXV when the tumor environment is mature that is as late as 28 days post tumor cell establishment (FIGS. 11A and 11B) in this mouse model provided the largest therapeutic benefit; we detected 40% survival at the end point of the study and all surviving mice were healthy at the time (FIG. 11A).

Discussion

We have utilized a new syngeneic mouse model of high grade serous OC in which the Trp53 gene is deleted (ID8 Trp53$^{-/-}$). Its disease progression closely resembles that in human OC patients with the immunosuppressive tumor environment. We utilize an engineered MYXV with a targeted deletion of the essential viral immunoregulalory gene, M062R. This virus is replication incompetent in most cell lines but evokes a pronounced type I IFN response compared with the WT virus.

MYXV is an extremely attractive platform for immunotherapy. Wild type MYXV displays a tropism for human tumor cells, but, unlike vaccinia virus (VACV), it does not replicate productively in healthy human cells and therefore offers unparalleled safety. MYXV infection targets both tumor cells and disease macrophages in the tumor microenvironment. The most successful oncolytic viruses would be able to infiltrate and subvert the immunosuppressive tumor microenvironment cultivated by tumor cells. We have demonstrated that the M062R-null MYXV is a potent activator of IFN-I response, even more so than the replication-competent wild type MYXV. The M062R-null MYXV is able to prolong survival as a monotherapy especially when it is administrated into a well-established immunosuppressive tumor environment; it can be effectively applied in combination with cisplatin. More important, M062R-null MYXV significantly improves the treatment benefit of DC vaccine that is often administrated after cisplatin. Infection with the M062R-null MYXV stimulates IFN-I and other inflammatory cytokines that are secreted directly into the tumor microenvironment. Viral infection also upregulates production of Sp17 mRNA in the tumor cells, which, together with Sp17-loaded Th17-DC vaccine, allows for a two-pronged attack upon the tumor: One from Th17 CD4+ T cells previously sensitized by Sp17 loaded DC, and the other one in which the immunosuppressive tumor microenvironment is subverted, resulting in recovery of the anti-tumor effect mediated by helper and cytotoxic T cells.

Materials and Methods

Human OC patient tumor cells were purified from OC patient ascites, and patients were recruited by the Women's Oncology clinic in the Winthrop P. Rockefeller Cancer Institute, University of Arkansas for Medical Sciences, under an IRB-approved protocol. Additional patient samples were provided by Mayo Clinic Ovarian Cancer SPORE program under an IRF-approved protocol. Ovarian tumor cells were cultured as previously described by Nounamo et al., 2017 (PMID: 28875159). RNA extraction (Zymo Research), cDNA synthesis (New England Biolabs, Inc.), and qRT-PCR (New England Biolabs, Inc.) were performed according to manufacturer instructions.

THP-1 Luc (Invivogen) were cultured in RMPI 1640 medium supplemented with 10% fetal bovine serum (FBS; Atlanta Biologicals), 2 mM glutamine (Corning), 100 µg/ml penicillin/streptomycin (Pen/Strep; Invitrogen), and 25 mM HEPES recommended by the cell vendor. To determine IRF-dependent luciferase expression as surrogate readout of IFN-I, we assessed the luciferase activity using QUANTI-LUC (Invivogen).

The syngeneic ID8 Trp53$^{-/-}$ tumor cells were previously described by Walton et al., 2016 (PMID: 27530326) and the implantation model in immunocompetent mice was also described in the same paper. Treatment dose of cisplatin and MYXV were the same as previously described by Nounamo et al., 2017 (PMID: 28875159). Treatment schedules of the study are shown in FIG. 10A, and the left side of both FIGS. 11A and 11B.

Figure 12:
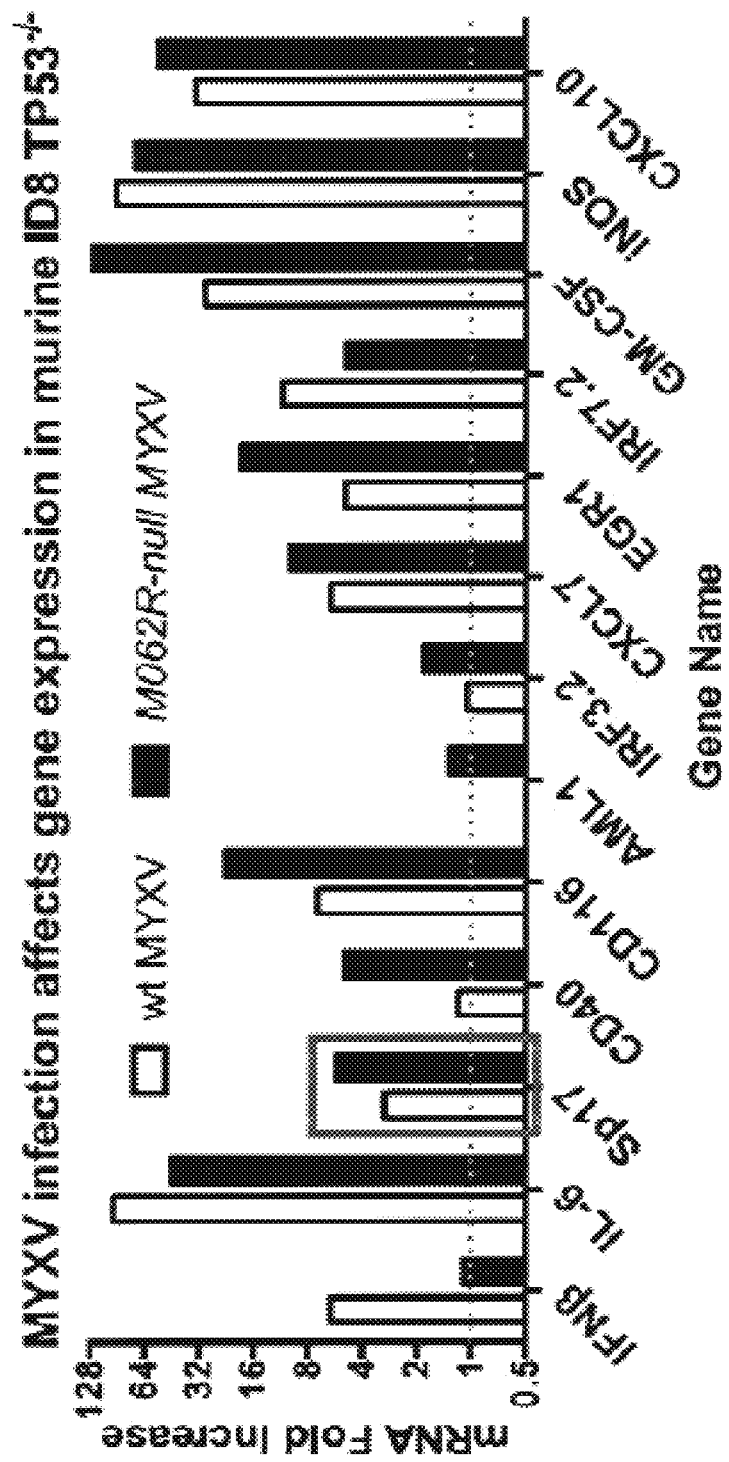

Example 3: M062RKO Myxoma Virus (MYXV) Stimulates the Inflammatory Response and UpRegulates Expression of Tumor Antigen in Cancer Cells that has Significant Therapeutic Implications Results WT MYXV infection of human OC tumor cells that were purified from OC patients and murine OC tumor cells provoked IFNβ expression as well as proinflammatory cytokines and IFN-stimulated genes (ISGs) (FIGS. 12 and 13, respectively). This inflammatory response can also be observed in cells infected with M062RKO virus. More importantly, we found that either virus stimulated the expression of Sp17, a tumor antigen that often is upregulated in malignancy and which polypeptide has been used for DC vaccine preparation.

Materials and Methods

Human OC patient tumor cells were purified from OC patient ascites, and patients were recruited by the Women's Oncology clinic in the Winthrop P. Rockefeller Cancer Institute, University of Arkansas for Medical Sciences, under an IRB-approved protocol. Additional patient samples were provided by Mayo Clinic Ovarian Cancer SPORE program under an IRF-approved protocol. Ovarian tumor cells were cultured as previously described by Nounamo et al., 2017 (PMID: 28875159). The syngeneic ID8 Trp53$^{-/-}$ tumor cells were previously described by Walton et al., 2016 (PMID: 27530326). Viral infection was conducted as described previously (PMID: 28875159). RNA extraction (Zymo Research), cDNA synthesis (New England Biolabs, Inc.), and qRT-PCR (New England Biolabs, Inc.) were performed according to manufacturer instructions.

Example 4: An Investigation of the Mechanism by which Myxoma Virus M062 Antagonizes the SAMD9-Mediated Type I Interferon Response Introduction SAMD9 (sterile alpha motif domain-containing 9, encoded by the SAMD9 gene in humans) is a poorly-understood but critical cytoplasmic protein to human health. Deleterious mutations in SAMD9 lead to many diseases, including cancer, inflammatory diseases, and disorders with complex syndromes. Intriguingly, diverse poxviruses from the family Chordopoxvirinae repeatedly inhibit the function of SAMD9 with many viral proteins. We identified myxoma virus (MYXV) M062 protein, a member of the highly-conserved poxvirus C7L superfamily, to be a potent inhibitor of SAMD9. Herein we present evidence supporting a model in which SAMD9 modulates the production of type I IFN (IFN-I) in response to poxvirus infection or the presence of cytoplasmic DNA. MYXV utilizes M062 to disarm SAMD9 and thus mitigates the IFN-I response.

Results

We utilize THP-1-Lucia cells that express luciferase under the control of an IRF-inducible promoter as a surrogate system to examine M062R-null MYXV effect in stimulating IFN-I. This cell system is not responsive to stimuli of NFκB or AP-1. After THP-1 Lucia differentiated macrophages were transfected with IFN stimulating DNA (ISD) or infected with WT or M062R-null (vMyxM062RKO) MYXV, we observed a marked increase in luciferase activity was associated with infection by vMyxM062RKO and ISD transfection, while WT MYXV infection effectively inhibited IFN-I responses (FIG. 14A/FIG. 9E. However, M062R-null MYXV infection led to a much more dramatic effect than that by ISD (FIG. 14A/FIG. 9E. We next utilized qRT-PCR and detected a sharp increase in the quantity of IFNβ mRNA early during vMyxM062RKO infection (FIG. 14B). As a control, ISD also stimulated IFNβ expression but in a less magnitude than that of M062R-null MYXV. However, WT MYXV infection effectively suppressed IFNβ induction.

Figure 15A:
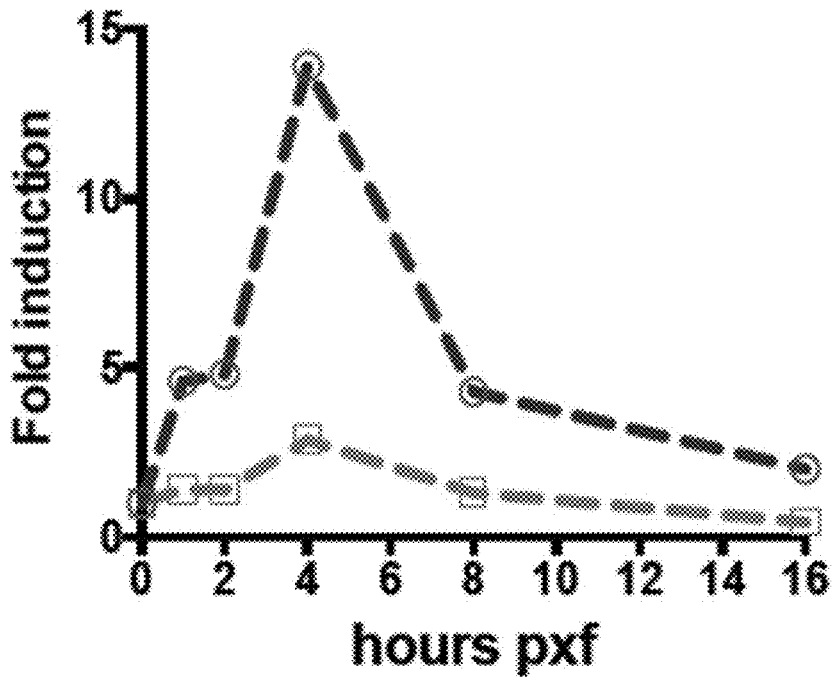
Figure 15B:
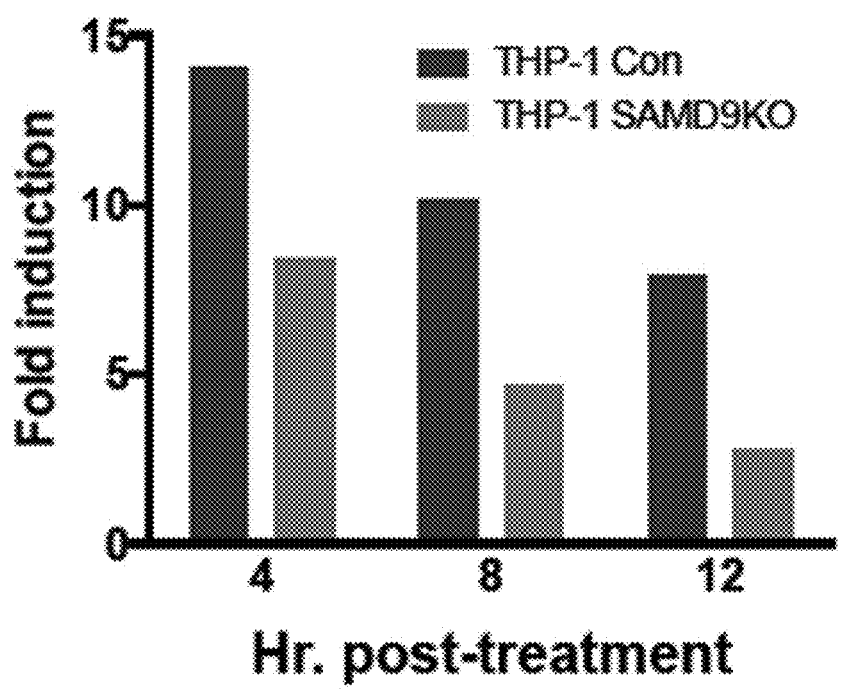
Figure 15C:
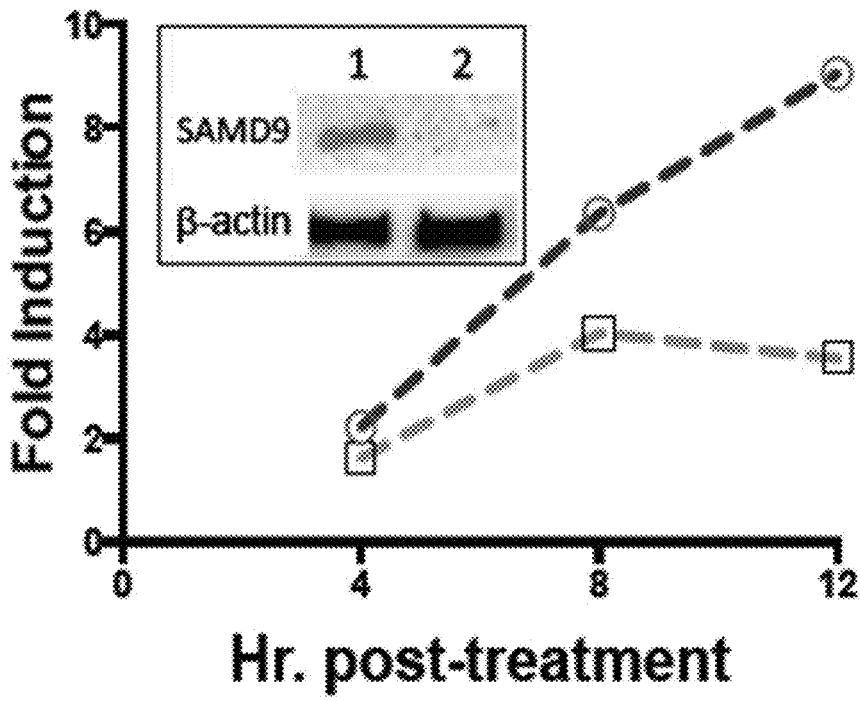
Figure 15D:
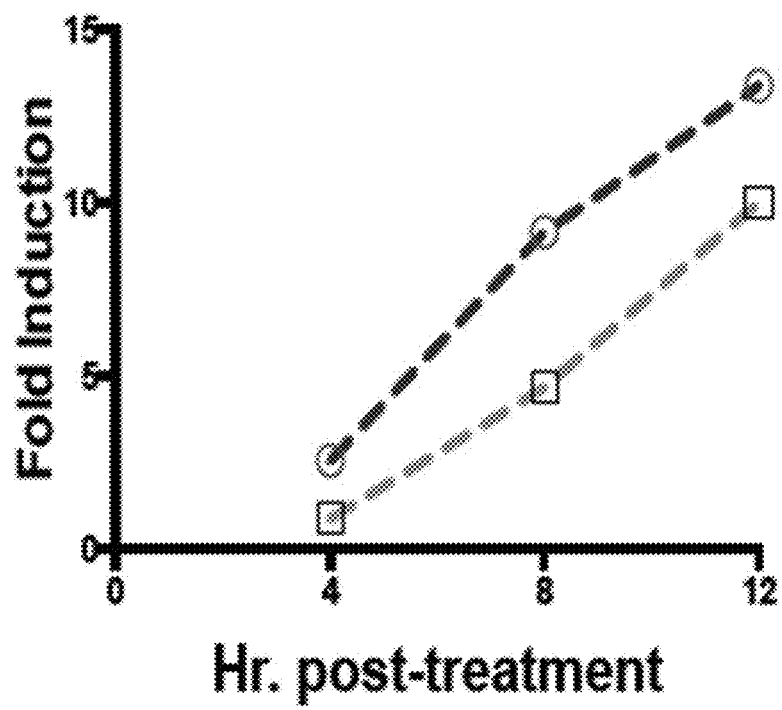

Because the host target of M062 protein is SAMD9 (PMID: 21248034, 25428864, and 28157624), we next examined if SAMD9 is responsible for the immunostimulatory response by M062R-null MYXV infection. We therefore engineered THP-1 cells stably expressing shRNAs targeting SAMD9 for gene knockdown (SAMD9 KD), and as a control THP-1 cells were constructed to stably express scramble shRNAs (FIG. 15C inset Lane 2 and 1, respectively). We found that in THP-1 differentiated macrophages with SAMD9 KD when they were transfected with ISD, the expression of IFNβ mRNA that was measured by qRT-PCR was significantly reduced (FIG. 15A). The expression of IFNβ (FIG. 15B) and the IFN stimulated genes (ISGs), such as ISG54 (FIG. 15C) and CXCL-10 (FIG. 15D) were also significantly reduced in SAMD9 KD cells infected with vMyxM062RKO. In every case, the SAMD9-ablated cells mount a smaller IFN-I response than do the SAMD9-competent cells.

Figure 16A:
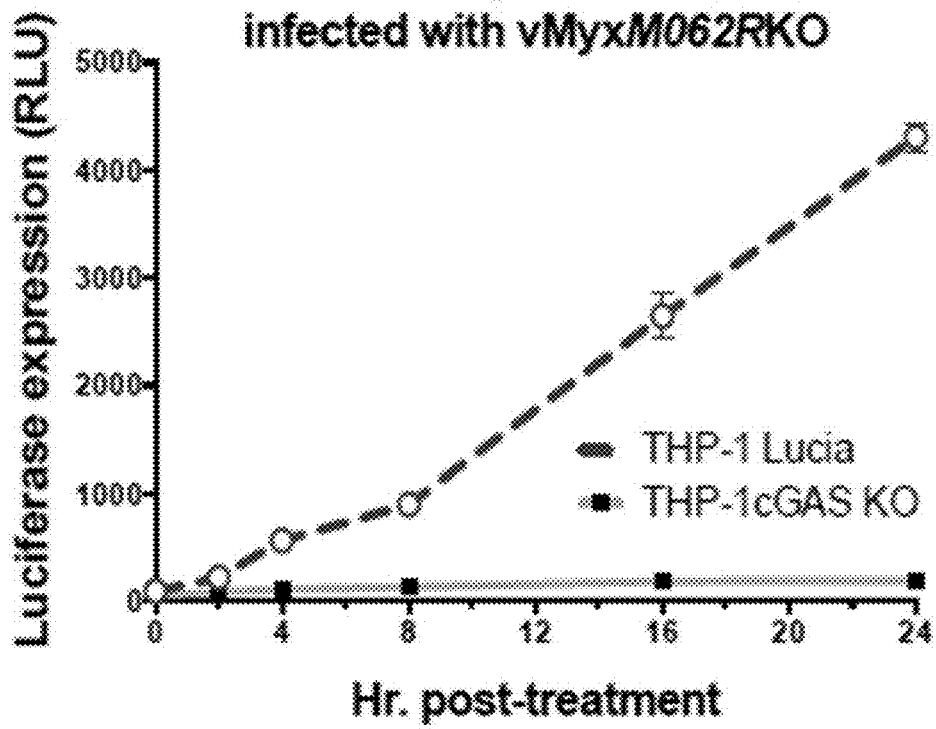
Figure 16B:
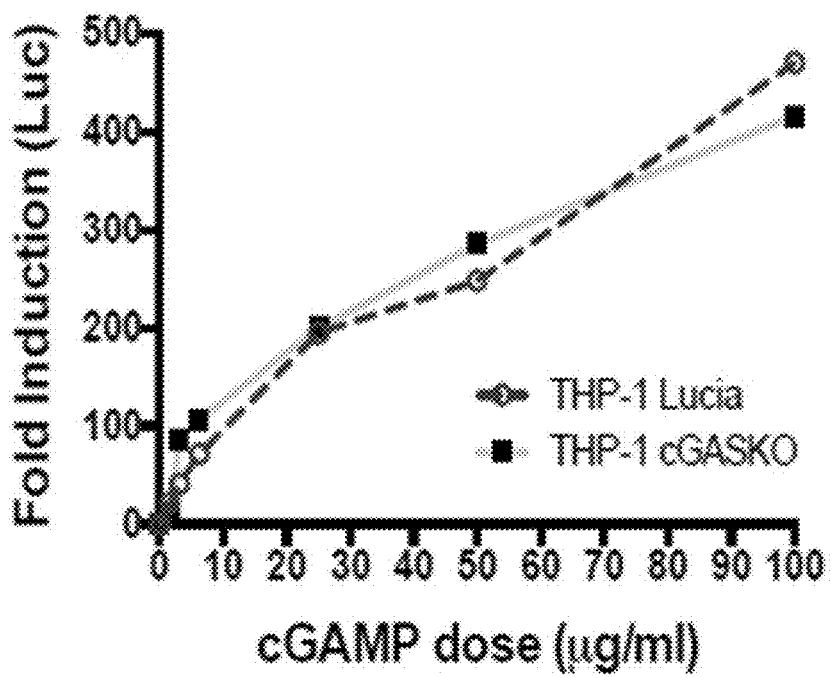
Figure 16C:
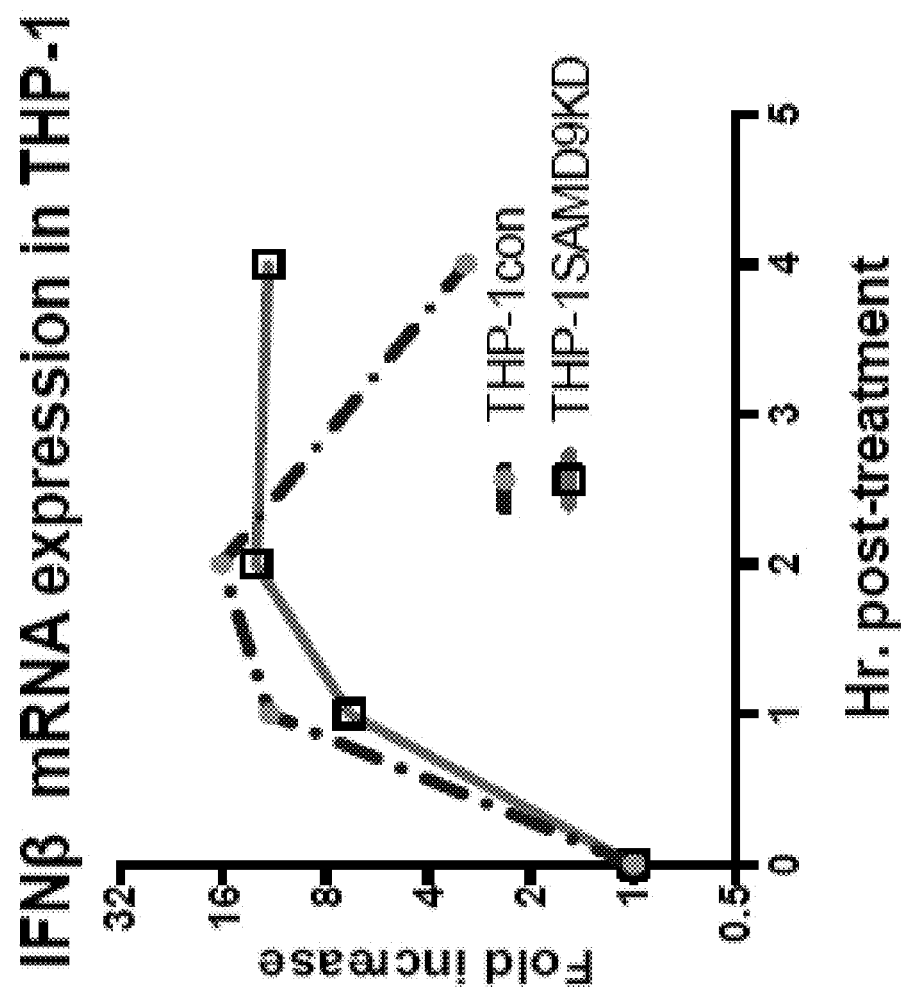

Because the lack of SAMD9 affected IFN-I induction by ISD that is sensed by DNA sensing pathways, we thus investigated the relationship of SAMD9 in IFN-I induction to known DNA sensing pathways that induce IFN-I. We focused on the axis of cyclic GMP-AMP synthase (cGAS), as it is a major DNA sensing pathway responsible for ISD-stimulated IFN-I induction. We tested M062R-null MYXV in THP-1 cells that had been deleted cGAS (cGAS-null THP-1). As we predicted in cGAS-null THP-1 differentiated macrophages infected with vMyxM062RKO failed to generate an IFN-I response, in sharp contrast to the infection of cGAS-intact cells (FIG. 16A). While exposure to 2'3'-cGAMP induces a similar increase in luciferase expression (a surrogate for IFNβ) from both THP-1 with and without cGAS (FIG. 16B). More importantly, SAMD9 KD cells responded by expressing IFNβ message RNA comparably to control cells when they are exposed to 2'3'-cGAMP that was measured by qRT-PCR (FIG. 16C).

Figure 17A:
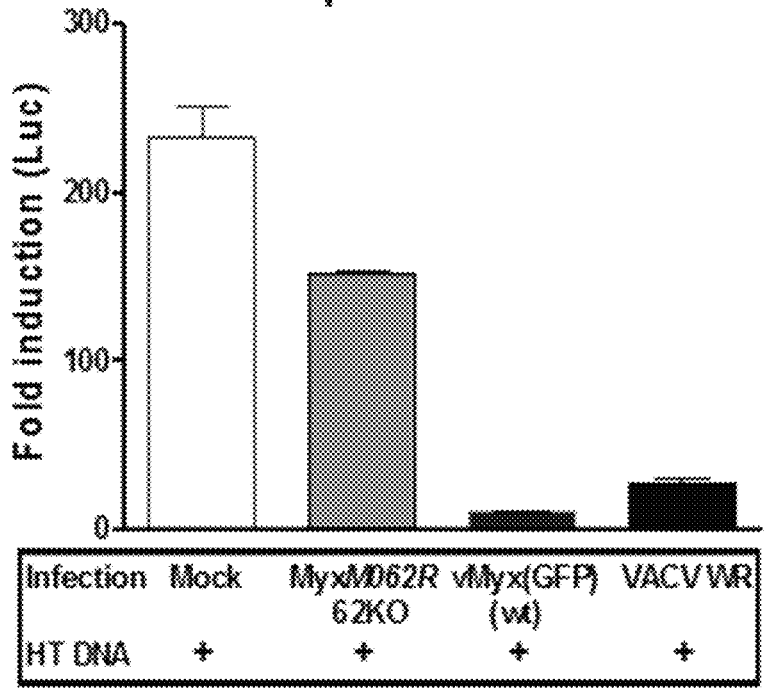

Finally, to directly determine whether M062 protein inhibits cellular IFN-I responses to DNA via disarming SAMD9, we tested DNA-stimulated IFN-I induction in the presence of WT or M062R-null MYXV infection. As a control, WT vaccinia virus (VACV) infection was included; this was because an earlier study from others (PMID: 29491158) showed WT VACV capable of inhibiting DNA-provoked IFN-I responses. We found that in fact M062R-null MYXV infection was unable to inhibit IFN-I responses caused by double-stranded DNA (dsDNA), while WT MYXV expressing M062 was fully able to inhibit dsDNA-stimulated IFN-I that was comparable to WT VACV (FIG. 17A).

Figure 17B:
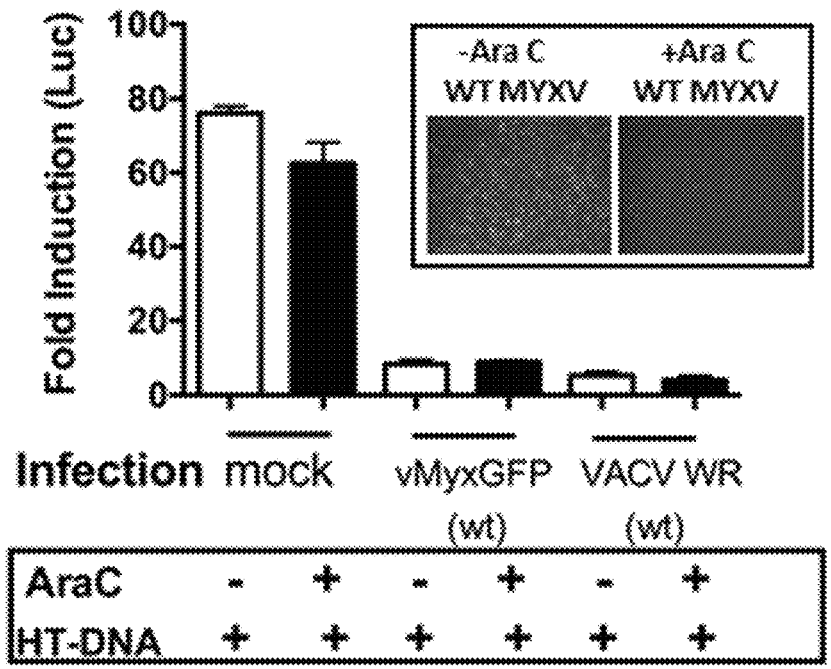

In these experiments, THP-1 Lucia cells were infected with the indicated viruses followed by transfection with herring testis (HT) DNA and the effect upon the induction of the IFN-I response was determined by luciferase assay. In addition, by selectively inhibiting post-replicative expression of viral proteins including M062 using cytosine arabinoside (Ara C) WT MYXV and VACV infections are sufficient to inhibit DNA-stimulated IFN-I. Because WT MYXV was engineered to express green fluorescent protein (GFP) that was driven by a synthetic promoter combined with strength to initiate early and later gene expression, we were able to use GFP intensity as an indicator of early or combination of early and late gene expression. We confirmed that the treatment of Ara C effectively inhibited post-replicative protein synthesis, as in Ara C treated WT MYXV infected cells very little GFP expression was detected (FIG. 17B inset, right) in comparison to WT MYXV infected cells in the absence of AraC (FIG. 17B inset, left). M062 is expressed early and post-replicatively (PMID: 21248034), and is packaged into the virion core (PMID: 22379095). Because the limited amount that is presence in the virion core, it is highly likely that M062 synthesized at the early time are responsible for the inhibition of DNA-mediated IFN-I.

Discussion

M062R-null MYXV potently induces the IFN-I response, because it lacks the M062 protein to mitigate the host measures, which limit its replication. Our data suggests that the induction of IFN-I by vMyxM062RKO depends on both SAMD9 and the cGAS-STING-TBK-1-IRF3 signaling axis. Infection by vMyxM062RKO triggered potent IRF3-dependent gene expression at time points as early as 4 hrs. p.i. for IFNβ mRNA and 6 hrs. p.i. for proteins (luciferase). Meanwhile mRNA levels of ISGs such as CXCL-10 and ISG54 were temporally delayed compared with IFNβ. Moreover, the defect of SAMD9KD cells is not at the STING activation step, which depends on 2'3'-cGAMP binding to STING. Similar to WT VACV, WT MYXV infection inhibits DNA-stimulated IFN-I, and M062 contributes to this inhibitory effect. We propose that SAMD9 acts upstream of STING activation to effectively sense poxvirus infection and that M062 acts to neutralize SAMD9.

Materials and Methods

Herring testis (HT) DNA (SigmaAldrich) and ISD (IDT) were used to stimulate IFN-I, while 2'3'-cGAMP (Invivogen) were used to bypass cGAS function and induce IFN-I. Transfection was conducted using viafect (Promega) following manufacturer's instruction. THP-1 Luc (Invivogen) and derived cGAS-null THP-1 Luc cells are cultured in RMPI 1640 medium supplemented with 10% fetal bovine serum (FBS; Atlanta Biologicals), 2 mM glutamine (Corning), 100 µg/ml penicillin/streptomycin (Pen/Strep; Invitrogen), and 25 mM HEPES recommended by the cell vendor. RNA extraction (Zymo Research), cDNA synthesis (New England Biolabs, Inc.), and qRT-PCR (New England Biolabs, Inc.) were performed according to manufacturer instructions. To determine IRF-dependent luciferase expression as surrogate readout of IFN-I, we assessed the luciferase activity using QUANTI-LUC (Invivogen).

Example 5: MYXV Immunotherapeutic Potential in a T Cell-TAM Co-Culture System

Results

Figure 18:
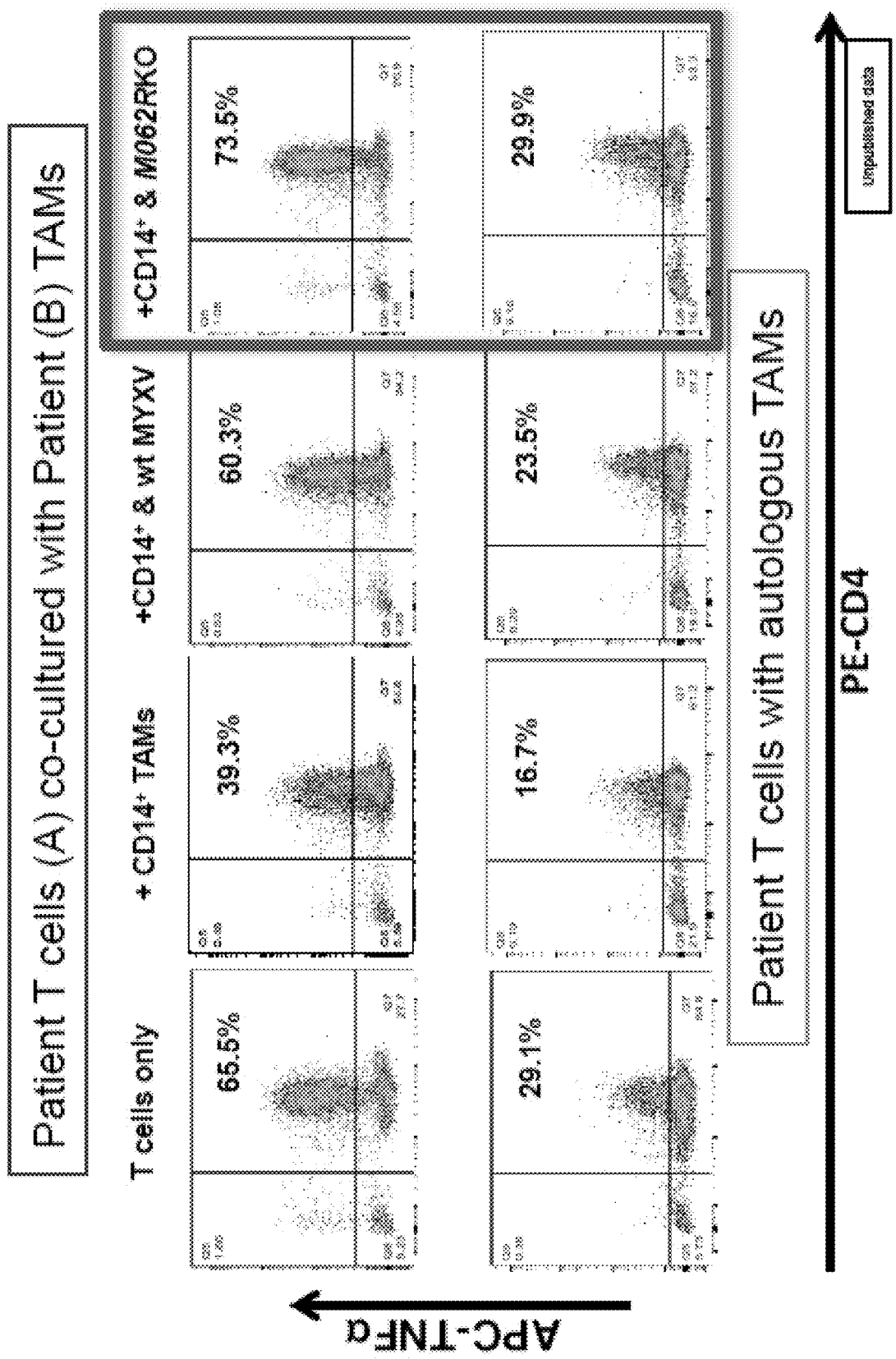
FIG. 18 shows MYXV immunotherapeutic potential in a T cell-TAM co-culture system.

By stimulating CD4+ T cells with antigen presenting cells pulsed with the OC tumor antigens, we detected basal level of CD4+ T cell response by intracellular TNF staining (FIG. 18; column 1: T cell only). However, when we co-cultured CD4+ T cells with CD14+ TAMs from another patient (top row) or autologous (bottom row), CD4+ T cell response to OC tumor antigen is significantly inhibited (FIG. 18; column 2: CD14+ TAMs). We conducted similar co-culture experiments using CD14+ TAMs that had either been infected with WT MYXV or M062RKO virus followed by OC tumor antigen stimulation. We found that WT MYXV infection of CD14+ TAMs partially restored CD4+ T cell responses; infection by M062RKO virus in these TAMs dramatically enhanced the CD4+ T cell response. In conclusion, MYXV infection of CD14+ TAMs subverts immunosuppressive function, and M062RKO virus is especially effective in treating and eliminating CD14+ TAMs of OC microenvironment. Thus we concluded that M062RKO virus has enhanced therapeutic potential as it not only stimulated IFN-I responses after infecting tumor cells but also eliminated the functions of CD14+ TAMs from maintaining the immunosuppressive tumor environment.

Materials and Methods

Ovarian cancer patients were recruited from patients attending the Women's Oncology clinic in the Winthrop P. Rockefeller Cancer Institute, University of Arkansas for Medical Sciences, under an IRB-approved protocol.

From OC patient ascites, purification of CD14+ tumor associated myeloid cells (TAMs) and CD4+ T cells, co-culture set up, and CD4+ T cell stimulation were performed as previously reported (PMID: 24598451). To test MYXV therapeutic effect, we first allowed binding of MYXV virus to CD14+ TAMs for an hour and wash with DPBS (Lonza) to rid of unbound viruses. We then co-cultured TAMs with CD4+ T cells for 48 hrs before stimulation with OC tumor antigen pulsed antigen-presenting cells. At 24 hrs post-stimulation, we examined the T cell response by flow cytometry. Results are shown in FIG. 18.

Figure 19:
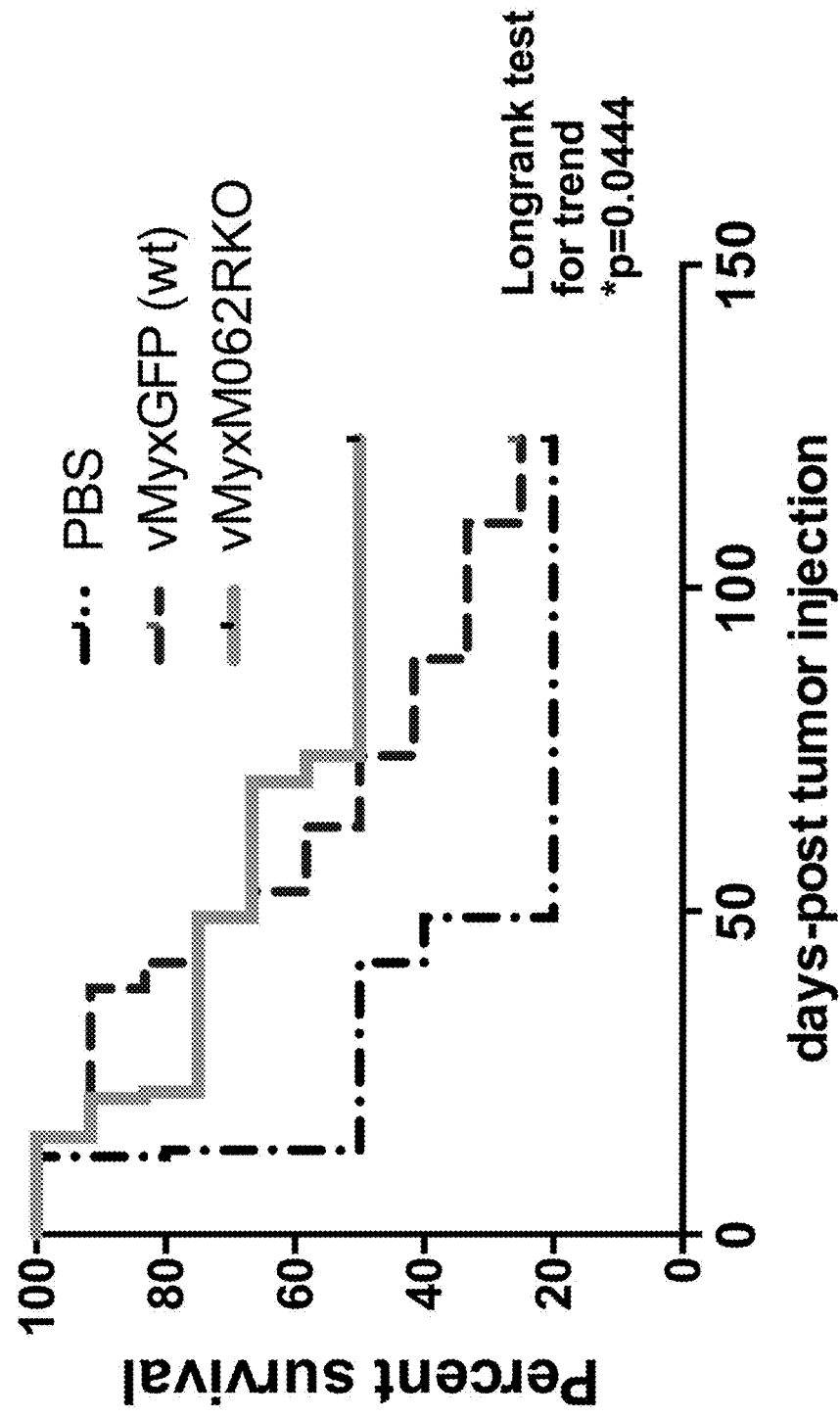
FIG. 19 shows MYXV immunotherapeutic potential in a pancreatic cancer metastatic model.

Example 6: Immunotherapeutic Potential of MYXV in Pancreatic Cancer Metastatic Model In a syngeneic murine pancreatic cancer model with peritoneal carcinomatosis, we found that treatment with M062RKO further improved survival compared with WT MYXV treatment. We utilize a pancreatic cancer peritoneal carcinomatosis model to examine the treatment outcome by WT and M062RKO viruses. The model system was previously described by Weinner et al. (PMID: 22233582). We injected more cancer cells (6 million of murine PANO2 cells) than what was reported (PMID: 22233582) through the intraperitoneal route to produce an aggressive form of the disease and treated mice with the same treatment schedule as in PMID 22233582. Statistical analysis was carried out with the log-rank (Mantel-Cox) test and the Gehan-Breslow-Wilcoxon test. The statistical significance is defined as p<0.05. Results are shown in FIG. 19.

Example 7: Mutant MYXV can Enhance PARP Inhibitor in the Treatment of Cancer

Poly (ADP-ribose) polymerase 1 (PARP1) plays a pivotal role in cellular biological processes including DNA repair and gene transcription and has been found to be overexpressed in an number of carcinomas. PARP1 has been shown to be overexpressed significantly in malignant tissues of BRCA-mutant, triple negative (TN) and receptor-positive breast carcinoma (BRCA-mutant/triple negative (TN)>receptor-positive), as well as uterine carcinoma, ovarian carcinoma, lung carcinoma, skin carcinoma, and non-Hodgkin's lymphoma[50]. We believe that the combination of the mutant myxoma virus in combination with PARP inhibitors will enhance the anti-tumor properties of the PARP1 inhibitor by altering the immunosuppressive tumor microenvironment to an immune active site.

Similar to the above-Example 2, a treatment regimen will be tested in a model of OC model (a syngeneic ID8 Trp53$^{-/-}$ tumor cell implantation model in immunocompetent mice) that closely portrays human high grade serous OC (HGSOC). A PARP1 inhibitor will be administered in combination with the mutant myxoma virus which is believed will improve survival compared with WT MYXV treatment, or PARP1 treatment alone.

Example 8: Mutant MYXV can Enhance Checkpoint Inhibitor Treatment in Cancer

Checkpoint inhibitors, including PD-1, PD-L1, CTLA-4, are checkpoint proteins on T cells that help keep the T cells from attacking other cells in the body but are often dysregulated in cancer cells allowing tumor cells to evade the immune system. Thus, many inhibitors that target either PD-1 or PD-L1 can block this binding and boost the immune response against cancer cells. However, these drugs have been shown to fail as anti-cancer drugs in ovarian cancer. We believe if the checkpoint inhibitors are used in combination with the mutant myxomavirus to treat subjects, the efficacy of the treatment can be improved as an anti-cancer combination.

Similar to the above-Example 2, a treatment regimen will be tested in a model of OC model (a syngeneic ID8 Trp53$^{-/-}$ tumor cell implantation model in immunocompetent mice) that closely portrays human high grade serous OC (HGSOC). The mutant myxoma virus will be administered along with an anti-PD1 inhibitor (Pembrolizumab (Keytruda), Nivolumab (Opdivo) Cemiplimab (Libtayo)), anti-PD-L1 inhibitor (Atezolizumab (Tecentriq), Avelumab (Bavencio), Durvalumab (Imfinzi) or an anti-CTLA-4 antibody (ipilimumab, Yervoy), and compared to treatment with the checkpoint inhibitors alone. We believe the combination with the mutant myxomavirus will improve survival compared with the treatment with the checkpoint inhibitor alone.

REFERENCES

1. Bukowski R. M., Ozols R. F., Markman M. The management of recurrent ovarian cancer. Semin. Oncol. 2007; 34(Suppl 2): S1-S15.
2. Ozols R. F. Challenges for chemotherapy in ovarian cancer. Ann. Oncol. 2006; 17(Suppl 5):v181-v187.
3. Zhang L., Conejo-Garcia J. R., Katsaros D., Gimotty P. A., Massobrio M., Regnani G., Makrigiannakis A., Gray H., Schlienger K., Liebman M. N. Intratumoral T cells, recurrence, and survival in epithelial ovarian cancer. N. Engl. J. Med. 2003; 348:203-213.
4. Curiel T. J., Coukos G., Zou L., Alvarez X., Cheng P., Mottram P., Evdemon-Hogan M., Conejo-Garcia J. R., Zhang L., Burow M. Specific recruitment of regulatory T cells in ovarian carcinoma fosters immune privilege and predicts reduced survival. Nat. Med. 2004; 10:942-949.
5. Cannon M. J., Ghosh D., Gujja S. Signaling circuits and regulation of immune suppression by ovarian tumor-associated macrophages. Vaccines (Basel) 2015; 3:448-466.
6. Goyne H. E., Cannon M. J. Dendritic cell vaccination, immune regulation, and clinical outcomes in ovarian cancer. Front. Immunol. 2013; 4:382.
7. Fukuhara H., Ino Y., Todo T. Oncolytic virus therapy: a new era of cancer treatment at dawn. Cancer Sci. 2016; 107:1373-1379.
8. Kaufman H. L., Kohlhapp F. J., Zloza A. Oncolytic viruses: a new class of immunotherapy drugs. Nat. Rev. Drug Discov. 2015; 14:642-662.
9. Arulanandam R., Batenchuk C., Varette O., Zakaria C., Garcia V., Forbes N. E., Davis C., Krishnan R., Karmacharya R., Cox J. Microtubule disruption synergizes with oncolytic virotherapy by inhibiting interferon translation and potentiating bystander killing. Nat. Commun. 2015; 6:6410.
10. Bilsland A. E., Spiliopoulou P., Evans T. R. Virotherapy: cancer gene therapy at last? [version 1; referees: 2 approved] F1000Res. 2016; 5:2105.
11. Woller N., Gürlevik E., Ureche C. I., Schumacher A., Kühnel F. Oncolytic viruses as anticancer vaccines. Front. Oncol. 2014; 4:188.
12. Thorne S. H., Liang W., Sampath P., Schmidt T., Sikorski R., Beilhack A., Contag C. H. Targeting localized immune suppression within the tumor through repeat cycles of immune cell-oncolytic virus combination therapy. Mol. Ther. 2010; 18:1698-1705.
13. Keller B. A., Bell J. C. Oncolytic viruses-immunotherapeutics on the rise. J. Mol. Med. (Berl.) 2016; 94:979-991.
14. Wennier S. T., Liu J., McFadden G. Bugs and drugs: oncolytic virotherapy in combination with chemotherapy. Curr. Pharm. Biotechnol. 2012; 13:1817-1833.
15. Simpson G. R., Relph K., Harrington K., Melcher A., Pandha H. Cancer immunotherapy via combining oncolytic virotherapy with chemotherapy: recent advances. Oncolytic Virother. 2016; 5:1-13.
16. Chan W. M., Rahman M. M., McFadden G. Oncolytic myxoma virus: the path to clinic. Vaccine. 2013; 31:4252-4258.
17. Wang F., Gao X., Barrett J. W., Shao Q., Bartee E., Mohamed M. R., Rahman M., Werden S., Irvine T., Cao J. RIG-I mediates the co-induction of tumor necrosis factor and type I interferon elicited by myxoma virus in primary human macrophages. PLoS Pathog. 2008; 4:e1000099.
18. Wang F., Barrett J. W., Ma Y., Dekaban G. A., McFadden G. Induction of alpha/beta interferon by myxoma virus is selectively abrogated when primary mouse embryo fibroblasts become immortalized. J. Virol. 2009; 83:5928-5932.
19. Correa R. J., Komar M., Tong J. G., Sivapragasam M., Rahman M. M., McFadden G., Dimattia G. E., Shepherd T. G. Myxoma virus-mediated oncolysis of ascites-derived human ovarian cancer cells and spheroids is impacted by differential AKT activity. Gynecol. Oncol. 2012; 125:441-450.
20. Tong J. G., Ramos Valdes Y., Barrett J. W., Bell J. C., Stojdl D., McFadden G., McCart J. A., DiMattia G. E., Shepherd T. G. Evidence for differential viral oncolytic efficacy in an in vitro model of epithelial ovarian cancer metastasis. Mol. Ther. Oncolytics. 2015; 2:15013.
21. Wennier S. T., Liu J., Li S., Rahman M. M., Mona M., McFadden G. Myxoma virus sensitizes cancer cells to gemcitabine and is an effective oncolytic virotherapeutic in models of disseminated pancreatic cancer. Mol. Ther. 2012; 20:759-768.
22. Moo-Young T. A., Larson J. W., Belt B. A., Tan M. C., Hawkins W. G., Eberlein T. J., Goedegebuure P. S., Linehan D. C. Tumor-derived TGF-beta mediates conversion of CD4+Foxp3+ regulatory T cells in a murine model of pancreas cancer. J. Immunother. 2009; 32:12-21.
23. Tan M. C., Goedegebuure P. S., Belt B. A., Flaherty B., Sankpal N., Gillanders W. E., Eberlein T. J., Hsieh C. S., Linehan D. C. Disruption of CCR5-dependent homing of regulatory T cells inhibits tumor growth in a murine model of pancreatic cancer. J. Immunol. 2009; 182:1746-1755.
24. Dasari S., Tchounwou P. B. Cisplatin in cancer therapy: molecular mechanisms of action. Eur. J. Pharmacol. 2014; 740:364-378.
25. Tseng C. W., Hung C. F., Alvarez R. D., Trimble C., Huh W. K., Kim D., Chuang C. M., Lin C. T., Tsai Y. C., He L. Pretreatment with cisplatin enhances E7-specific CD8+ T-cell-mediated antitumor immunity induced by DNA vaccination. Clin. Cancer Res. 2008; 14:3185-3192.
26. Pandha H. S., Heinemann L., Simpson G. R., Melcher A., Prestwich R., Errington F., Coffey M., Harrington K. J., Morgan R. Synergistic effects of oncolytic reovirus and cisplatin chemotherapy in murine malignant melanoma. Clin. Cancer Res. 2009; 15:6158-6166.
27. Moehler M., Sieben M., Roth S., Springsguth F., Leuchs B., Zeidler M., Dinsart C., Rommelaere J., Galle P. R. Activation of the human immune system by chemotherapeutic or targeted agents combined with the oncolytic parvovirus H-1. BMC Cancer. 2011; 11:464.
28. Wilke C. M., Kryczek I., Zou W. Antigen-presenting cell (APC) subsets in ovarian cancer. Int. Rev. Immunol. 2011; 30:120-126.
29. Chan W. M., Bartee E. C., Moreb J. S., Dower K., Connor J. H., McFadden G. Myxoma and vaccinia viruses bind differentially to human leukocytes. J. Virol. 2013; 87:4445-4460.
30. Gujar S. A., Clements D., Dielschneider R., Helson E., Marcato P., Lee P. W. Gemcitabine enhances the efficacy of reovirus-based oncotherapy through anti-tumour immunological mechanisms. Br. J. Cancer. 2014; 110:83-93.
31. Wang G., Barrett J. W., Stanford M., Werden S. J., Johnston J. B., Gao X., Sun M., Cheng J. Q., McFadden G. Infection of human cancer cells with myxoma virus requires Akt activation via interaction with a viral ankyrin-repeat host range factor. Proc. Natl. Acad. Sci. USA. 2006; 103:4640-4645.
32. Bartee E., McFadden G. Human cancer cells have specifically lost the ability to induce the synergistic state caused by tumor necrosis factor plus interferon-beta. Cytokine. 2009; 47:199-205.
33. Bartee E., Mohamed M. R., Lopez M. C., Baker H. V., McFadden G. The addition of tumor necrosis factor plus beta interferon induces a novel synergistic antiviral state against poxviruses in primary human fibroblasts. J. Virol. 2009; 83:498-511.
34. Dunlap K. M., Bartee M. Y., Bartee E. Myxoma virus attenuates expression of activating transcription factor 4 (ATF4) which has implications for the treatment of proteasome inhibitor-resistant multiple myeloma. Oncolytic Virother. 2015; 4:1-11.
35. Bartee M. Y., Dunlap K. M., Bartee E. Myxoma virus induces ligand independent extrinsic apoptosis in human myeloma cells. Clin. Lymphoma Myeloma Leuk. 2016; 16:203-212.
36. Dijkgraaf E. M., Heusinkveld M., Tummers B., Vogelpoel L. T., Goedemans R., Jha V., Nortier J. W., Welters M. J., Kroep J. R., van der Burg S. H. Chemotherapy alters monocyte differentiation to favor generation of cancer-supporting M2 macrophages in the tumor microenvironment. Cancer Res. 2013; 73:2480-2492.
37. Loercher A. E., Nash M. A., Kavanagh J. J., Platsoucas C. D., Freedman R. S. Identification of an IL-10-producing HLA-DR-negative monocyte subset in the malignant ascites of patients with ovarian carcinoma that inhibits cytokine protein expression and proliferation of autologous T cells. J. Immunol. 1999; 163:6251-6260.
38. Goyne H. E., Stone P. J., Burnett A. F., Cannon M. J. Ovarian tumor ascites CD14+ cells suppress dendritic cell-activated CD4+ T-cell responses through IL-10 secretion and indoleamine 2,3-dioxygenase. J. Immunother. 2014; 37:163-169.
39. Walton J., Blagih J., Ennis D., Leung E., Dowson S., Farquharson M., Tookman L. A., Orange C., Athineos D., Mason S. CRISPR/Cas9-mediated Trp53 and Brca2 knockout to generate improved murine models of ovarian high-grade serous carcinoma. Cancer Res. 2016; 76:6118-6129.
40. Han Z., Hong Z., Gao Q., Chen C., Hao Z., Ji T., Hu W., Yan Y., Feng J., Liao S. A potent oncolytic adenovirus selectively blocks the STAT3 signaling pathway and potentiates cisplatin antitumor activity in ovarian cancer. Hum. Gene Ther. 2012; 23:32-45.
41. Nair R. R., Tolentino J. H., Hazlehurst L. A. Role of STAT3 in transformation and drug resistance in CML. Front. Oncol. 2012; 2:30.
42. Schust J., Sperl B., Hollis A., Mayer T. U., Berg T. Stattic: a small-molecule inhibitor of STAT3 activation and dimerization. Chem. Biol. 2006; 13:1235-1242.
43. Beyranvand Nejad E., van der Sluis T. C., van Duikeren S., Yagita H., Janssen G. M., van Veelen P. A., Melief C. J., van der Burg S. H., Arens R. Tumor eradication by cisplatin is sustained by CD80/86-mediated costimulation of CD8+ T cells. Cancer Res. 2016; 76:6017-6029.
44. Liu J., McFadden G. SAMD9 is an innate antiviral host factor with stress response properties that can be antagonized by poxviruses. J. Virol. 2015; 89:1925-1931.
45. Mirandola L., Yu Y., Cannon M. J., Jenkins M. R., Rahman R. L., Nguyen D. D., Grizzi F., Cobos E., Figueroa J. A., Chiriva-Internati M. Galectin-3 inhibition suppresses drug resistance, motility, invasion and angiogenic potential in ovarian cancer. Gynecol. Oncol. 2014; 135:573-579.
46. Roby K. F., Taylor C. C., Sweetwood J. P., Cheng Y., Pace J. L., Tawfik O., Persons D. L., Smith P. G., Terranova P. F. Development of a syngeneic mouse model for events related to ovarian cancer. Carcinogenesis. 2000; 21:585-591.
47. Liu J., Wennier S., Zhang L., McFadden G. M062 is a host range factor essential for myxoma virus pathogenesis and functions as an antagonist of host SAMD9 in human cells. J. Virol. 2011; 85:3270-3282.
48. Liu J., Wennier S., Moussatche N., Reinhard M., Condit R., McFadden G. Myxoma virus M064 is a novel member of the poxvirus C7L superfamily of host range factors that controls the kinetics of myxomatosis in European rabbits. J. Virol. 2012; 86:5371-5375.
49. Chang C. L., Hsu Y. T., Wu C. C., Lai Y. Z., Wang C., Yang Y. C., Wu T. C., Hung C. F. Dose-dense chemotherapy improves mechanisms of antitumor immune response. Cancer Res. 2013; 73:119-127.
50. Ossovskaya V, Koo I C, Kaldjian E P, Alvares C, Sherman B M. Upregulation of Poly (ADP-Ribose) Polymerase-1 (PARP1) in Triple-Negative Breast Cancer and Other Primary Human Tumor Types. Genes Cancer. 2010 August; 1(8):812-21.

We claim:

1. A method of treating cancer in a subject comprising administering a therapeutically effective amount of a myxoma virus, wherein the myxoma virus has been genetically modified to lack the Myxoma virus M62R gene.

2. The method of claim 1, further comprising administering to the subject a therapeutically effective amount of an anti-cancer therapeutic agent.

3. The method of claim 2, wherein the myxoma virus is administered at least 24 hours after the anti-cancer therapeutic agent.

4. The method of claim 2, wherein the myxoma virus is administered at least 24 hours before the anti-cancer therapeutic agent.

5. The method of claim 1, wherein the cancer comprises ovarian cancer or pancreatic cancer.

6. The method of claim 1, wherein the anti-cancer therapeutic agent is selected from the group consisting of a chemotherapeutic agent, a cancer vaccine, and a combination thereof.

7. The method of claim 6, wherein the anti-cancer therapeutic agent comprises an agent selected from the group consisting of a platinum-based chemotherapeutic agent, a PARP inhibitor and a dendritic cell (DC) vaccine.

8. The method of claim 2, wherein the cancer is ovarian cancer, wherein the subject is a human subject, and wherein the
anti-cancer therapeutic agent is administered to the human subject, and
subsequently the myxoma virus is administered to the human subject.

9. The method of claim 8, wherein the myxoma virus is administered at least 24 hours after the anti-cancer therapeutic agent.

10. The method of claim 8, wherein the anti-cancer therapeutic agent comprises an agent selected from the group consisting of a platinum-based chemotherapeutic agent, and a PARP inhibitor.

11. The method of claim 8, wherein the method comprises administering both an anti-cancer therapeutic agent and a cancer vaccine.

12. The method of claim 2, wherein the cancer is ovarian cancer, wherein the subject is a human subject, and wherein
the myxoma virus genetically modified to lack the Myxoma virus M62R gene is administered to the human subject, and
subsequently a cancer vaccine is administered to the human subject.

13. The method of claim 12, wherein the myxoma virus is administered at least 24 hours before the cancer vaccine.

14. The method of claim 12, wherein the cancer vaccine comprises a dendritic cell (DC) vaccine.

15. A method of eliciting an interferon response in a subject having cancer, the method comprising administering to the subject a therapeutically effective amount of a Myxoma virus genetically modified to lack Myxoma virus M62R gene to elicit an interferon response in the subject.

16. The method of claim 15, wherein the interferon response comprises an increase in IFN-β and IFN-I in a subject.

17. The method of claim 15, wherein the cancer subject has been treated with an anti-cancer therapeutic agent prior to eliciting the interferon response.

18. The method of claim 15, wherein the subject has been treated with an anti-cancer therapeutic agent or a cancer vaccine prior to administering the myxoma virus.

19. The method of claim 15, wherein the anti-cancer therapeutic agent is a chemotherapeutic agent, PARP inhibitor or checkpoint inhibitor.

20. A method of inhibiting, reducing or eliminating a CD14+tumor associated macrophage (TAM) inhibition of CD4+ T cells in a subject having cancer, the method comprising administering a therapeutically effective amount of a Myxoma virus genetically modified to lack Myxoma virus M62R gene to increase the CD4+ T cell response in a subject.

21. The method of claim 20, wherein the subject has been treated with an anti-cancer therapeutic agent prior to administering the myxoma virus.

* * * * *

UNITED STATES PATENT AND TRADEMARK OFFICE
CERTIFICATE OF CORRECTION

| | | |
|---|---|---|
| PATENT NO. | : 12,128,099 B2 | Page 1 of 1 |
| APPLICATION NO. | : 17/058765 | |
| DATED | : October 29, 2024 | |
| INVENTOR(S) | : Jia Liu et al. | |

It is certified that error appears in the above-identified patent and that said Letters Patent is hereby corrected as shown below:

In the Specification

Column 3, Line 3, "5727" should be --S727--.

Column 22, Line 2, "5727" should be --S727--.

Signed and Sealed this
Fourth Day of February, 2025

Coke Morgan Stewart
*Acting Director of the United States Patent and Trademark Office*